US009511015B2

(12) United States Patent
Kakkis

(10) Patent No.: US 9,511,015 B2
(45) Date of Patent: *Dec. 6, 2016

(54) METHODS AND FORMULATIONS FOR TREATING SIALIC ACID DEFICIENCIES

(75) Inventor: Emil Kakkis, Novato, CA (US)

(73) Assignee: ULTRAGENYX PHARMACEUTICAL INC., Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/810,068

(22) PCT Filed: Jul. 13, 2011

(86) PCT No.: PCT/US2011/043910
§ 371 (c)(1),
(2), (4) Date: Jun. 25, 2013

(87) PCT Pub. No.: WO2012/009474
PCT Pub. Date: Jan. 19, 2012

(65) Prior Publication Data
US 2013/0273160 A1    Oct. 17, 2013

Related U.S. Application Data

(60) Provisional application No. 61/363,995, filed on Jul. 13, 2010.

(51) Int. Cl.
| *A61K 9/20*   | (2006.01) |
| *A61K 9/00*   | (2006.01) |
| *A61K 31/7012*| (2006.01) |
| *A61K 31/335* | (2006.01) |
| *A61K 31/35*  | (2006.01) |
| *A61K 9/48*   | (2006.01) |

(52) U.S. Cl.
CPC ........... *A61K 9/0002* (2013.01); *A61K 9/2031* (2013.01); *A61K 9/2054* (2013.01); *A61K 9/2063* (2013.01); *A61K 31/7012* (2013.01); *A61K 9/20* (2013.01); *A61K 9/2004* (2013.01); *A61K 9/48* (2013.01); *A61K 31/335* (2013.01); *A61K 31/35* (2013.01)

(58) Field of Classification Search
None
See application file for complete search history.

(56) References Cited

U.S. PATENT DOCUMENTS

| 4,698,332    | A  | 10/1987 | Ogasawara et al. |
| 5,624,677    | A  | 4/1997  | El-Rashidy et al.|
| 5,747,475    | A  | 5/1998  | Nordquist et al. |
| 6,444,649    | B1 | 9/2002  | Inamori et al.   |
| 8,524,772    | B2 | 9/2013  | Arad et al.      |
| 8,840,926    | B2 | 9/2014  | Kakkis et al.    |
| 2004/0192642 | A1 | 9/2004  | Yang et al.      |
| 2008/0085306 | A1 | 4/2008  | Nangia et al.    |
| 2008/0260824 | A1 | 10/2008 | Nangia et al.    |
| 2010/0159001 | A1 | 6/2010  | Cardinal et al.  |
| 2010/0160363 | A1 | 6/2010  | Cardinal et al.  |
| 2010/0226855 | A1 | 9/2010  | Nangia et al.    |
| 2012/0264928 | A1*| 10/2012 | Noguchi et al. ................ 536/53 |
| 2013/0109637 | A1 | 5/2013  | Kakkis et al.    |
| 2013/0122094 | A1 | 5/2013  | Kakkis           |
| 2013/0225513 | A1 | 8/2013  | Kakkis           |
| 2015/0038693 | A1 | 2/2015  | Kakkis et al.    |

FOREIGN PATENT DOCUMENTS

| EP | 2332552         | 6/2011  |
| WO | WO 04/000366    | 12/2003 |
| WO | WO 2006/096161  | 9/2006  |
| WO | WO 2008/150477  | 12/2008 |
| WO | WO 2009/032605  | 3/2009  |
| WO | WO 2010/131712  | 11/2010 |
| WO | WO 2012/009474  | 1/2012  |
| WO | WO 2013/063149  | 5/2013  |
| WO | WO 2013/109906  | 7/2013  |

OTHER PUBLICATIONS

International Preliminary Report on Patentability for International Application No. PCT/US2012/061737, dated Apr. 29, 2014, 9 pages.
International Search Report and Written Opinion for International Application No. PCT/US2012/061737, mailed Mar. 15, 2013, 13 pages.
Supplementary European Search Report for European Application No. 11807478.0, mailed Dec. 5, 2013, 5 pages.
International Preliminary Report on Patentability for International Application No. PCT/US2011/043910, dated Jan. 15, 2013, 8 pages.
International Search Report and Written Opinion for International Application No. PCT/US2011/043910, mailed Oct. 18, 2011, 10 pages.
International Preliminary Report on Patentability for International Application No. PCT/US2013/022167, dated Jul. 22, 2014, 4 pages.
Aich, U. et al, "Development of Delivery Methods for Carbohydrate-based Drugs: Controlled Release of Biologically-Active Short Chain Fatty Acid-Hexosamine Analogs," Glycoconjugate Journal, 27(4):445-459 (2010).
Allevi, P. et al., "Chemoselective synthesis of sialic acid 1,7-lactones," J. Org. Chem., 75(16):5542-5548 (2010).
Argov, Z. et al., "Hereditary inclusion body myopathy. The Middle Eastern genetic cluster," Neurology, 60(9):1519-1523 (2003).
Askanas, V. et al., "Sporadic inclusion-body myositis and hereditary inclusion-body myopathies: current concepts of diagnosis and pathogenesis," Curr. Opin. Rheumatol., 10:530-542 (1998).
Broccolini, A. et al., "Novel GNE mutations in Italian families with autosomal recessive hereditary inclusion-body myopathy," Human Mutation, 23(6):632 (2004).
Rezende, M. C. et al., "A facile route to 9-phosphorylated neuraminic acid derivatives," Synthetic Communications, 28(23):4393-4400 (1998).
Colombo, R. et al., "The first synthesis of N-acetylneuraminic acid 1,7-lactone," Chem. Commun., 43:5517-5519 (2008).

(Continued)

*Primary Examiner* — James Rogers
(74) *Attorney, Agent, or Firm* — Cooley LLP

(57) ABSTRACT

The present invention relates to compositions and methods for treating sialic acid deficiencies comprising extended release formulations.

16 Claims, 9 Drawing Sheets

(56) References Cited

OTHER PUBLICATIONS

Eisenberg, I. et al., "The UDP-N-acetylglucosamine 2-epimerase/N-acetylmannosamine kinase gene is mutated in recessive hereditary inclusion body myopathy," Nat. Genet., 29(1):83-87 (2001).

Frost, R. A. et al., "Regulation of insulin-like growth factor-I in skeletal muscle and muscle cells," Minerva Endocrinol., 28(1):53-73 (2003).

Galeano, B. et al., "Mutation in the key enzyme of sialic acid biosynthesis causes severe glomerular proteinuria and is rescued by N-acetylmannosamine," The Journal of Clinical Investigation, 117(6):1585-1594 (2007).

Gavezzotti, A., "Are Crystal Structures Predictable?", Accounts of Chemical Research, 27:309-314 (1994).

Jay, C. M. et al., "Hereditary Inclusion Body Myopathy (HIBM2)," Gene Regulation and Systems Biology, 3:181-190 (2009).

Malicdan, M. C. V. et al., "Prophylactic treatment with sialic acid metabolites precludes the development of the myopathic phenotype in the DMRV-hIBM mouse model," Nature Medicine, 15(6):690-695 (2009).

Nishino, I. et al., "Distal myopathy with rimmed vacuoles is allelic to hereditary inclusion body myopathy," Neurology, 59:1689-1693 (2002).

Nishino, I. et al., "Muscular dystrophies," Current Opinion in Neurology, 15:539-544 (2002).

Noguchi, S. et al., "Reduction of UDP-N-acetylglucosamine 2-Epimerase/N-Acetylmannosamine Kinase Activity and Sialylation in Distal Myopathy with Rimmed Vacuoles," The Journal of Biological Chemistry, 279(12):11402-11407 (2004).

Oetke, C. et al., "Evidence for efficient uptake and incorporation of sialic acid by eukaryotic cells," European Journal of Biochemistry, 268(16):4553-4561 (2001).

Oetke, C. et al., "Versatile Biosynthetic Engineering of Sialic Acid in Living Cells Using Synthetic Sialic Acid Analogues," The Journal of Biological Chemistry, 277:6688-6695 (2002).

Penner, J. et al., "Influence of UDP-GlcNAc 2-Epimerase/ManNAc Kinase Mutant Proteins on Hereditary Inclusion Body Myopathy," Biochemistry, 45:2968-2977 (2006).

Pubchem Compound Database, CID 440962, "N-acetylneuraminate 9-phosphate," Created on Date: Jun. 24, 2005, 5 pages.

Ricci, E. et al., "NCAM is hyposialylated in hereditary inclusion body myopathy due to GNE mutations," Neurology, 66:755-758 (2006).

Rota, P. et al., "General and chemoselective N-transacylation of secondary amides by means of perfluorinated anhydrides," Angewandte Chemie International Edition, 49(10):1850-1853 (2010).

Seppala, R. et al., "Mutations in the Human UDP-N-Acetylglucosamine 2-Epimerase Gene Define the Disease Sialuria and the Allosteric Site of the Enzyme," Am. J. Hum. Genet., 64:1563-1569 (1999).

Sparks, S. E. et al., "Use of a cell-free system to determine UDP-N-acetylglucosamine 2-epimerase and N-acetylmannosamine kinase activities in human hereditary inclusion body myopathy," Glycobiology, 15(11):1102-1110 (2005).

Vippagunta, S. R. et al., "Crystalline Solids," Advanced Drug Delivery Reviews, 48:3-26 (2001).

Wajnrajch, M. P., "Physiological and Pathological Growth Hormone Secretion," Journal of Pediatric Endocrinology & Metabolism, 18(4):325-338 (2005).

Supplementary European Search Report for European Application No. 12843460.2, mailed Feb. 25, 2015, 6 pages.

Dufner et al., "Base- and Sugar-Modified Cytidine Monophosphate N-Acetylneuraminic Acid (CMP-Neu5Ac) Analogues—Synthesis and Studies with α(2-6)-Sialyltransferase from Rat Liver," Eur. J. Org. Chem. 2000(8):1467-1482 (2000).

Liu et al., "Overproduction of CMP-Sialic Acid Synthetase for Organic Synthesis," J. Am. Chem. Soc. 114:3901-3910 (1992).

Martin et al., "The Synthesis and Enzymatic Incorporation of Sialic Acid Derivatives for use as Tools to Studay the Structure, Activity, and Inhibition of Glycoproteins and other Glycoconjugates," Bioorg. Med. Chem. 6:1283-1292 (1998).

"Fundamental Therapy Development of Distal Myopathy with Rimmed Vacuoles," Heisei 19 Soukatsu / Buntan Kenkyu Houkokusho, pp. 1-7 (2008).

Supplementary European Search Report for European Application No. 12843460.2, mailed Aug. 12, 2015, 14 pages.

Supplementary European Search Report for European Application No. 13739040.7, mailed Aug. 4, 2015, 8 pages.

Horn, E. J. et al., "Investigation into an efficient synthesis of 2,3-dehydro-N-acetyl neuraminic acid leads to three decarboxylated sialic acid dimers," Carbohydrate Research, 343(5):936-940 (2008).

Sato, S. et al., "Studies on sialic acids. XIV. Lactone derivatives of N-Acetylneuraminic acid," Chemical & Pharmaceutical Bulletin, 36(12):4678 (1988).

* cited by examiner

Particle Size Distribution of Un-sieved Sialic Acid

Particle Size distribution Plot for ProCR Sialic Acid, 250 Final Blends

Dissolution Plot of Sialic Acid 250 and 325mg SR Tablets by Direct Compression

Dissolution Profile of Sialic Acid 325 and 500 mg SR Tablets Uncoated

Dissolution Profile of Sialic Acid 325mg and 500mg SR Tablets (Coated), Initial Stability Dissolution Profile of ManNAc 325mg Tablets Individual Concentrations of Sialic Acid versus Time in Beagle Dog Serum Following IV or Oral Administration

METHODS AND FORMULATIONS FOR TREATING SIALIC ACID DEFICIENCIES

CROSS-REFERENCE TO RELATED APPLICATIONS

This application is a U.S. national stage application of International Application No. PCT/US2011/043910, which was filed on Jul. 13, 2011 and claims the priority benefit of U.S. Provisional Patent Application No. 61/363,995 filed on Jul. 13, 2010, the content of which is incorporated herein by reference in its entirety.

TECHNICAL FIELD

The present invention relates to extended release formulations and methods for treating sialic acid deficiencies.

BACKGROUND

Sialic acid is the only sugar that contains a net negative charge and is typically found on terminating branches of N-glycans, O-glycans, and glycosphingolipids (gangliosides) (and occasionally capping side chains of GPI anchors). The sialic acid modification of cell surface molecules is crucial for many biological phenomena including protein structure and stability, regulation of cell adhesion, and signal transduction. Sialic acid deficiency disorders such as Hereditary Inclusion Body Myopathy (HIBM or HIBM type 2), Nonaka myopathy, and Distal Myopathy with Rimmed Vacuoles (DMRV) are clinical diseases resulting from a reduction in sialic acid production.

HIBM is a rare autosomal recessive neuromuscular disorder caused by a specific biosynthetic defect in the sialic acid synthesis pathway. Eisenberg et al., *Nat. Genet.* 29:83-87 (2001). The disease usually manifests between the ages of 20 to 40 with foot drop and slowly progressive muscle weakness and atrophy. Patients may suffer difficulties walking with foot drop, gripping and using their hands, and normal body functions like swallowing. Histologically, it is associated with muscle fiber degeneration and formation of vacuoles containing 15-18 nm tubulofilaments that immunoreact like β-amyloid, ubiquitin, prion protein and other amyloid-related proteins. Askanas et al., *Curr Opin Rheumatol.* 10:530-542 (1998). Both the progressive weakness and histological changes initially spare the quadriceps and certain other muscles of the face. However, the disease is relentlessly progressive with patients becoming incapacitated and wheelchair-confined within two to three decades. There are no treatments currently available.

Studies of an Iranian-Jewish genetic isolate mapped the mutation associated with HIBM to chromosome 9p12-13. Argov et al., *Neurology* 60:1519-1523 (2003). The causative mutations were identified for HIBM in the gene GNE, which encodes the bifunctional enzyme UDP-N-acetylglucosamine-2-epimerase/N-acetylmannosamine kinase (GNE/MNK). Eisenberg et al., *Nat. Genet.* 29:83-87 (2001). DMRV is a Japanese variant, allelic to HIBM. Nishino et al., *Neurology* 59:1689-1693 (2002).

The biosynthesis steps and feedback regulation of GNE/MNK is depicted in FIG. 1. The production of sialic acid on glycoconjugates requires the conversion of N-acetylglucosamine (conjugated to its carrier nucleotide sugar UDP) to sialic acid. The sialic acid subsequently enters the nucleus where it is conjugated with its nucleotide sugar carrier CMP to make CMP-sialic acid, which is used as a donor sugar for glycosylation reactions in the cell. CMP-sialic acid is a known regulator of GNE/MNK activity. Jay et al., *Gene Reg. & Sys. Biol.* 3:181-190 (2009). Patients with HIBM have a deficiency in the production of sialic acid via the rate controlling enzyme GNE/MNK, which conducts the first two steps of this sequence: 1) epimerization of the glucosamine moiety to mannosamine with release of UDP, and 2) phosphorylation of the N-acetylmannosamine. The mutations causing HIBM occur in the regions encoding either the epimerase domain (GNE) or the kinase domain (MNK). Nearly twenty GNE mutations have been reported in HIBM patients from different ethnic backgrounds with founder effects among the Iranian Jews and Japanese. Broccolini et al., *Hum. Mutat.* 23:632 (2004). Most are missense mutations and result in decreased enzyme GNE activity and underproduction of sialic acid. Sparks et al., *Glycobiology* 15(11):1102-10 (2005); Penner et al., *Biochemistry* 45:2968-2977 (2006).

Knock-out of the GNE/MNK gene in mice is lethal as no sialic acid is incompatible with life, but knock-in introduction of human mutant forms of GNE/MNK have allowed the production of mouse models with human disease features. In the DMRV-HIBM mouse model in which Gne-deficient mice transgenically express the human GNE gene with D176V mutation (Gne$^{-/-}$ hGNED176V-Tg), these mice show hyposialylation in various organs in addition to the characteristic features of muscle atrophy, weakness and degeneration, and amyloid deposition. In these mice, hyposialylation is documented from birth, yet the mice only develop muscle symptoms several weeks later, including decreased twitch force production in isolated muscles starting at 10 weeks of age and impairment of motor performance from 20 weeks of age onward. Muscle atrophy and weakness were, however, reduced or prevented after treatment with administration of a sialic acid precursor N-acetylmannosamine (ManNAc), sialic acid, or sialyl-lactose, in water. Malicdan et al., *Nat. Medicine* 15(6):690-695 (2009). All three sialic acid metabolite tested showed similar treatment effects. In another mouse model of HIBM in which knockin mice harbor the M712T Gne/Mnk mutation, mice homozygous for the M712T Gne mutation died within 72 hours after birth, but lacked a muscle phenotype. Galeano et al., *J. Clin. Investigation* 117(6) 1585-1594 (2007). Homozygous mice, however, did have severe glomerular hematuria and podocytopathy, including effacement of the podocyte foot processes and segmental splitting of the glomerular basement membrane (GBM). Administration of ManNAc in water to mutant mice improved survival, improved renal histology including less flattened and fused podocyte foot processes, increased sialylation of renal podocalyxin, and increased sialylation of brain PSA-NCAM. Galeano et al., *J. Clin. Investigation* 117(6) 1585-1594 (2007).

Theoretically, the replacement of any metabolite after the genetic block in the pathway could alleviate symptoms of a sialic acid deficiency if the production of sialic acid is the key reason the mutation causes the disease. Jay et al., *Gene Reg. and Sys. Biology* 3:181-190 (2009). The challenge in administering a compound in the sialic acid biosynthetic pathway in vivo, however, is mainly its rapid clearance and excretion in the urine. After a single intraperitoneal injection of N-acetylneuraminic acid (NeuAc), the sialic acid concentration in the serum was considerably increased within minutes, but 90% of the sialic acid was found in the urine within 5-30 min, and almost all of it was excreted within 4 hours. After a single dose of NeuAc by the intragastric route, the sialic acid concentration in the serum was half that achieved by the intraperitoneal route, but the excretion rate was slower, as 70% of the sialic acid was found in the urine within 30-60 min. A similar pattern of rapid excretion was observed after a single dose of the physiological sialic acid precursor, ManNAc. Malicdan et al., *Nat. Medicine* 15(6): 690-695 (2009).

Treatment experiments by Galeano et al. and Malicdan et al. described above utilized exposure to the drug via water intake which provides a longer term exposure to drug than might be achieved by bolus or episodic treatment. Continuous treatment, such as continuous water-based exposure, is not reasonable or preferred in human treatment due in part to the logistics of performing it and the resulting difficulty with medication compliance.

Further, the treatment of sialic acid deficiencies is complicated by the fact that each individual may carry a different GNE mutation, which may affect either the epimerase domain (GNE) and/or kinase domain (MNK) of the enzyme and to varying degrees. The residual catalytic activity of the MNK might perform this function, but not in all patients. If ManNAc is administered to an individual who lacks most or all MNK activity, treatment will be dependent on unknown kinases or N-acetylglucosamine kinase to transform ManNAc to ManNAc-6-phosphate. The degree and quantity of these other kinase enzymes and their efficiency in transforming ManNAc to the phosphorylated form is unknown and will likely vary between people. This process may be slow or unpredictable and could delay or limit the onset of sialic acid production in some patients relative to giving sialic acid directly. ManNAc may have an advantage if its absorption into cells is improved due to its lack of charge. Its distribution to some tissues or in some people may be better than charged sialic acid if the variable kinase and metabolic steps as well as the rapid clearance are not limiting. ManNAc is a direct product of GNE/MNK and so may also act as a typical product inhibitor of the residual enzyme activity causing a decrease in endogenous production. This phenomenon may explain the very flat therapeutic effect curve showing that 20 mg/kg, 200 mg/kg and 2,000 mg/kg had very similar levels of efficacy which was still not completely effective in preventing disease in mouse DMRV model experiments. Malicdan et al., *Nat. Medicine* 15(6):690-695 (2009).

Sialic acid as treatment avoids the need for the random kinase phosphorylation of ManNAc and is more immediately available. Since it avoids the uncertainty of the kinase step, sialic acid may provide a better replacement efficacy if the genetics and phenotype of the patient make phosphorylation less efficient in a given individual and to minimize tissue-dependent phosphorylation variations. Sialic acid's action will likely be more immediate as it is near the end of the sialic acid biosynthetic pathway; however, sialic acid is also quickly cleared primarily by the kidneys. Therefore, sialic acid may have rapid-on and rapid-off effects. In addition, giving too much of sialic acid could result in a surge in CMP-sialic acid which could act as a potential feedback inhibitor of the GNE/MNK enzyme, which could have negative consequences on overall biosynthesis of sialic acid production and worsen symptoms of the sialic acid deficiency. Jay et al., *Gene Reg. and Sys. Biology* 3:181-190 (2009).

Effective replacement of substrate within the sialic biosynthetic pathway may require a more steady even exposure to non-inhibiting or regulating levels of sialic acid metabolites, while at the same time maintain an adequate pool of CMP-sialic acid for glycosylation reactions. Several data suggest that the production of CMP-sialic acid is highly regulated and that there is not a large pool of CMP sialic acid allowed to accumulate. The homology of mouse and human GNE/MNK is about 98% which is far above the normal levels of homology, suggesting very tight control of this enzyme's function. Seppala et al., *Am. J. Hum. Genet.* 64: 1563-1569 (1999). The allosteric regulation by CMP-sialic acid further suggests that the system is finely tuned to assure steady production of sialic acid and not excess production. Mutations in GNE/MNK that interfere with this regulation cause a disease called sialuria due to excess sialic acid production. Since sialic acid is prepared for attachment to biologicals as a high energy nucleotide carrier CMP, it is certainly expected that excess use of a high energy intermediate would not be optimal for the cell. Finally, data from pharmacokinetics and metabolism experiments suggest that very small percentages of administered sialic acid or ManNAc are incorporated into the body after a dose, and the vast majority is excreted and not stored. Given the lack of a significant pool, dietary sialic acid or mannosamine is insufficient to maintain glycosylation through the day and night. The muscle is most limited since its expression of GNE/MNK is very low compared to other tissues like the liver. Given the muscle phenotype of mutations, it is reasonable to assume that biosynthesis is tightly regulated to sialylation needs, and that no substantial pool exists in vivo. In this situation, effective delivery of CMP-sialic acid to the sites of glycosylation in the cell requires a steady and continuous exposure to assure that feedback regulation is not induced by spikes in concentration, and that glycosylation does not become deficient during periods of low substrate. This low period may be particularly problematic at night, when intake of sialic acid or metabolites is not occurring, and ⅔rds of the growth hormone and insulin-like growth factor 1 (IGF-1) is produced, which is critical for inducing muscle repair and anabolism. Frost and Lang Minerva, *Endocrinol.* 28:53-73 (2003); Wajnrajch J., *Pediatr. Endocrinol. Metab.* 18:325-338 (2005). Effective substrate replacement may require then continuous and steady provision of the metabolites to many tissues and be effective in a wide variety of patient types with different mutations.

Given the need for continuous exposure and the plasma half-lives of sialic acid biosynthetic pathway components, there is a need for formulations which provide extended exposure to sialic acid, reduce immediate surges in the metabolites of sialic acid, have general tissue availability, and are efficacious in individuals across a broad range of genotypes/phenotypes.

All publications and patent applications cited in this specification are incorporated herein by reference as if each individual publication or patent application were specifically and individually indicated to be incorporated by reference.

SUMMARY OF THE INVENTION

The present invention provides extended release pharmaceutical formulations comprising one or more compounds in the sialic acid biosynthetic pathway or derivative thereof.

In some embodiments of any of the extended release formulations, the extended release formulation comprises two compounds in the sialic acid biosynthetic pathway or derivative thereof. In some embodiments, the two compounds in the extended release formulations are in a weight to weight percent of about 50%:50%.

In some embodiments of any of the extended release formulations, the one or more compounds comprise N-acetyl mannosamine or a derivative thereof. In some embodiments, the one of more compounds comprise N-acetyl mannosamine. In some embodiments of any of the extended release formulations, the one of more compounds comprise sialic acid or a derivative thereof. In some embodiments, the one of more compounds comprise sialic acid.

In some embodiments of any of the extended release formulations, the one or more compounds comprise N-acetyl mannosamine or a derivative thereof and sialic acid or a derivative thereof. In some embodiments, the extended release formulation comprises N-acetyl mannosamine and sialic acid. In some embodiments, the N-acetyl mannosamine and sialic acid are in a weight to weight percent of about 50%:50%.

In some embodiments of any of the extended release formulations, the extended release formulation comprises one or more polymers selected from the group consisting of a) at least one water-swellable, pH independent polymer, b) at least one anionic, pH-dependent, gel-forming copolymer, c) at least one cationic polymer, and d) at least one hydrocolloid polymer.

In some embodiments of any of the extended release formulations, the extended release formulation is capable of delivering to an individual in need thereof a therapeutically effective amount of one or more compounds in the sialic acid pathway or derivatives thereof over a period of greater than about one hour. In some embodiments, the extended release formulation is capable of delivering to the individual in need thereof a therapeutically effective amount of one or more compounds in the sialic acid pathway or derivatives thereof over a period of over about 24 hours. In some embodiments, the extended release formulation is capable of delivering to the individual in need thereof a therapeutically effective amount of one or more compounds in the sialic acid pathway or derivatives thereof over a period of over about 12 hours. In some embodiments, the extended release formulation is sufficient to allow adequate replacement of sialic acid metabolites alone or in combination during the entire night or a complete sleep cycle during the period of peak muscle repair and anabolism.

In some embodiments of any of the extended release formulations, the extended release formulation is capable of delivering to the individual in need thereof one or more compounds in the sialic acid pathway or derivatives thereof with a $T_{max}$ of between about 2 hours and about 8 hours. In some embodiments, the extended release formulation is capable of delivering to the individual in need thereof one or more compounds in the sialic acid pathway or derivatives thereof with a $T_{max}$ of between about 3 hours and about 4 hours.

In some embodiments of any of the extended release formulations, the extended release formulation is capable of delivering to an individual in need thereof between about 0.1 g/day and about 50 g/day of one or more compounds in the sialic acid pathway or derivatives thereof. In some embodiments, the extended release formulation is capable of delivering to an individual in need thereof between about 1 g/day and about 5 g/day.

In some embodiments of any of the extended release formulations, the extended release formulation is capable of delivering to an individual in need thereof between about 0.01 mg/kg to about 750 mg/kg of one or more compounds in the sialic acid pathway or derivatives thereof. In some embodiments, the extended release formulation is capable of delivering to an individual in need thereof between about 5 mg/kg and about 50 mg/kg.

Provided herein are also method for treating a sialic acid deficiency in an individual in need thereof and/or preventing development of a sialic acid deficiency in an individual in need thereof comprising administering an effective amount of one or more compounds in the sialic acid pathway or derivatives thereof in the extended release formulation as described herein. Also provided are methods of making the extended release formulations detailed herein, unit dosages of the extended release formulations and kits and articles of manufacture comprising the extended release formulations. Oral dosage forms of the extended release formulations are also provided, such as solid or liquid dosage forms. Solid dosage forms of the extended release formulations are particularly provided, such as tablets or capsules.

In some embodiments of any of the methods, the sialic acid deficiency is a myopathy associated with sialic acid deficiency. In some embodiments, the myopathy associated with sialic acid deficiency is Hereditary Inclusion Body Myopathy (HIBM), Nonaka myopathy, and/or Distal Myopathy with Rimmed Vacuoles (DMRV).

An extended release pharmaceutical formulation comprising one or more compounds in the sialic acid biosynthetic pathway or derivative thereof (e.g., sialic acid and/or ManNAc or a pharmaceutically acceptable salt thereof) and one or more polymers selected from the group consisting of a) at least one water-swellable, pH independent polymer (e.g., hypromellose such as hypromellose type 2208 or Methocel K100M), b) at least one anionic, pH-dependent, gel-forming copolymer (alginate salt, such as sodium alginate), c) at least one cationic polymer, and d) at least one hydrocolloid polymer (e.g., carrageenan, such as lamda carrageenan) is provided. In one aspect, an extended release formulation comprises one or more compounds in the sialic acid biosynthetic pathway or derivative thereof (e.g., sialic acid and/or ManNAc or a pharmaceutically acceptable salt thereof); at least one anionic, pH-dependent, gel-forming copolymer (alginate salt, such as sodium alginate); at least one hydrocolloid polymer (e.g., carrageenan, such as lamda carrageenan); and at least one water-swellable, pH independent polymer (e.g., hypromellose such as hypromellose type 2208 or Methocel K100M) or cationic polymer. Such an extended release formulation may further comprise microcrystalline cellulose and silicon dioxide. Such an extended release formulation may further comprise magnesium stearate. Such an extended release formulation may further comprise microcrystalline cellulose, silicon dioxide and magnesium stearate. Such extended release formulations may further comprise an enteric coating. An extended release formulation may also exhibit any one or more of the following characteristics: (i) be capable of delivering to an individual in need thereof a therapeutically effective amount of one or more compounds in the sialic acid pathway or derivatives thereof over a period of greater than about one hour or over a period of greater than about 12 hours; (ii) be capable of delivering to the individual in need thereof a therapeutically effective amount of one or more compounds in the sialic acid pathway or derivatives thereof with a $T_{max}$ of between about 2 hours and about 8 hours; (iii) be capable of delivering to an individual in need thereof between about 0.1 g/day and about 50 g/day of one or more compounds in the sialic acid pathway or derivatives thereof; and (iv) be capable of delivering to an individual in need thereof between about 0.01 mg/kg to about 750 mg/kg of one or more compounds in the sialic acid pathway or derivatives thereof. In one aspect, the extended release formulations detailed herein are formulated for oral delivery to an individual (e.g., is formulated as a tablet or capsule). An extended release formulation as detailed herein may be used in a method for treating a sialic acid deficiency (e.g., myopathy associated with sialic acid deficiency such as any of Hereditary Inclusion Body Myopathy (HIBM), Nonaka myopathy, and/or Distal Myopathy with Rimmed Vacuoles (DMRV)) in an individual in need thereof comprising administering the individual an effective amount of the extended release formulation (e.g., an extended release formulation comprising an effective amount of a compound in the sialic acid pathway or derivatives thereof or salt of the foregoing, such as sialic acid or MaNAc). In a particular aspect, a method of treating a sialic acid deficiency (e.g., myopathy associated with sialic acid deficiency such as any of Hereditary Inclusion Body Myopathy (HIBM), Nonaka myopathy, and/or Distal Myopathy with Rimmed Vacuoles (DMRV)) in an individual in need thereof is provided, the method comprising administering the individual an effective amount of an extended release formulation comprising one or more compounds in the sialic acid biosynthetic pathway or derivative thereof (e.g., sialic acid and/or ManNAc or a pharmaceutically acceptable salt thereof) and one or more polymers selected from the group consisting of a) at least one water-swellable, pH independent polymer (e.g., hypromellose such as hypromellose type 2208 or Methocel K100M), b) at least one anionic, pH-dependent, gel-forming copolymer (alginate salt, such as sodium alginate), c) at least one cationic polymer, and d) at least one hydrocolloid polymer (e.g., carrageenan, such as lamda carrageenan) and optionally comprising microcrystalline cellulose, silicon dioxide and magnesium stearate. In a further aspect, a method of treating a sialic acid deficiency (e.g., myopathy associated with sialic acid deficiency such as any of Hereditary Inclusion Body Myopathy (HIBM), Nonaka myopathy, and/or Distal Myopathy with Rimmed Vacuoles (DMRV)) in an individual in need thereof is provided, the method comprising administering the individual an effective amount of an extended release formulation comprising one or more compounds in the sialic acid biosynthetic pathway or derivative thereof (e.g., sialic acid and/or ManNAc or a pharmaceutically acceptable salt thereof); at least one anionic, pH-dependent, gel-forming copolymer (alginate salt, such as sodium alginate); at least one hydrocolloid polymer (e.g., carrageenan, such as lamda carrageenan); and at least one water-swellable, pH independent polymer (e.g., hypromellose such as hypromellose type 2208 or Methocel K100M) or cationic polymer.

An extended release pharmaceutical formulation comprising one or more compounds in the sialic acid biosynthetic pathway or derivative thereof (e.g., sialic acid and/or ManNAc or a pharmaceutically acceptable salt thereof) and one or more polymers selected from the group consisting of a) at least one water-swellable, pH independent polymer (e.g., hypromellose such as hypromellose type 2208 or Methocel K100M), b) at least one anionic, pH-dependent, gel-forming copolymer (alginate salt, such as sodium alginate), c) at least one hydrogel (e.g., polyethylene oxide such as Polyox WSR), and d) at least one hydrocolloid polymer (e.g., carrageenan, such as lamda carrageenan) is provided. In one aspect, an extended release formulation comprises one or more compounds in the sialic acid biosynthetic pathway or derivative thereof (e.g., sialic acid and/or ManNAc or a pharmaceutically acceptable salt thereof); at least one anionic, pH-dependent, gel-forming copolymer (alginate salt, such as sodium alginate); at least one hydrocolloid polymer (e.g., carrageenan, such as lamda carrageenan); and at least one water-swellable, pH independent polymer (e.g., hypromellose such as hypromellose type 2208 or Methocel K100M) or hydrogel (e.g., polyethylene oxide such as Polyox WSR). An extended release formulation may further comprise microcrystalline cellulose and silicon dioxide. An extended release formulation may further comprise magnesium stearate. An extended release formulation may further comprise microcrystalline cellulose, silicon dioxide and magnesium stearate. Such extended release formulations may further comprise an enteric coating. An extended release formulation may also exhibit any one or more of the following characteristics: (i) be capable of delivering to an individual in need thereof a therapeutically effective amount of one or more compounds in the sialic acid pathway or derivatives thereof over a period of greater than about one hour or over a period of greater than about 12 hours; (ii) be capable of delivering to the individual in need thereof a therapeutically effective amount of one or more compounds in the sialic acid pathway or derivatives thereof with a $T_{max}$ of between about 2 hours and about 8 hours; (iii) capable of delivering to an individual in need thereof between about 0.1 g/day and about 50 g/day of one or more compounds in the sialic acid pathway or derivatives thereof; and (iv) capable of delivering to an individual in need thereof between about 0.01 mg/kg to about 750 mg/kg of one or more compounds in the sialic acid pathway or derivatives thereof. In one aspect, the extended release formulation is formulated for oral delivery to an individual (e.g., is formulated as a tablet or capsule). An extended release formulation may be used in a method for treating a sialic acid deficiency (e.g., myopathy associated with sialic acid deficiency such as any of Hereditary Inclusion Body Myopathy (HIBM), Nonaka myopathy, and/or Distal Myopathy with Rimmed Vacuoles (DMRV)) in an individual in need thereof comprising administering the individual an effective amount of the extended release formulation (e.g., an extended release formulation comprising an effective amount of a compound in the sialic acid pathway or derivatives thereof or salt of the foregoing, such as sialic acid or MaNAc). In a particular aspect, a method of treating a sialic acid deficiency (e.g., myopathy associated with sialic acid deficiency such as any of Hereditary Inclusion Body Myopathy (HIBM), Nonaka myopathy, and/or Distal Myopathy with Rimmed Vacuoles (DMRV)) in an individual in need thereof is provided, the method comprising administering the individual an effective amount of an extended release formulation comprising one or more compounds in the sialic acid biosynthetic pathway or derivative thereof (e.g., sialic acid and/or ManNAc or a pharmaceutically acceptable salt thereof) and one or more polymers selected from the group consisting of a) at least one water-swellable, pH independent polymer (e.g., hypromellose such as hypromellose type 2208 or Methocel K100M), b) at least one anionic, pH-dependent, gel-forming copolymer (alginate salt, such as sodium alginate), c) at least one hydrogel (e.g., polyethylene oxide such as Polyox WSR), and d) at least one hydrocolloid polymer (e.g., carrageenan, such as lamda carrageenan) and optionally comprising microcrystalline cellulose, silicon dioxide and magnesium stearate. In a further aspect, a method of treating a sialic acid deficiency (e.g., myopathy associated with sialic acid deficiency such as any of Hereditary Inclusion Body Myopathy (HIBM), Nonaka myopathy, and/or Distal Myopathy with Rimmed Vacuoles (DMRV)) in an individual in need thereof is provided, the method comprising administering the individual an effective amount of an extended release formulation comprising one or more compounds in the sialic acid biosynthetic pathway or derivative thereof (e.g., sialic acid and/or ManNAc or a pharmaceutically acceptable salt thereof); at least one anionic, pH-dependent, gel-forming copolymer (alginate salt, such as sodium alginate); at least one hydrocolloid polymer (e.g., carrageenan, such as lamda carrageenan); and at least one water-swellable, pH independent polymer (e.g., hypromellose such as hypromellose type 2208 or Methocel K100M) or hydrogel (e.g., polyethylene oxide such as Polyox WSR).

In another variation, a method of treating a sialic acid deficiency (e.g., myopathy associated with sialic acid deficiency such as any of Hereditary Inclusion Body Myopathy (HIBM), Nonaka myopathy, and/or Distal Myopathy with Rimmed Vacuoles (DMRV)) in an individual in need thereof is provided, the method comprising administering the individual an effective amount of an extended release formulation comprising sialic acid, or a pharmaceutically acceptable salt thereof, as the therapeutic agent. In another variation, the extended release formulation for use in the methods detailed herein comprises MaNAc, or a pharmaceutically acceptable salt thereof, as the therapeutic agent. In another variation, the extended release formulation for use in the methods detailed herein comprises sialic acid, or a pharmaceutically acceptable salt thereof and MaNAc, or a pharmaceutically acceptable salt thereof, as the therapeutic agents. In another variation, the extended release formulation for use in the methods detailed herein comprises a prodrug of one or more compounds in the sialic acid biosynthetic pathway such as a prodrug of sialic acid, or a pharmaceutically acceptable salt thereof, as the therapeutic agent. In another variation, the extended release formulation for use in the methods detailed herein comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation for use in the methods detailed herein comprises sialic acid, or a pharmaceutically acceptable salt thereof, carrageenan, sodium alginate and either hypromellose or polyethylene oxide. In a further variation, the extended release formulation for use in the methods detailed herein comprises sialic acid, or a pharmaceutically acceptable salt thereof, carrageenan, sodium alginate, either hypromellose or polyethylene oxide, magnesium strearate and microcrystalline colluloce and colloiddal silicon dioxide. In one aspect, the extended release formulation for use in the methods detailed herein is a formulation of Table E. In yet another aspect, the extended release formulation for use in the methods detailed herein is a formulation of Table 8.

DETAILED DESCRIPTION

Figure 1:
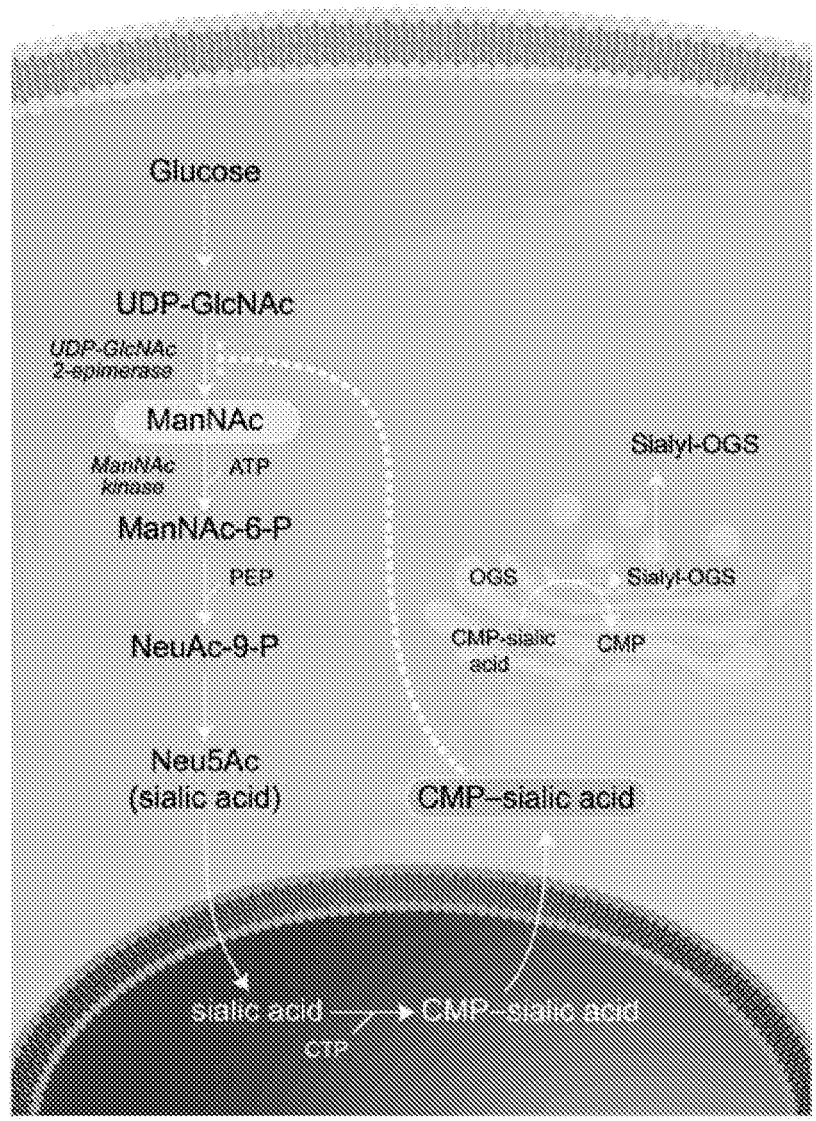
FIG. 1 provides a diagram of intracellular sialic acid metabolism.

The present application provides extended release pharmaceutical formulations comprising one or more compounds in the sialic acid biosynthetic pathway or derivative thereof and methods of treating and preventing sialic acid deficiencies utilizing the extended release pharmaceutical formulations. This invention concerns designing an approach to substrate replacement that provides individuals with sialic acid deficiencies stable and steady day and nighttime replacement without high concentration spikes across a broad range of genotypes and in multiple tissues. This invention can optimally achieve this substrate replacement and treatment benefit through the combination of using extended release formulations and one or more metabolites, including combinations of metabolites.

It is understood that the description refers to and includes effective amounts of an active agent, such as the compounds provided herein, which include but are not limited to the compounds included under the heading "Therapeutic Agent." Thus, it is understood that any of the extended release formulations detailed herein may comprise an effective amount of a therapeutic agent, such as an effective amount of sialic acid, or a pharmaceutically acceptable salt thereof.

DEFINITIONS

The terms "oral administration" and "oral ingestion" refer to all conventional forms for the oral delivery of a pharmaceutical composition to an individual and that result in the deposition of the pharmaceutical formulation into the gastrointestinal tract (including the gastro portion of the gastrointestinal tract, i.e., the stomach) of the patient. Accordingly, oral administration and oral ingestion include, by way of example, actual ingestion of a solid or liquid pharmaceutical composition, oral gavage, and the like.

The terms "treating" and "treatment" as used herein refer to an approach for obtaining beneficial or desired results including clinical results. For purposes of this invention, beneficial or desired clinical results include, but are not limited to, one or more of the following: decreasing the severity and/or frequency one or more symptoms resulting from the disease, diminishing the extent of the disease, stabilizing the disease (e.g., preventing or delaying the worsening of the disease), delay or slowing the progression of the disease, ameliorating the disease state, increasing production of sialic acid, the sialylation precursor CMP-sialic acid (e.g., increasing intracellular production of sialic acid) and restoring the level of sialylation in muscle and other proteins, decreasing the dose of one or more other medications required to treat the disease, and/or increasing the quality of life. "Treating" a patient with a formulation described herein includes management of an individual to inhibit or cause regression of a disease or condition.

"Prophylaxis" or "prophylactic treatment" "or preventive treatment" refers to prevention of the occurrence of symptoms and/or their underlying cause, for example, prevention of a disease or condition in a patient susceptible to developing a disease or condition (e.g., at a higher risk, as a result of genetic predisposition, environmental factors, predisposing diseases or disorders, or the like). Prophylaxis includes HIBM myopathy in which chronic disease changes in the muscles are irreversible and for which animal model data suggests treatment benefit in prophylaxis.

As used herein, "delaying" the progression of the disease means to defer, hinder, slow, retard, stabilize, and/or postpone development of the disease. This delay can be of varying lengths of time, depending on the history of the disease and/or individual being treated.

As used herein, an "at risk" individual is an individual who is at risk of developing a sialic acid deficiency. An individual "at risk" may or may not have detectable disease, and may or may not have displayed detectable disease prior to the treatment methods described herein. "At risk" denotes that an individual has one or more so-called risk factors, which are measurable parameters that correlate with development of a sialic acid deficiency, which are described herein. An individual having one or more of these risk factors has a higher probability of developing a sialic acid deficiency than an individual without these risk factor(s).

The term "effective amount" refers to the amount of a pharmaceutical formulation including one or more compounds in the sialic acid biosynthetic pathway that provides the one or more compounds in the sialic acid biosynthetic pathway in a sufficient amount to render a desired treatment outcome. An effective amount may be comprised within one or more doses, i.e., a single dose or multiple doses may be required to achieve the desired treatment endpoint.

A "therapeutically effective amount" refers to an amount of a pharmaceutical formulation including one or more compounds in the sialic acid biosynthetic pathway sufficient to produce a desired therapeutic outcome (e.g., reduction of severity of a disease or condition). A "prophylactically effective amount" refers to an amount of a pharmaceutical formulation including one or more compounds in the sialic acid biosynthetic pathway sufficient to prevent or reduce severity of a future disease or condition when administered to an individual who is susceptible and/or who may develop a disease or condition.

The term "extended release" refers to a drug-containing formulation or fraction thereof, in which release of the drug is not immediate, i.e., with an "extended release" formulation, administration does not result in immediate release of the drug into an absorption pool. In general, the term "extended release" as used herein includes controlled release, sustained release, and delayed release formulations.

By "pharmaceutically acceptable" is meant a material that is not biologically or otherwise undesirable, i.e., the material may be incorporated into a pharmaceutical composition administered to a patient without causing any significant undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

The term "disorder" or "disease" used interchangeably herein, refers to any alteration in the state of the body or one of its organs and/or tissues, interrupting or disturbing the performance of organ function and/or tissue function (e.g., causes organ dysfunction) and/or causing a symptom such as discomfort, dysfunction, distress, or even death to a subject afflicted with the disease.

The term "individual" refers to an animal, for example, a mammal and includes, but is not limited to, human, bovine, horse, feline, canine, rodent, or primate. Preferably, the individual is a human.

The term "derivative" as used herein includes derivatives, analogs, prodrugs, and unnatural precursors.

The term "pharmaceutically acceptable salt" refers to a salt which retains the biological effectiveness of the compound and which is not biologically or otherwise undesirable.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that embodiments, aspects and variations of the invention described herein include "comprising," "consisting" and/or "consisting essentially of" embodiments, aspects and variations.

Extended Release Formulations

Provided herein are extended release pharmaceutical formulations comprising as the therapeutic agent one or more compounds in the sialic acid biosynthetic pathway or a derivative thereof or a pharmaceutically acceptable salt of the foregoing. In one embodiment, the extended release pharmaceutical formulations comprise a therapeutic agent as detailed herein and a polymer. An extended release formulation comprising a therapeutic agent and a polymer may further comprise one or more additional components, such as any one or more of a diluent, an excipient, an antioxidant, a lubricant, a colorant, a binder, a disintegrant, and the like. It is understood that reference to and description of extended release pharmaceutical formulations comprising one or more compounds in the sialic acid biosynthetic pathway or a derivative thereof below is exemplary and that this description applies equally to and includes extended release pharmaceutical formulations comprising any one or more compounds in the sialic acid biosynthetic pathway. It is also understood that reference to and description of extended release pharmaceutical formulations comprising any one or more derivatives of compounds in the sialic acid biosynthetic pathway below is exemplary and that this description applies equally to and includes extended release pharmaceutical formulations comprising any one or more derivatives, analogs, prodrugs, and/or unnatural precursor compounds in the sialic acid biosynthetic pathway.

In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium strearate and microcrystalline collulose and colloiddal silicon dioxide. In one aspect, the extended release formulation is a formulation of Table E. In yet another aspect, the extended release formulation is a formulation of Table 8.

Therapeutic Agent

It is believed that administration of sialic acid or a compound in the sialic acid biosynthetic pathway, or a derivative thereof, or a pharmaceutically acceptable salt of any of the foregoing, may be administered as a therapeutic agent (e.g., as substrate replacement) to an individual who has or is suspected of having a sialic acid deficiency disorder. Extended release formulations comprising such compounds, or pharmaceutically acceptable salts thereof, as the therapeutic agent are provided herein. In one aspect, the sialic acid or a compound in the sialic acid biosynthetic pathway, or a derivative thereof, or a pharmaceutically acceptable salt of any of the foregoing, is sialic acid or a pharmaceutically acceptable salt thereof. In one aspect, any of the extended release formulations detailed herein may comprise an effective amount of a therapeutic agent, such as an effective amount of sialic acid or a pharmaceutically acceptable salt thereof.

A compound in the sialic acid biosynthetic pathway or a derivative thereof in one variation is a compound, or pharmaceutically acceptable salt thereof, that is at or downstream from ManNAc in the sialic acid biosynthetic pathway. In a particular variation, the therapeutic agent is a compound, or pharmaceutically acceptable salt thereof, that is at or downstream from ManNAc in the sialic acid biosynthetic pathway and is depicted in FIG. 1.

A compound in the sialic acid biosynthetic pathway or a derivative thereof in another variation is a compound, or a pharmaceutically acceptable salt thereof, that is at or upstream from CMP-sialic acid in the sialic acid biosynthetic pathway. In a particular variation, the therapeutic agent is a compound, or a pharmaceutically acceptable salt thereof, that is at or upstream from CMP-sialic acid in the sialic acid biosynthetic pathway and is depicted in FIG. 1. In one such variation, the compound in the sialic acid biosynthetic pathway or a derivative thereof does not include glucose or a pharmaceutically acceptable salt thereof.

In a particular variation, the compound in the sialic acid biosynthetic pathway or a derivative thereof in one variation is a compound, or a pharmaceutically acceptable salt thereof, that is: (i) at or downstream from ManNAc in the sialic acid biosynthetic pathway, and (ii) is at or upstream from CMP-sialic acid in the sialic acid biosynthetic pathway. In one such variation, the compound is a compound depicted in FIG. 1, or a pharmaceutically acceptable salt thereof.

A compound in the sialic acid biosynthetic pathway or derivative thereof includes, but is not limited to, mannosamine, N-acetyl mannosamine (ManNAc), ManNac-6-phosphate (ManNAc-6-P), UDP-GlcNAc, N-acetylneuraminic acid (NeuAc), NeuAc-9-phosphate (NeuAc-9-P), sialic acid (i.e., 5-N-acetylneuraminic acid), CMP-sialic acid, and/or derivatives thereof or pharmaceutically acceptable salts of the foregoing.

In some embodiments, the one or more compounds in the sialic acid biosynthetic pathway or derivative thereof include N-acetylneuraminic acid (NeuAc) or a derivative thereof. Structures of such NeuAc or derivatives thereof include, but are not limited to, those defined by the formula below:

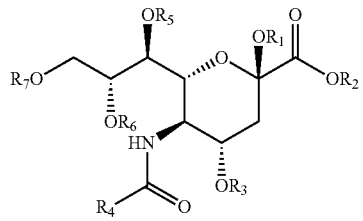

wherein each $R_1$, $R_2$, $R_3$, $R_5$, $R_6$, or $R_7$ is independently hydrogen, lower alkanoyl, carboxylate or lower alkyl; and $R_4$ is lower alkyl, lower alkanoylalkyl or lower alkyl alkanoyloxy.

In some embodiments, the one or more compounds in the sialic acid biosynthetic pathway or derivative thereof include ManNAc or a derivative thereof. Structures of such ManNAc and derivatives thereof include, but are not limited to, those defined by the formula below:

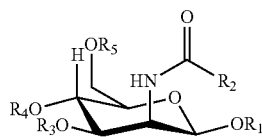

Wherein each $R_1$, $R_3$, $R_4$, or $R_5$ is independently hydrogen, lower alkanoyl, carboxylate or lower alkyl; and $R_2$ is lower alkyl, lower alkanoylalkyl or lower alkyl alkanoyloxy.

The term lower alkyl refers to ($C_1$-$C_6$)alkyl. A lower alkyl includes methyl, ethyl, propyl, isopropyl, butyl, iso-butyl, sec-butyl, pentyl, 3-pentyl, hexyl as well as ($C_3$-$C_6$)cycloalkyl moieties (e.g., cyclopropyl, cyclobutyl, cyclopentyl, or cyclohexyl), ($C_3$-$C_6$)cycloalkyl($C_1$-$C_6$)alkyl (e.g., cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl), ($C_1$-$C_6$)alkoxy (e.g., methoxy, ethoxy, propoxy, isopropoxy, butoxy, iso-butoxy, sec-butoxy, pentoxy, 3-pentoxy, or hexyloxy) ($C_2$-$C_6$)alkenyl (e.g., vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl), ($C_2$-$C_6$)alkynyl (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl), ($C_1$-$C_6$) alkanoyl (e.g., acetyl, propanoyl or butanoyl), halo($C_1$-$C_6$) alkyl (e.g., iodomethyl, bromomethyl, chloromethyl, fluoromethyl, trifluoromethyl, 2-chloroethyl, 2-fluoroethyl, 2,2,2-trifluoroethyl, or pentafluoroethyl), hydroxy($C_1$-$C_6$)alkyl (e.g., hydroxymethyl, 1-hydroxyethyl, 2-hydroxyethyl, 1-hydroxypropyl, 2-hydroxypropyl, 3-hydroxypropyl, 1-hydroxy butyl, 4-hydroxybutyl, 1-hydroxypentyl, 5-hydroxypentyl, 1-hydroxyhexyl, or 6-hydroxyhexyl), ($C_1$-$C_6$) alkoxycarbonyl (e.g., methoxycarbonyl, ethoxycarbonyl, propoxycarbonyl, isopropoxycarbonyl, butoxycarbonyl, pentoxycarbonyl, or hexyloxycarbonyl), ($C_1$-$C_6$)alkylthio (e.g., methylthio, ethylthio, propylthio, isopropylthio, butylthio, isobutylthio, pentylthio, or hexylthio), and/or ($C_2$-$C_6$) alkanoyloxy (e.g., acetoxy, propanoyloxy, butanoyloxy, isobutanoyloxy, pentanoyloxy, or hexanoyloxy).

In some embodiments, $R_2$ is methyl, and each of $R_1$, $R_3$, $R_4$, and $R_5$ is hydrogen. In some embodiments, the ManNAc or derivative thereof is N-acetyl mannosamine (ManNAc).

In some embodiments, the ManNAc or derivative thereof is N-levulinoylmannosamine (ManLev) or N-azidoacetylmannosamine (ManNAz).

In one variation, the one or more compounds in the sialic acid biosynthetic pathway or derivative thereof is an ester of a compound in the sialic acid biosynthetic pathway. In one aspect, the one or more compounds in the sialic acid biosynthetic pathway or derivative thereof is an ester of sialic acid or MaNAc. In a particular variation, the one or more compounds in the sialic acid biosynthetic pathway or derivative thereof is an ester of sialic acid. In one aspect, the one or more compounds in the sialic acid biosynthetic pathway or derivative thereof is a prodrug of sialic acid. See also WO 2010/131712, published Nov. 18, 2010, for derivatives of compounds in the sialic acid biosynthetic pathway, which is incorporated herein by reference in its entirety and specifically with respect to compounds (e.g., derivatives of compounds in the sialic acid biosynthetic pathway) detailed therein.

In one aspect, a derivative of one or more compounds in the sialic acid biosynthetic pathway (e.g., a derivative of sialic acid or MaNAc) is an effective substrate replacement for sialic acid, such as in an individual who has or is suspected of having a sialic acid deficiency disorder. A derivative of one or more compounds in the sialic acid biosynthetic pathway (e.g., a derivative of sialic acid or MaNAc), or an extended release formulation comprising a derivative of one or more compounds in the sialic acid biosynthetic pathway (e.g., a derivative of sialic acid or MaNAc) may exhibit any one or more of the following characteristics: (i) capable of delivering to an individual in need thereof a therapeutically effective amount of one or more compounds in the sialic acid pathway or derivatives thereof over a period of greater than about any of 1, 2, 3, 4, 5, 6, 7, 8, 9, 10, 11, 12, 13, 14, 15, 16, 17, 18, 19, 20, 21, 22, 23, or 24 hours; (ii) capable of delivering to an individual in need thereof a substantially constant therapeutically effective amount of one or more compounds in the sialic acid pathway or derivatives thereof over a period of greater than about any of 1, 2, 3, 4, 5, 6, 7, 8, 9, 10, 11, 12, 13, 14, 15, 16, 17, 18, 19, 20, 21, 22, 23, or 24 hours; (iii) capable of delivering to an individual in need thereof a therapeutically effective amount of one or more compounds in the sialic acid pathway or derivatives thereof with a $T_{max}$ of between about any of 2-4 hours, 3-4 hours, 6-8 hours, 6-12 hours, 6-15 hours, 12-18 hours, or 18-24 hours; (iv) capable of delivering to an individual in need thereof a therapeutically effective amount of one or more compounds in the sialic acid pathway or derivatives thereof with a $C_{max}$ of about 0.5-100 μg/mL; (v) capable of delivering to an individual in need thereof a therapeutically effective amount of one or more compounds in the sialic acid pathway or derivatives thereof with a trough level of about 0.1-20 μg/mL; (vi) capable of delivering to an individual in need thereof a therapeutically effective amount of one or more compounds in the sialic acid pathway or derivatives thereof with less than about any of 10%, 20%, 30%, 40%, 50%, 60%, or 70% excreted after one hour; (vii) capable of delivering to an individual in need thereof between about any of 0.01-750 mg/kg/day, 0.5-500 mg/kg/day, 1-250 mg/kg/day, 2.5-100 mg/kg/day, or 5-50 mg/kg/day of one or more compounds in the sialic acid pathway or derivatives thereof or a pharmaceutically acceptable salt of the foregoing; (viii) capable of delivering to an individual in need thereof between about any of 0.01-750 mg/kg/day, 0.5-500 mg/kg/day, 1-250 mg/kg/day, 2.5-100 mg/kg/day, or 5-50 mg/kg/day of one or more compounds in the sialic acid pathway or derivatives thereof or a pharmaceutically acceptable salt of the foregoing; (ix) has an absolute bioavailability of about 1 to about 50%; (x) has a bioavailability based on sialic acid levels in the urine of about 0.5 to about 100%; and (xi) has a mean residence time (MRT) of at least about 3.5 hours.

In some embodiments, the one or more compounds in the sialic acid biosynthetic pathway or derivative thereof include sialic acid or a derivative thereof. In some embodiments, the sialic acid or derivative thereof is sialic acid. In some embodiments, the sialic acid or derivative thereof is a sialic acid analog such as N-levulinoyl sialic acid (SiaLev) or N-azidoacetyl sialic acid (SiaNAz). In some embodiments, the sialic acid is bound as a glycoconjugate. In some embodiments, the sialic acid or derivative thereof is an unnatural precursor such as sialyllactose.

In some embodiments, the extended release formulation comprises about any of one, two, three, or four compounds in the sialic acid biosynthetic pathway or a derivative thereof. In some embodiments, the extended release formulation comprises two compounds in the sialic acid biosynthetic pathway or a derivative thereof. Therefore, for example, the extended release formulation may include ManNAc or a derivative thereof and sialic acid or a derivative thereof. More particularly, the extended release formulation may include ManNAc and sialic acid.

In embodiments of any of the extended release formulations, the amount of one or more compounds in the sialic acid biosynthetic pathway or derivative thereof in the extended release formulation is an amount effective to increase sialic acid production and/or increase sialylation (e.g., maximal restoration of sialylation).

The ratio of the two or more compounds in the sialic acid biosynthetic pathway or derivative thereof, in some embodiments, is a ratio which minimizes feedback inhibition of the sialic acid biosynthetic pathway. In some embodiments, the ratio of the two or more compounds in the sialic acid biosynthetic pathway or derivative thereof is a ratio which allows efficient delivery of the two or more compounds in the sialic acid biosynthetic pathway or derivative thereof to muscle cells. In some embodiments, the ratio of the two or more compounds in the sialic acid biosynthetic pathway or derivative thereof is a ratio which minimizes feedback inhibition of the sialic acid biosynthetic pathway and allows efficient delivery of the two or more compounds in the sialic acid biosynthetic pathway or derivative thereof to muscle cells. In some embodiments, the two or more compounds in the sialic acid biosynthetic pathway or derivative there of are ManNAc or a derivative thereof and sialic acid or a derivative thereof. For example, in some embodiments, the ratio of ManNAc and sialic acid is a ratio which minimizes feedback inhibition of the sialic acid biosynthetic pathway and allows efficient delivery of ManNAc and/or sialic acid to muscle cells. The combination may optimally spread out the replacement of intermediates, enhancing optimal distribution to all cell types with different metabolisms. Methods of testing restoration of sialylation and determining the best ratio of the two or more compounds in the sialic acid biosynthetic pathway or derivative thereof using in vitro HIBM muscle cells are known in the art. See e.g., Noguchi S. et al., *J. Bio. Chem.* 279(12):11402-7 (2004). This may involve evaluating muscle derived proteins for optimal sialylation such as soluble forms of neural cell adhesion molecule (NCAM) (Ricci et al., *Neurology* 66:755-758 (2006), evaluating sialic metabolite or CMP-sialic acid levels in tissue samples, or assessing sialylated proteins on the surface of muscle or other cells. Noguchi S. et al., *J. Bio. Chem.* 279(12):11402-7 (2004).

In embodiments in which the extended release formulation comprises two compounds in the sialic acid biosynthetic pathway or a derivative thereof, the two compounds in the extended release formulation may be present in a weight to weight percentage of between about any of 5%-95%:95%-5%, 5%-50%:95%-50%, or 10%-40%:90%-60%. The two compounds in the extended release formulation may be present in a weight to weight percentage of about any of 90%:10%, 80%:20%, 70%:30%, 60%:40%, 50%:50%, 40%:60%, 30%:70%, 20%:80%, or 10%:90%. In some embodiments, the two compounds in the extended release formulation are in a weight to weight percent of about 50%:50%. In some embodiments, the one or more compounds in the sialic acid pathway or derivatives thereof include ManNAc or a derivative thereof and/or sialic acid or a derivative thereof. Therefore, for example, the extended release formulation may include ManNAc and sialic acid wherein the weight to weight percentage of ManNAc to sialic acid is about any of 90%:10%, 80%:20%, 70%:30%, 60%:40%, 50%:50%, 40%:60%, 30%:70%, 20%:80%, or 10%:90%.

Polymer

The extended release formulations comprising one or more compounds in the sialic acid biosynthetic pathway or a derivative thereof as described herein may include one or more polymers. The polymer may be a natural polymer (e.g., polysaccharide or protein), modified natural polymer, and/or synthetic polymer. The polymer may be, for example, a hydrophobic polymer, hydrophilic polymer, hydrogel, soluble polymer, biodegradable polymer, nonbiodegradable polymer, and/or mucoadhesive polymer.

In some embodiments, the polymer is a hydrophobic polymer. Examples of hydrophobic polymers include polyethylene, polyvinyl chloride, ethyl cellulose or acrylate polymers and their copolymers.

In some embodiments, the polymer is a hydrophilic polymer. Examples of hydrophilic polymers include a) cellulose derivatives such as methylcellulose (MC), hydroxyethyl-cellulose, hydroxypropylmethyl-cellulose (HPMC), or sodium carboxymethylcellulose, b) noncellulose natural or semisynthetic polymers such as agar-agar, carob gum, alginates, molasses, polysaccharides of mannose and galactose, or chitosan and modified starches and c) polymers of acrylic acid such as carbopol polymers.

In some embodiments, the polymer is a hydrogel. Examples of hydrogels include, but are not limited to, polyhydroxyethyle methylacrylate (PHEMA), polyvinyl alcohol (PVA), polyvinyl pyrrolidone (PVP), polyethylene oxide (PEO), or polyacrylamide (PA). In some embodiments, the hydrogel is polyethylene oxide (e.g., Polyox™ water soluble resin, Dow Chemical Company, Mich., USA).

In some embodiments, the polymer is a soluble polymer. Examples of soluble polymers include, but are not limited to, polyethylene glycol (PEG), PVA, PVP, or HPMC.

In some embodiments, the polymer is a biodegradable polymer. Examples of biodegradable polymers include, but are not limited to, polylactic acid (PLA), polyglycolic acid (PGA), poly(lactic/glycolic acid) (PLGA), polycaprolactone (PCL), polyanhydrides, or polyorthoesters.

In some embodiments, the polymer is a nonbiodegradable polymer. Examples of nonbiodegradable polymers include, but are not limited to, polyethylene vinyl acetate, polydimethyl siloxane (PDS), polyether urethane (PEU), polyvinyl chloride (PVC), cellulose acetate (CA), or ethyl cellulose (EC).

In some embodiments, the polymer is a mucoadhesive polymer. Examples of mucoadhesive polymers include, but are not limited to, polycarbophil, sodium carboxymethyl cellulose, polyacrylic acid, tragacanth, methyl cellulose, pectin, natural gums, xanthan gum, guar gum, or karaya gum.

In some embodiments, the extended release pharmaceutical formulation includes two polymers. In some embodiments, the polymer is not polylactide. In some embodiments, the polymer is not a polylactide copolymer such as PLGA.

In some embodiments, the extended release formulation comprises one or more polymers selected from the group consisting of a) a water-swellable, pH independent polymer, b) a anionic, pH-dependent, gel-forming copolymer, c) a cationic polymer, and d) a hydrocolloid polymer. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium strearate and microcrystalline collulose and colloiddal silicon dioxide. In one aspect, the extended release formulation is a formulation of Table E. In yet another aspect, the extended release formulation is a formulation of Table 8.

Examples of a water-swellable, pH independent polymer include, but are not limited to, carbohydrate-based polymers such as, for example, hypromellose (formerly known as the family of hydroxypropyl methylcellulose), hydroxypropyl ethyl celluloses, hydroxypropyl cellulose, hydroxyethyl cellulose, methyl cellulose or other constituents Grades of these hypromellose copolymers typically used with the present invention include the E and K series such as for example, Dow Chemical Company's (Midland, Mich. USA) or Aqualon's (with a North American presence in Wilmington, Del.) E4M, E10M, K100LV, K4M, K15M, K25M, K100M, K200M and mixtures of various molecular weights and grades. Grades of hydroxyethyl cellulose include, for example, Aqualon's Natrasol polymers HHX (mol. Wt. 1,300,000), HX (mol. wt. 1,000,000), H (mol. wt. 1,000,000), M (mol. wt. 720,000 and G (mol. wt. 1,150,000), and mixtures thereof. Grades of hydroxypropyl cellulose include, for example, Aqualon's HPC polymers MF and MXF (mol. wt. 580,000) and KF and HXF (mol. wt. 1,150,000), and mixtures thereof. Grades and ethyl cellulose include, for example, Dow Chemical Company's Ethocel polymers 7FP, 10FP and 100FP and Aqualon's polymers T10EC, N7, N10, N17, N22, N50, N100 and N200, and mixtures thereof. In some embodiments, the water-swellable, pH independent polymer is hypromellose (e.g., hypromellose Type 2208). In some embodiments, the water-swellable, pH independent polymer is Methocel® (e.g., Methocel® K100MPremium CR, Colorcon).

Examples of anionic, pH-dependent, gel-forming copolymer include, but are not limited to, mono-valent alginate salt such as sodium, potassium or ammonium alginate salts, or combinations thereof, and sodium carboxymethyl cellulose and the like, or mixtures of one or more alginate salt and carboxymethyl cellulose and the like. In some embodiments, the anionic, pH-dependent, gel-forming copolymer is sodium alginate (e.g., Protanal®, FMC BioPolymer).

Examples of a cationic polymer include, for example, chitosan or a derivative thereof including, for example, trimethylchitosan and quarternised chitosan, and chitosan-derived materials including, for example, those taught in U.S. Pat. No. 5,747,475. Either high or low molecular weight chitosan products can be used in the pharmaceutical formulations of the present invention and are readily available in pharmaceutical grade from suppliers located worldwide.

The hydrocolloid polymer used in the formulations of the present invention can be carrageenan. Carrageenans are available as iota, kappa and lambda carrageenans, with iota being used most frequently used and lambda being used least frequently. Various salt forms of carrageenans are also available including, for example sodium carrageenan. Typically used grades of iota carrageenan include, without limitation, carrageenan NF AEP brand colloids (Hadley, N.Y. USA) FD433 (1% viscosity; 300-400 cps) and FD384 (1% viscosity; about 100 cps). Viscosity of other carrageenan products ranges from about 50 to about 4000 cps. In some embodiments, the carrageenan is lambda carrageenan (e.g., Viscarin GP-209, FMC BioPolymer). In some embodiments, the carrageenan has a viscosity of about 1500-2000 cPs. In some embodiments, the carrageenan has a viscosity of about 1600 cPs.

The formulation and polymers useful in the extended release formulation are further described in U.S. Patent Application 2010/0160363, published on Jun. 24, 2010, and U.S. Patent Application 2010/0159001, published Jun. 24, 2010, which are incorporated herein by reference in their entireties and specifically with respect to the polymers provided therein.

In some embodiments, the extended release formulation comprises a water-swellable, pH independent polymer (e.g., hypromellose). In some embodiments, the extended release formulation further comprises an anionic, pH-dependent, gel-forming copolymer (e.g., an alginate salt). In some embodiments, the extended release formulation further comprises a hydrocolloid polymer (e.g., carrageenan). In some embodiments, the extended release formulation comprises a water-swellable, pH independent polymer (e.g. hypromellose), an anionic, pH-dependent, gel-forming copolymer (e.g., an alginate salt) and a hydrocolloid polymer (e.g., a carrageenan). In some embodiments, the extended release formulation comprises hypromellose (e.g. hypromellose Type 2208 or Methocel K100M), sodium alginate (e.g. Protanal) and a lamda carrageenan (e.g. Viscarin GP-209). In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium strearate and microcrystalline collulose and colloiddal silicon dioxide. In one aspect, the extended release formulation is a formulation of Table E. In yet another aspect, the extended release formulation is a formulation of Table 8.

In some embodiments, the extended release formulation comprises a hydrogel (e.g., a polyethylene oxide). In some embodiments, the extended release formulation further comprises an anionic, pH-dependent, gel-forming copolymer (e.g. an alginate salt). In some embodiments, the extended release formulation further comprises a hydrochollold polymer (e.g., carrageenan). In some embodiments, the extended release formulation comprises a hydrogel (e.g., a polyethylene oxide), an anionic, pH-dependent, gel-forming copolymer (e.g., an alginate salt) and a hydrochollold polymer (e.g., a carrageenan). In some embodiments, the extended release formulation comprises polyethylene oxide (e.g. Polyox WSR), sodium alginate (e.g. Protanal) and a lamda carrageenan (e.g. Viscarin GP-209). In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium strearate and microcrystalline collulose and colloiddal silicon dioxide. In one aspect, the extended release formulation is a formulation of Table E. In yet another aspect, the extended release formulation is a formulation of Table 8.

In one variation, the extended release formulation comprises: (i) a hydrocolloid polymer; (ii) an anionic, pH-dependent, gel forming co-polymer, and (iii) either a water-swellable, pH independent polymer or a hydrogel. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium strearate and microcrystalline collulose and colloiddal silicon dioxide. In one aspect, the extended release formulation is a formulation of Table E. In yet another aspect, the extended release formulation is a formulation of Table 8. An extended release formulation in one variation comprises a therapeutic agent as detailed herein (e.g., sialic acid) and (i) a hydrocolloid polymer; (ii) an anionic, pH-dependent, gel forming co-polymer, and (iii) either a water-swellable, pH independent polymer or a hydrogel. Exemplary extended release formulations include those listed in Table A, where it is understood that an extended release formulation may comprise any of the listed therapeutic agents in combination with at least one of any of polymers 1, 2, 3A or 3B the same as if each and every combination of therapeutic agent and polymer or combination of polymers were specifically and individually listed. Although particular formulations may comprise a therapeutic agent of Table A and any one or more of a polymer selected from Polymers 1, 2 and 3 (A and/or B) of Table A, in a particular variation, an extended release formulation comprises a therapeutic agent of Table A, a polymer 1 of Table A, a polymer 2 of Table A and either a polymer 3A of Table A or a polymer 3B of Table A the same as if each and every combination of therapeutic agent and polymer combination were specifically and individually listed. For example, it is understood that in one aspect, an extended release formulation comprises sialic acid, carrageenan (e.g., a lambda carrageenan such as Viscarin GP-209), an alginate salt (e.g., sodium alginate such as Protanal® LF 120M), and either (i) hypromellose (e.g., hypromellose Type 2208) or (ii) polyethylene oxide (e.g., Polyox), or a pharmaceutically acceptable salt of any of the foregoing.

TABLE A

Exemplary Components for use in Extended Realease Formulations.

| | |
|---|---|
| Therapeutic Agent (A compound in the sialic acid biosynthetic pathway or derivative thereof or salt of any of the foregoing) | mannosamine, N-acetyl mannosamine (ManNAc), ManNac-6-phosphate (ManNAc-6-P), UDP-GlcNAc, N-acetylneuraminic acid (NeuAc), NeuAc-9-phosphate (NeuAc-9-P), sialic acid (i.e., 5-N-acetylneuraminic acid), CMP-sialic acid, and/or derivatives thereof or pharmaceutically acceptable salts of the foregoing. |
| Polymer 1 (Hydrocolloid Polymer) | Carrageenan (e.g., iota, kappa or lambda carrageenan, or a salt thereof, such as Viscarin GP-209, FMC BioPolymer) |
| Polymer 2 (Anionic, pH-dependent, gel forming co-polymer) | Alginate or salt thereof (e.g., sodium, potassium or ammonium alginate salt such as Protanal ®, FMC BioPolymer), carboxymethyl cellulose or salt thereof (e.g., sodium carboxymethyl cellulose). |
| Polymer 3A (Water-swellable, pH independent polymer) | Hypromellose (e.g., hypromellose Type 2208, E and K series such as for example, Dow Chemical Company's (Midland, Mich. USA) or Aqualon's (with a North American presence in Wilmington, Del.) E4M, E10M, K100LV, K4M, K15M, K25M, K100M, K200M and mixtures of various molecular weights and grades); hydroxypropyl ethyl cellulose (Ethocel polymers 7FP, 10FP and 100FP and Aqualon's polymers T10EC, N7, N10, N17, N22, N50, N100 and N200, and mixtures thereof), hydroxypropyl cellulose (Aqualon's HPC polymers MF and MXF (mol. wt. 580,000) and KF and HXF (mol. wt. 1,150,000), and mixtures thereof); hydroxyethyl cellulose (e.g., Aqualon's Natrasol polymers HHX (mol. Wt. 1,300,000), HX (mol. wt. 1,000,000), H (mol. wt. 1,000,000), M (mol. wt. 720,000 and G (mol. wt. 1,150,000), and mixtures thereof); methyl cellulose.. |
| Polymer 3B (Hydrogel) | Polyhydroxyethyle methylacrylate (PHEMA), polyvinyl alcohol (PVA), polyvinyl pyrrolidone (PVP), polyethylene oxide (PEO), polyacrylamide (PA), polyethylene oxide (e.g., Polyox ™ water soluble resin, Dow Chemical Company, Mich., USA). |

In one variation, an extended release formulation comprises a therapeutic agent of Table A, a polymer 1 of Table A, a polymer 2 of Table A and either a polymer 3A or a polymer 3B of Table A, wherein the composition comprises the therapeutic agent and polymers in any one of the weight percent ranges depicted in Table B.

TABLE B

Exemplary Weight Percent of Certain Components for Use in Extended Release Formulations.

| Formulation Component | Weight Percent of Component in Formulation |
|---|---|
| Therapeutic Agent (A compound in the sialic acid biosynthetic pathway or derivative thereof or salt of any of the foregoing) | From about 20 to about 80; from about 20 to about 60; from about 20 to about 50; from about 20 to about 40; from about 20 to about 30; from about 15 to about 60; from about 15 to about 50; from about 15 to about 40; from about 25 to about 60; from about 25 to about 50; from 25 to about 40; from about 25 to about 30; from about 30 to about 60; from about 30 to about 50; from about 30 to about 45; from about 30 to about 40; from about 35 to about 60; from about 35 to about 50; from about 35 to about 45; from about 40 to about 45; about any of 35, 36, 37, 38, 39, 40, 41, 42, 43, 44, 45, 46, 47, 48, 49 and 50. |
| Polymer 1 (Hydrocolloid Polymer) | From about 1 to about 10; from about 1 to about 5; from about 3 to about 8; from about 4 to about 6; about any of 1, 2, 3, 4, 5, 6, 7, 8, 9 and 10. |
| Polymer 2 (Anionic, pH-dependent, gel forming co-polymer) | From about 15 to about 30; from about 15 to about 25; from about 15 to about 20; from about 20 to about 30; from about 20 to about 25; from about 2o to about 23; about any of 15, 16, 17, 18, 19, 20, 21, 22, 23, 24 and 25. |
| Polymer 3A. (Water-swellable, pH independent polymer) Or Polymer 3B. (Hydrogel) | From about 20 to about 50; from about 20 to about 40, from about 20 to about 30; from about 20 to about 25; from about 25 to about 30; from about 22 to about 27; about any of 20, 21, 22, 23, 24, 25, 26, 27, 28, 29 and 30. |

In another variation, the extended release formulation comprises a therapeutic agent (a compound in the sialic acid biosynthetic pathway or derivative thereof or salt of any of the foregoing, such as any of the compounds detailed herein, including in Table A) and a polymer, wherein the polymer comprises: (i) a hydrocolloid polymer; (ii) an anionic, pH-dependent, gel forming co-polymer, and (iii) either a water-swellable, pH independent polymer or a hydrogel, and wherein the weight percent ratio of polymers (i):(ii):(iii) is about 1:5:5 or about 1:5:6.

The combination of (i) a hydrocolloid polymer; (ii) an anionic, pH-dependent, gel forming co-polymer, and (iii) either a water-swellable, pH independent polymer or a hydrogel is believed to provide a unique combination that is particularly advantageous for the preparation of oral dosage forms in that the combination results in any one or more of the following features: (i) provides a robust formulation (e.g., for tablet formulation); (i) is pH independent; and (iii) lends itself to granulation without affecting dissolution profile.

Further descriptions of extended release formulations and formulation components are found throughout and below.

It is understood that reference to relative weight percentages assumes that the combined total weight percentages of all components in the formulation add up to 100. It is further understood that relative weight percentages of one or more components may be adjusted upwards or downwards such that the weight percent of the components in the composition combine to a total of 100. In one aspect, the weight percentages detailed herein refer to the weight percentages of a formulation blend (e.g., prior to formulation into a unit dosage amount such as a tablet, which may be further modified, e.g., by the addition of a tablet coating). In another aspect, the weight percentages detailed herein refer to the weight percentages of a unit dosage of a formulation, in which the formulation is in a form and/or packaged for administration to an individual (e.g., a tablet that has a coating).

The polymer may be present in the extended release formulation in an amount ranging from 5 to 40 parts by weight, from 10 to 20 parts by weight, relative to 100 parts by weight of the one or more compounds in the sialic acid pathway or derivatives thereof. In some embodiments, the one or more compounds in the sialic acid pathway or derivatives thereof in such formulations includes from about 0.1 to 99.9% by weight of the formulation. In some embodiments, the one or more compounds in the sialic acid pathway or derivatives thereof in such formulations includes about any of between 20%-30%, 30%-40%, 40%-50%, or 20%-50%. In some embodiments, the extend release formulation includes about any of between 40%-50%, 50%-60%, 60%-70%, or 50% to 70% by weight of polymer.

In some embodiments, the drug load of the one or more compounds in the sialic acid pathway or derivatives thereof in the extended release formulation comprises about 20% to 80% w/w. In some embodiments, the drug load of the one or more compounds in the sialic acid pathway or derivatives thereof in the extended release formulation comprises about any one of 20% to 60% w/w, 20%-50% w/w, 20%-40% w/w, 15%-60% w/w, 15%-50% w/w, 15%-40% w/w, 25%-0.60% w/w, 25%-50% w/w, 25%-40% w/w, 30%-60% w/w, 30%-50% w/w, 30%-45% w/w, 35%-60% w/w, 35%-50% w/w, or 35%-45% w/w. In some embodiments, the drug load of the one or more compounds in the sialic acid pathway or derivatives thereof in the extended release formulation comprises at least about any one of 25% w/w, 30% w/w, 35% w/w, 40% w/w, 45% w/w, or 50% w/w. In some embodiments, the drug load of the one or more compounds in the sialic acid pathway or derivatives thereof in the extended release formulation comprises about 33% w/w. In some embodiments, the drug load of the one or more compounds in the sialic acid pathway or derivatives thereof in the extended release formulation comprises about 43% w/w In some embodiments, the extended release formulation comprises about 20 to about 50 or about 20 to about 40 or about 20 to about 30% w/w of a water-swellable, pH independent polymer (e.g., hypromellose). In some embodiments, the extended release formulation comprises about 25% w/w of a water-swellable, pH independent polymer (e.g., hypromellose). In some embodiments, the extended release formulation further comprises about 20-25% w/w of an anionic, pH-dependent, gel-forming copolymer (e.g., an alginate salt). In some embodiments, the extended release formulation further comprises about 21% w/w of an anionic, pH-dependent, gel-forming copolymer (e.g., an alginate salt). In some embodiments, the extended release formulation further comprises about 1-5% w/w of a hydrocolloid polymer (e.g., carrageenan). In some embodiments, the extended release formulation further comprises about 4% w/w of a hydrocolloid polymer (e.g., carrageenan). In some embodiments, the extended release formulation comprises about 20-30% w/w of a water-swellable, pH independent polymer (e.g. hypromellose), about 20-25% w/w of an anionic, pH-dependent, gel-forming copolymer (e.g., an alginate salt) and about 1-5% w/w of a hydrocolloid polymer (e.g., a carrageenan). In some embodiments, the extended release formulation comprises about 20-30% w/w hypromellose (e.g. hypromellose Type 2208 or Methocel K100M), about 20-25% w/w sodium alginate (e.g. Protanal) and about 1-5% w/w lamda carrageenan (e.g. Viscarin GP-209). In some embodiments, the extended release formulation comprises about 25% w/w of a water-swellable, pH independent polymer (e.g. hypromellose), about 21% w/w of an anionic, pH-dependent, gel-forming copolymer (e.g., an alginate salt) and about 4% w/w of a hydrocolloid polymer (e.g., a carrageenan). In some embodiments, the extended release formulation comprises about 25% w/w hypromellose (e.g. hypromellose Type 2208 or Methocel K100M), about 21% w/w sodium alginate (e.g. Protanal) and about 4% w/w lamda carrageenan (e.g. Viscarin GP-209).

In some embodiments, the extended release formulation comprises about 20 to about 50 or about 20 to about 40 or about 20 to about 20-30% w/w of a hydrogel (e.g., a polyethylene oxide, Polyox WSR). In some embodiments, the extended release formulation comprises about 25% w/w of a hydrogel (e.g., a polyethylene oxide, Polyox WSR). In some embodiments, the extended release formulation further comprises about 20-25% w/w of an anionic, pH-dependent, gel-forming copolymer (e.g., an alginate salt). In some embodiments, the extended release formulation further comprises about 21% w/w of an anionic, pH-dependent, gel-forming copolymer (e.g., an alginate salt). In some embodiments, the extended release formulation further comprises about 1-5% w/w of a hydrocolloid polymer (e.g., carrageenan). In some embodiments, the extended release formulation further comprises about 4% w/w of a hydrocolloid polymer (e.g., carrageenan). In some embodiments, the extended release formulation comprises about 20-30% w/w of a hydrogel (e.g., a polyethylene oxide), about 20-25% w/w of an anionic, pH-dependent, gel-forming copolymer (e.g., an alginate salt) and about 1-5% w/w of a hydrocolloid polymer (e.g., a carrageenan). In some embodiments, the extended release formulation comprises about 20-30% w/w polyethylene oxide (e.g. Polyox WSR), about 20-25% w/w sodium alginate (e.g. Protanal) and about 1-5% w/w lamda carrageenan (e.g. Viscarin GP-209). In some embodiments, the extended release formulation comprises about 25% w/w of a hydrogel (e.g., a polyethylene oxide), about 21% w/w of an anionic, pH-dependent, gel-forming copolymer (e.g., an alginate salt) and about 4% w/w of a hydrocolloid polymer (e.g., a carrageenan). In some embodiments, the extended release formulation comprises about 25% w/w polyethylene oxide (e.g. Polyox WSR), about 21% w/w sodium alginate (e.g. Protanal) and about 4% w/w lamda carrageenan (e.g. Viscarin GP-209).

Additional Formulation Components

The extended release pharmaceutical formulations comprising one or more compounds in the sialic acid biosynthetic pathway or derivative thereof as described herein may further comprise a diluent, an excipient, an antioxidant, a lubricant, a colorant, a binder, a disintegrant, and the like. It is understood that any of the extended release formulations detailed herein, including but not limited to those listed under the heading "Extended Release Formulations" (e.g., any formulation of Tables A or B) may further comprise a diluent, an excipient, an antioxidant, a lubricant, a colorant, a binder, a disintegrant, and the like as detailed herein the same as if each and every extended release formulation further comprising such a component were specifically and individually listed. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium strearate and microcrystalline collulose and colloiddal silicon dioxide. In one aspect, the extended release formulation is a formulation of Table E. In yet another aspect, the extended release formulation is a formulation of Table 8.

The diluent is selected so as not to affect the biological activity of the combination. Examples of such diluents are distilled water, buffered water, physiological saline, PBS, Ringer's solution, dextrose solution, and Hank's solution. The pharmaceutical formulations can also include additional substances to approximate physiological conditions, such as pH adjusting and buffering agents, toxicity adjusting agents, wetting agents and detergents. The pharmaceutical formulations can also include any of a variety of stabilizing agents. Further guidance regarding pharmaceutical formulations that are suitable for various types of administration can be found in Remington: The Science and Practice of Pharmacy, 20th Edition. Baltimore, Md.: Lippincott Williams & Wilkins, 2000.

The excipient may be selected from the group consisting of lactose, microcrystalline cellulose, corn starch, potato starch, wheat starch, sucrose, D-mannitol, precipitated calcium carbonate, dextrin, pre-gelatinized starch, and combinations thereof. The excipient, if present, may be contained in an amount of about 10 to about 90 parts by weight based on the total weight of the tablet. In some embodiments, the extend release formulation includes about any of between 40%-50%, 50%-60%, 60%-70%, or 50% to 70% by weight of excipient. In some embodiments, the excipient is microcrystalline cellulose. In some embodiments, the excipient is microcrystalline cellulose and colloidal silicon dioxide (e.g., ProSolv® SMCC HD90). In some embodiments, the extended release formulation comprises about 1-10% w/w of microcrystalline cellulose and colloidal silicon dioxide (e.g., ProSolv® SMCC HD90). In some embodiments, the extended release formulation comprises about 5% w/w of microcrystalline cellulose and colloidal silicon dioxide (e.g., ProSolv® SMCC HD90).

The binder may be selected from the group consisting of hydroxypropylcellulose, direct tabletted microcrystalline cellulose, FIPMC, MC, hydroxyethylcellulose, hydroxymethylcellulose, carboxymethyl cellulose, and other cellulose derivative, PVP, PVA, paste, arabic gum, dextrin, gelatin, alginates, and combinations thereof. The binder, if present, may be used in an amount of about 2 to about 60 parts by weight based on the total weight of the tablet.

The disintegrant may be selected from the group consisting of sodium starch glycolate, crosspovidone, cross carmellose sodium, low-substituted hydroxypropylcellulose, starch, carboxymethylcellulose calcium, calcium carbonate, sodium bicarbonate, and combinations thereof. The disintegrant, if present, may be contained in an amount of about 0.1 to about 32 parts by weight based on the total weight of the tablet composition.

The lubricant may be selected from the group consisting of magnesium stearate, calcium stearate, talc, light anhydrous silicic acid, and solid polyethyl glycols and combinations thereof. The lubricant, if present, may be contained in an amount of about 0.1 to about 20 parts by weight based on the total weight of the tablet. In some embodiments, the lubricant is magnesium stearate (e.g., HyQual®). In some embodiments, the extended release formulation comprises about 0.1-1% w/w magnesium stearate (e.g., HyQual®). In some embodiments, the extended release formulation comprises about 0.5% w/w magnesium stearate (e.g., HyQual®).

For the colorant, at least one species which can be selected from titanium dioxide, iron oxide, magnesium carbonate, calcium sulfate, magnesium oxide, magnesium hydroxide, aluminum lakes, for example, Blue No. 1 Aluminum Lake, Red No. 40 Aluminum Lake, and the like can be contained in the tablet.

In another variation, an extended release formulation detailed herein (including but not limited to those listed under the heading "Extended Release Formulations" (e.g., any formulation of Tables A and B) further comprises an excipient. In a particular variation, the excipient comprises microcrystalline cellulose. In a further variation, the excipient comprises microcrystalline cellulose and colloidal silicon dioxide. In any such variations, the extended release formulation further comprising an excipient (e.g., an excipient comprising microcrystalline cellulose and colloidal silicon dioxide) comprises the excipient in about 1 to about 20 or about 1 to about 15 or about 1 to about 10 or about 1 to about 5 or about 5 to about 20 or about 5 to about 15 or about 5 to about 10 or about any one of 1, 2, 3, 4, 5, 6, 7, 8, 9 or 10 weight percent. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium strearate and microcrystalline collulose and colloiddal silicon dioxide. In one aspect, the extended release formulation is a formulation of Table E. In yet another aspect, the extended release formulation is a formulation of Table 8.

In another variation, an extended release formulation detailed herein (including but not limited to those listed under the heading "Extended Release Formulations" (e.g., any formulation of Tables A and B) further comprises a lubricant. In a particular variation, the lubricant comprises a stearate salt, such as magnesium stearate. In any such variations, the extended release formulation further comprising a lubricant (e.g., a stearate salt such as magnesium stearate) comprises the lubricant in about 0.1 to about 2 or about 0.1 to about 1.5 or about 0.1 to about 1.0 or about 0.01 to about 0.09-5 or about 0.1 to about 0.8 or about 0.1 to about 0.7 or about 0.1 to about 0.6 or about 0.1 to about 0.5 or about 0.2 to about 0.8 or about 0.3 to about 0.7 or about 0.4 to about 0.6 or about any one of 0.1, 0.2, 0.3, 0.4, 0.5, 0.6, 0.7, 0.8, 0.9 or 1.0 weight percent. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium strearate and microcrystalline collulose and colloiddal silicon dioxide. In one aspect, the extended release formulation is a formulation of Table E. In yet another aspect, the extended release formulation is a formulation of Table 8.

In a further variation, an extended release formulation detailed herein (including but not limited to those listed under the heading "Extended Release Formulations" (e.g., any formulation of Tables A and B) further comprises both an excipient and a lubricant. In any such variation, the formulation further comprising both an excipient and a lubricant comprises the excipient (e.g., an excipient comprising microcrystalline cellulose and colloidal silicon dioxide) in about 1 to about 20 or about 1 to about 15 or about 1 to about 10 or about 1 to about 5 or about 5 to about 20 or about 5 to about 15 or about 5 to about 10 or about any one of 1, 2, 3, 4, 5, 6, 7, 8, 9 or 10 weight percent and comprises the lubricant (e.g., a stearate salt such as magnesium stearate) in about 0.1 to about 2 or about 0.1 to about 1.5 or about 0.1 to about 1.0 or about 0.01 to about 0.09-5 or about 0.1 to about 0.8 or about 0.1 to about 0.7 or about 0.1 to about 0.6 or about 0.1 to about 0.5 or about 0.2 to about 0.8 or about 0.3 to about 0.7 or about 0.4 to about 0.6 or about any one of 0.1, 0.2, 0.3, 0.4, 0.5, 0.6, 0.7, 0.8, 0.9 or 1.0 weight percent. In a further variation, the formulation further comprising both an excipient and a lubricant comprises the excipient (e.g., an excipient comprising microcrystalline cellulose and colloidal silicon dioxide) in a weight percent ratio to lubricant (e.g., a stearate salt such as magnesium stearate) of about any of 1:10 or 1:11 or 1:9 or 1:10.5. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium strearate and microcrystalline collulose and colloiddal silicon dioxide. In one aspect, the extended release formulation is a formulation of Table E. In yet another aspect, the extended release formulation is a formulation of Table 8.

Particular extended release formulations include those listed in Table C, where the compositions comprise a therapeutic agent, a polymer 1, a polymer 2, either a polymer 3A or a polymer 3B, an excipient and a lubricant, and it is understood that each and every combination of such components is intended the same as if each and every combination were specifically and individually listed.

TABLE C

Exemplary Extended Release Formulation Compositions.

| Formulation Component | Exemplary Specific Components |
|---|---|
| Therapeutic Agent (A compound in the sialic acid biosynthetic pathway or derivative thereof or salt of any of the foregoing) | mannosamine, N-acetyl mannosamine (ManNAc), ManNac-6-phosphate (ManNAc-6-P), UDP-GlcNAc, N-acetylneuraminic acid (NeuAc), NeuAc-9-phosphate (NeuAc-9-P), sialic acid (i.e., 5-N-acetylneuraminic acid), CMP-sialic acid, and/or derivatives thereof or pharmaceutically acceptable salts of the foregoing. |
| Polymer 1 (Hydrocolloid Polymer) | Carrageenan (e.g., iota, kappa or lambda carrageenan, or a salt thereof, such as Viscarin GP-209, FMC BioPolymer) |
| Polymer 2 (Anionic, pH-dependent, gel forming co-polymer) | Alginate or salt thereof (e.g., sodium, potassium or ammonium alginate salt such as Protanal ®, FMC BioPolymer), carboxymethyl cellulose or salt thereof (e.g., sodium carboxymethyl cellulose). |
| Polymer 3A (Water-swellable, pH independent polymer) | Hypromellose (e.g., hypromellose Type 2208, E and K series such as for example, Dow Chemical Company's (Midland, Mich. USA) or Aqualon's (with a North American presence in Wilmington, Del.) E4M, E10M, K100LV, K4M, K15M, K25M, K100M, K200M and mixtures of various molecular weights and grades); hydroxypropyl ethyl cellulose (Ethocel polymers 7FP, 10FP and 100FP and Aqualon's polymers T10EC, N7, N10, N17, N22, N50, N100 and N200, and mixtures thereof), hydroxypropyl cellulose (Aqualon's HPC polymers MF and MXF (mol. wt. 580,000) and KF and HXF (mol. wt. 1,150,000), and mixtures thereof); hydroxyethyl cellulose (e.g., Aqualon's Natrasol polymers HHX (mol. Wt. 1,300,000), HX (mol. wt. 1,000,000), H (mol. wt. 1,000,000), M (mol. wt. 720,000 and G (mol. wt. 1,150,000), and mixtures thereof); methyl cellulose.. |

TABLE C-continued

Exemplary Extended Release Formulation Compositions.

| Formulation Component | Exemplary Specific Components |
|---|---|
| Polymer 3B (Hydrogel) | Polyhydroxyethyle methylacrylate (PHEMA), polyvinyl alcohol (PVA), polyvinyl pyrrolidone (PVP), polyethylene oxide (PEO), polyacrylamide (PA), polyethylene oxide (e.g., Polyox ™ water soluble resin, Dow Chemical Company, Mich., USA). |
| Excipient | lactose, microcrystalline cellulose, corn starch, potato starch, wheat starch, sucrose, D-mannitol, precipitated calcium carbonate, dextrin, pre-gelatinized starch, microcrystalline cellulose and colloidal silicon dioxide (e.g., ProSolv ® SMCC HD90) and combinations thereof. |
| Lubricant | Stearate salt (such as magnesium stearate (e.g., HyQual ®) and calcium stearate), talc, light anhydrous silicic acid, and solid polyethyl glycols and combinations thereof. |

In one variation, an extended release formulation is a composition as detailed in Table C, wherein the composition comprises the formulation components in any one of the weight percent ranges depicted in Table D. It is understood that each and every combination of such components and weight percentages is intended the same as if each and every combination of component and weight percentage were specifically and individually listed.

TABLE D

Exemplary Weight Percent of Certain Components for Use in Extended Release Formulations

| Formulation Component | Exemplary Specific Components | Exemplary w/w % |
|---|---|---|
| Therapeutic Agent (A compound in the sialic acid biosynthetic pathway or derivative thereof or salt of any of the foregoing) | mannosamine, N-acetyl mannosamine (ManNAc), ManNac-6-phosphate (ManNAc-6-P), UDP-GlcNAc, N-acetylneuraminic acid (NeuAc), NeuAc-9-phosphate (NeuAc-9-P), sialic acid (i.e., 5-N-acetylneuraminic acid), CMP-sialic acid, and/or derivatives thereof or pharmaceutically acceptable salts of the foregoing. | From about 20 to about 80; from about 20 to about 60; from about 20 to about 50; from about 20 to about 40; from about 20 to about 30; from about 15 to about 60; from about 15 to about 50; from about 15 to about 40; from about 25 to about 60; from about 25 to about 50; from 25 to about 40; from about 25 to about 30; from about 30 to about 60; from about 30 to about 50; from about 30 to about 45; from about 30 to about 40; from about 35 to about 60; from about 35 to about 50; from about 35 to about 45; from about 40 to about 45; about any of 35, 36, 37, 38, 39, 40, 41, 42, 43, 44, 45, 46, 47, 48, 49 and 50. |
| Polymer 1 (Hydrocolloid Polymer) | Carrageenan (e.g., iota, kappa or lambda carrageenan, or a salt thereof, such as Viscarin GP-209, FMC BioPolymer) | From about 1 to about 10; from about 1 to about 5; from about 3 to about 8; from about 4 to about 6; about any of 1, 2, 3, 4, 5, 6, 7, 8, 9 and 10. |
| Polymer 2 (Anionic, pH-dependent, gel forming co-polymer) | Alginate or salt thereof (e.g., sodium, potassium or ammonium alginate salt such as Protanal ®, FMC BioPolymer), carboxymethyl cellulose or salt thereof (e.g., sodium carboxymethyl cellulose). | From about 15 to about 30; from about 15 to about 25; from about 15 to about 20; from about 20 to about 30; from about 20 to about 25; from about 2o to about 23; about any of 15, 16, 17, 18, 19, 20, 21, 22, 23, 24 and 25. |
| Polymer 3A (Water-swellable, pH independent polymer) | Hypromellose (e.g., hypromellose Type 2208, E and K series such as for example, Dow Chemical Company's (Midland, Mich. USA) or Aqualon's (with a North American presence in Wilmington, Del.) E4M, E10M, K100LV, K4M, K15M, K25M, K100M, K200M and mixtures of various molecular weights and grades); hydroxypropyl ethyl cellulose (Ethocel polymers 7FP, 10FP and 100FP and Aqualon's polymers T10EC, N7, N10, N17, N22, N50, N100 and N200, and mixtures thereof), hydroxypropyl cellulose (Aqualon's HPC polymers MF and MXF (mol. wt. 580,000) and KF and HXF (mol. wt. 1,150,000), and mixtures thereof); | From about 20 to about 50; from about 20 to about 40, from about 20 to about 30; from about 20 to about 25; from about 25 to about 30; from about 22 to about 27; about any of 20, 21, 22, 23, 24, 25, 26, 27, 28, 29 and 30. |

TABLE D-continued

Exemplary Weight Percent of Certain Components for Use in Extended Release Formulations

| Formulation Component | Exemplary Specific Components | Exemplary w/w % |
|---|---|---|
| | hydroxyethyl cellulose (e.g., Aqualon's Natrasol polymers HHX (mol. Wt. 1,300,000), HX (mol. wt. 1,000,000), H (mol. wt. 1,000,000), M (mol. wt. 720,000 and G (mol. wt. 1,150,000), and mixtures thereof); methyl cellulose.. | |
| Polymer 3B (Hydrogel) | Polyhydroxyethyle methylacrylate (PHEMA), polyvinyl alcohol (PVA), polyvinyl pyrrolidone (PVP), polyethylene oxide (PEO), polyacrylamide (PA), polyethylene oxide (e.g., Polyox ™ water soluble resin, Dow Chemical Company, Mich., USA). | From about 20 to about 30; from about 20 to about 25; from about 25 to about 30; from about 22 to about 27; about any of 20, 21, 22, 23, 24, 25, 26, 27, 28, 29 and 30. |
| Excipient | lactose, microcrystalline cellulose, corn starch, potato starch, wheat starch, sucrose, D-mannitol, precipitated calcium carbonate, dextrin, pre-gelatinized starch, microcrystalline cellulose and colloidal silicon dioxide (e.g., ProSolv ® SMCC HD90) and combinations thereof. | From about 1 to about 20 or about 1 to about 15 or about 1 to about 10 or about 1 to about 5 or about 5 to about 20 or about 5 to about 15 or about 5 to about 10 or about any one of 1, 2, 3, 4, 5, 6, 7, 8, 9 or 10 weight percent. |
| Lubricant | Stearate salt (such as magnesium stearate (e.g., HyQual ®) and calcium stearate), talc, light anhydrous silicic acid, and solid polyethyl glycols and combinations thereof. | From about 0.1 to about 2 or about 0.1 to about 1.5 or about 0.1 to about 1.0 or about .01 to about .09-5 or about 0.1 to about 0.8 or about 0.1 to about 0.7 or about 0.1 to about 0.6 or about 0.1 to about 0.5 or about 0.2 to about 0.8 or about 0.3 to about 0.7 or about 0.4 to about 0.6 or about any one of 0.1, 0.2, 0.3, 0.4, 0.5, 0.6, 0.7, 0.8, 0.9 or 1.0 weight percent. |

In another variation, extended release formulations are provided wherein the formulation comprises a therapeutic agent of Table C, a polymer 1 of Table C, a polymer 2 of Table C, a Polymer 3A or a polymer 3B of Table C, an excipient of Table C and a lubricant of Table C, wherein the components are present in the composition in the following weight percent ratios. In one aspect, the weight percent ratio of Lubricant:Polymer 1:Excipient:Polymer 2:Polymer 3A or 3B:Therapeutic Agent is about 1:8:10:40:50:85 or about 1:8.5:10.5:42.5:51:86.5 or about 1:8.4:10.6:42.4:51:86.6.

In any of the formulae detailed herein, including but not limited to the formulations in any of Tables A-D, in one aspect the therapeutic agent is sialic acid or ManNAc or a pharmaceutically acceptable salt thereof or a combination of sialic acid or ManNAc. In a particular aspect of any of the formulations detailed herein, including but not limited to the formulations in any of Tables A-D, the therapeutic agent is sialic acid, or a pharmaceutically acceptable salt thereof.

Particular extended release formulations of sialic acid are provided in Table E. In one variation, ManNAc may be used in place of sialic acid in the formulations of Table E.

TABLE E

Exemplary Extended Release Formulations of sialic acid.

| Formulation Component | Exemplary w/w % |
|---|---|
| Sialic acid, or pharmaceutically acceptable salt thereof | From about 20 to about 80; from about 20 to about 60; from about 20 to about 50; from about 20 to about 40; from about 20 to about 30; from about 15 to about 60; from about 15 to about 50; from about 15 to about 40; from about 25 to about 60; from about 25 to about 50; from 25 to about 40; from about 25 to about 30; from about 30 to about 60; from about 30 to about 50; from about 30 to about 45; from about 30 to about 40; from about 35 to about 60; from about 35 to about 50; from about 35 to about 45; from about 40 to about 45; about any of 35, 36, 37, 38, 39, 40, 41, 42, 43, 44, 45, 46, 47, 48, 49 and 50. |
| Carrageenan (e.g., lambda carrageenan such as Viscarin GP-209, FMC BioPolymer) | From about 1 to about 10; from about 1 to about 5; from about 3 to about 8; from about 4 to about 6; about any of 1, 2, 3, 4, 5, 6, 7, 8, 9 and 10. |

TABLE E-continued

Exemplary Extended Release Formulations of sialic acid.

| Formulation Component | Exemplary w/w % |
|---|---|
| Alginate or a salt thereof (e.g., sodium, potassium or ammonium alginate salt such as Protanal ® LF 120M) | From about 15 to about 30; from about 15 to about 25; from about 15 to about 20; from about 20 to about 30; from about 20 to about 25; from about 2o to about 23; about any of 15, 16, 17, 18, 19, 20, 21, 22, 23, 24 and 25. |
| Hypromellose (such as hypromellose Type 2208, e.g., Methocel ®K100 M Premium CR) | From about 20 to about 50; from about 20 to about 40, from about 20 to about 30; from about 20 to about 25; from about 25 to about 30; from about 22 to about 27; about any of 20, 21, 22, 23, 24, 25, 26, 27, 28, 29 and 30. |
| Polyethylene oxide (such as Polyethylene Oxide WSR, e.g., Polyox ™ water soluble resin, Dow Chemical Company, Mich., USA) | From about 20 to about 30; from about 20 to about 25; from about 25 to about 30; from about 22 to about 27; about any of 20, 21, 22, 23, 24, 25, 26, 27, 28, 29 and 30. |
| Microcrystalline cellulose and colloidal silicon dioxide (e.g., ProSolv ® SMCC HD90) | From about 1 to about 20 or about 1 to about 15 or about 1 to about 10 or about 1 to about 5 or about 5 to about 20 or about 5 to about 15 or about 5 to about 10 or about any one of 1, 2, 3, 4, 5, 6, 7, 8, 9 or 10 weight percent. |
| Stearate salt (such as magnesium stearate (e.g., HyQual ®) | From about 0.1 to about 2 or about 0.1 to about 1.5or about 0.1 to about 1.0 or about .01 to about .09-5 or about 0.1 to about 0.8 or about 0.1 to about 0.7 or about 0.1 to about 0.6 or about 0.1 to about 0.5 or about 0.2 to about 0.8 or about 0.3 to about 0.7 or about 0.4 to about 0.6 or about any one of 0.1, 0.2, 0.3, 0.4, 0.5, 0.6, 0.7, 0.8, 0.9 or 1.0 weight percent. |

The components used to formulate the extended release pharmaceutical formulations are preferably of high purity and are substantially free of potentially harmful contaminants (e.g., at least National Food (NF) grade, generally at least analytical grade, and more typically at least pharmaceutical grade). Moreover, pharmaceutical formulations intended for in vivo use are usually sterile. To the extent that a given compound must be synthesized prior to use, the resulting product is typically substantially free of any potentially toxic agents which may be present during the synthesis or purification process. Compositions for parental administration are also sterile, substantially isotonic and made under GMP conditions.

The blends of the extended release formulation may have a particle size with a majority of particles being retained by a sieve size of 45 μm. In some embodiments, the blends of the extended release formulation have a particle size with at least any one of 10%, 30%, 40%, 50% of particles retained by a sieve size of 45 μm.

The extended release pharmaceutical formulations as described herein may be formulated into preparations in solid, semi-solid, liquid or gaseous forms, such as tablets, capsules, powders, granules, ointments, solutions, suppositories, injections, inhalants, gels, microspheres, and aerosols. In some embodiments of any of the extended release pharmaceutical formulations described herein, the extended release pharmaceutical formulations is formulated for administration by a variety of routes including oral, parenteral (including subcutaneous, intravenous, intramuscular and intraperitoneal), rectal, dermal, transdermal, intrathoracic, intrapulmonary and intranasal (respiratory) routes. In some embodiments, the extended release pharmaceutical formulation is formulated for oral administration.

Any of the extended release formulations detailed herein may in one variation be formulated for oral administration. For example, any of the formulations provided under the heading "Extended Release Formulations," including but not limited to any of the formulations set forth in Tables A-E may in one variation be a formulation that is suitable for oral administration. A formulation that is suitable for oral administration may be formulated as a solid oral dosage form, such as a tablet or a capsule comprising the formulation as a powder. In one aspect, a solid oral dosage form of an extended release formulation is provided wherein the solid oral dosage form comprises any formulation provided herein (including but not limited to the formulations set forth in any one of Tables A-E) in tablet form, wherein the tablet further comprises a coating (e.g., Opadry-II White). In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium strearate and microcrystalline colullose and colloiddal silicon dioxide. In one aspect, the extended release formulation is a formulation of Table E. In yet another aspect, the extended release formulation is a formulation of Table 8.

For oral administration, the sialic acid biosynthetic pathway or derivative thereof as described herein can be administered in solid dosage forms, such as capsules, tablets, and powders, or in liquid dosage forms, such as elixirs, syrups, and suspensions.

In some embodiments, the pharmaceutical formulations comprise an enteric-coating. Numerous types of acid-resistant enteric coatings are available. Examples of the acid-resistant coatings include cellulose acetate phthalate, polyvinyl acetate phthalate, shellac, an acrylic acid homopolymer or copolymer, a methacrylic acid homopolymer or copolymer, cellulose acetate trimellitate, hydroxypropyl methylcellulose phthalate or a combination of thereof. A number of copolymers of methacrylic acid are known in the art and are commercially available. Examples of such polymers are copolymers of methylmethacrylate and methacrylic acid and copolymers of ethylacrylate and methacrylic acid, and sold under the tradename Eudragit (Rohm GmbH & Co. KG): examples include Eudragit® L 100-55, Eudragit® L 30D-55, Eudragit® L 100, Eudragit® S 100-55 and Eudragit® FS 30D. In some embodiments, the enteric coating comprises one or more of titanium dioxide, polydextrose, hypromellose, triacetin and macrogol/PEG. In some embodiments, the enteric coating is Opadry® II White. In some embodiments, the enteric coating (e.g., Opadry® II White) comprises about 1-5% w/w of the extended release formulation. In some embodiments, the enteric coating (e.g., Opadry® II White) comprises about 1-5% w/w of the extended release formulation.

An enteric coating can also be a time-release coating. The time-release coatings are degraded away at a relatively constant rate until the coatings dissolve sufficiently for the time-release coatings to rupture. Thus, the time required for the rupture of the enteric coatings is largely time-dependent (i.e., thickness), and largely pH independent. Examples of time-release coating materials include cellulose acetate, cellulose acetate butyrate, cellulose acetate propionate, EC, and copolymers of acrylate and methacrylates with quaternary ammonium groups such as Eudragit® RL and Eudragit® RS and Eudragit® NE30-D.

The extended release pharmaceutical formulations can be further subjected to a process of film coating. For the film coating agent, an enteric or non-enteric film coating agent may be used, and the enteric film coating agent can be cellulose acetate phthalate (CAP), polyvinyl acetate phthalate (PVAP), a methacrylate polymer (Eudragit L, S), or the like, while the non-enteric film coating agent can be hydroxypropylcellulose (HPC), MC, EC, HPMC, povidone, PVA, CA, shellac, or the like. The process of coating can be performed by, for example, a pan coating method, a fluidized bed coating method, a compression coating method, or the like.

Coated tablets of the extended release formulation may be prepared in various sizes. For example, the coated tablets may have a length of about 16-20 mm, a width of about 7-12 mm and a thickness of about 5-8 mm. In some embodiments, the coated tablets have a length of about 17.7 mm, a width of about 9.1 mm and a thickness of about 6.7 mm. In some embodiments, the coated tablets have a length of about 19.3 mm, a width of about 9.7 mm and a thickness of about 8.0 mm.

In embodiments of any of the methods, the extended release formulation comprises a drug load of about 30-60% (e.g., sialic acid and/or ManNAc), about 20-30% w/w of a water-swellable, pH independent polymer (e.g. hypromellose), about 20-25% w/w of an anionic, pH-dependent, gel-forming copolymer (e.g., an alginate salt), about 1-5% w/w of a hydrocolloid polymer (e.g., a carrageenan), about 1-10% w/w of microcrystalline cellulose and colloidal silicon dioxide (e.g., Prosolv® SMCC HD90), about 0.1-1% w/w/magnesium stearate (e.g. HyQual®), and about 1-5% of an enteric coating (e.g. Opadry® II White). In some embodiments, the extended release formulation comprises a drug load of about 30-60% (e.g., sialic acid and/or ManNAc), about 20-30% w/w hypromellose (e.g. hypromellose Type 2208 or Methocel K100M), about 20-25% w/w sodium alginate (e.g. Protanal), about 1-5% w/w lamda carrageenan (e.g. Viscarin GP-209), about 1-10% w/w of microcrystalline cellulose and colloidal silicon dioxide (e.g., Prosolv® SMCC HD90), about 0.1-1% w/w/magnesium stearate (e.g. HyQual®), and about 1-5% of an enteric coating (e.g. Opadry® II White). In some embodiments, the extended release formulation comprises a drug load of about 30-60% (e.g., sialic acid and/or ManNAc), about 25% w/w of a water-swellable, pH independent polymer (e.g. hypromellose), about 21% w/w of an anionic, pH-dependent, gel-forming copolymer (e.g., an alginate salt), about 4% w/w of a hydrocolloid polymer (e.g., a carrageenan), about 5% w/w of microcrystalline cellulose and colloidal silicon dioxide (e.g., Prosolv® SMCC HD90), about 0.5% w/w/magnesium stearate (e.g. HyQual®), and about 3.5% of an enteric coating (e.g. Opadry® II White). In some embodiments, the extended release formulation comprises a drug load of about 30-60% (e.g., sialic acid and/or ManNAc), about 25% w/w hypromellose (e.g. hypromellose Type 2208 or Methocel K100M), about 21% w/w sodium alginate (e.g. Protanal), about 4% w/w lamda carrageenan (e.g. Viscarin GP-209), about 5% w/w of microcrystalline cellulose and colloidal silicon dioxide (e.g., Prosolv® SMCC HD90), about 0.5% w/w/magnesium stearate (e.g. HyQual®), and about 3.5% of an enteric coating (e.g. Opadry® II White).

In embodiments of any of the methods, the extended release formulation comprises a drug load of about 30-60% (e.g., sialic acid and/or ManNAc), about 20-30% w/w of a hydrogel (e.g. polyethylene oxide), about 20-25% w/w of an anionic, pH-dependent, gel-forming copolymer (e.g., an alginate salt), about 1-5 w/w of a hydrocolloid polymer (e.g., a carrageenan), about 1-10% w/w of microcrystalline cellulose and colloidal silicon dioxide (e.g., Prosolv® SMCC HD90), about 0.1-1% w/w/magnesium stearate (e.g. HyQual®), and about 1-5% of an enteric coating (e.g. Opadry® II White). In some embodiments, the extended release formulation comprises a drug load of about 30-60% (e.g., sialic acid and/or ManNAc), about 20-30% w/w polyethylene oxide (e.g. Polyox WSR), about 20-25% w/w sodium alginate (e.g. Protanal), about 1-5% w/w lamda carrageenan (e.g. Viscarin GP-209), about 1-10% w/w of microcrystalline cellulose and colloidal silicon dioxide (e.g., Prosolv® SMCC HD90), about 0.1-1% w/w/magnesium stearate (e.g. HyQual®), and about 1-5% of an enteric coating (e.g. Opadry® II White). In some embodiments, the extended release formulation comprises a drug load of about 30-60% (e.g., sialic acid and/or ManNAc), about 25% w/w of a hydrogel (e.g. polyethylene oxide), about 21% w/w of an anionic, pH-dependent, gel-forming copolymer (e.g., an alginate salt), about 4% w/w of a hydrocolloid polymer (e.g., a carrageenan), about 5% w/w of microcrystalline cellulose and colloidal silicon dioxide (e.g., Prosolv® SMCC HD90), about 0.5% w/w/magnesium stearate (e.g. HyQual®), and about 3.5% of an enteric coating (e.g. Opadry® II White). In some embodiments, the extended release formulation comprises a drug load of about 30-60% (e.g., sialic acid and/or ManNAc), about 25% w/w polyethylene oxide (e.g. Polyos WSR), about 21% w/w sodium alginate (e.g. Protanal), about 4% w/w lamda carrageenan (e.g. Viscarin GP-209), about 5% w/w of microcrystalline cellulose and colloidal silicon dioxide (e.g., Prosolv® SMCC HD90), about 0.5% w/w/magnesium stearate (e.g. HyQual®), and about 3.5% of an enteric coating (e.g. Opadry® II White).

Extended Release Formulation Characteristics

Any of the extended release formulations detailed herein, including but not limited to those detailed under the heading "Extended Release Formulation" and "Additional Formulation Components" (e.g., any of the formulations of Tables A-E) may exhibit any of the characteristics detailed herein and below. In a particular variation, any of the extended release formulations detailed herein may exhibit any one or more of the following characteristics: (i) capable of delivering to an individual in need thereof a therapeutically effective amount of one or more compounds in the sialic acid pathway or derivatives thereof over a period of greater than about any of 1, 2, 3, 4, 5, 6, 7, 8, 9, 10, 11, 12, 13, 14, 15, 16, 17, 18, 19, 20, 21, 22, 23, or 24 hours; (ii) capable of delivering to an individual in need thereof a substantially constant therapeutically effective amount of one or more compounds in the sialic acid pathway or derivatives thereof over a period of greater than about any of 1, 2, 3, 4, 5, 6, 7, 8, 9, 10, 11, 12, 13, 14, 15, 16, 17, 18, 19, 20, 21, 22, 23, or 24 hours; (iii) capable of delivering to an individual in need thereof a therapeutically effective amount of one or more compounds in the sialic acid pathway or derivatives thereof with a $T_{max}$ of between about any of 2-4 hours, 3-4 hours, 6-8 hours, 6-12 hours, 6-15 hours, 12-18 hours, or 18-24 hours; (iv) capable of delivering to an individual in need thereof a therapeutically effective amount of one or more compounds in the sialic acid pathway or derivatives thereof with a $C_{max}$ of about 0.5-100 µg/mL; (v) capable of delivering to an individual in need thereof a therapeutically effective amount of one or more compounds in the sialic acid pathway or derivatives thereof with a trough level of about 0.1-20 µg/mL; (vi) capable of delivering to an individual in need thereof a therapeutically effective amount of one or more compounds in the sialic acid pathway or derivatives thereof with less than about any of 10%, 20%, 30%, 40%, 50%, 60%, or 70% excreted after one hour; (vii) capable of delivering to an individual in need thereof between about any of 0.01-750 mg/kg/day, 0.5-500 mg/kg/day, 1-250 mg/kg/day, 2.5-100 mg/kg/day, or 5-50 mg/kg/day of one or more compounds in the sialic acid pathway or derivatives thereof or a pharmaceutically acceptable salt of the foregoing; (viii) capable of delivering to an individual in need thereof between about any of 0.01-750 mg/kg/day, 0.5-500 mg/kg/day, 1-250 mg/kg/day, 2.5-100 mg/kg/day, or 5-50 mg/kg/day of one or more compounds in the sialic acid pathway or derivatives thereof or a pharmaceutically acceptable salt of the foregoing; (ix) has an absolute bioavailability of about 1 to about 50%; (x) has a bioavailability based on sialic acid levels in the urine of about 0.5 to about 100%; (xi) has a mean residence time (MRT) of at least about 3.5 hours. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium strearate and microcrystalline cellulose and colloiddal silicon dioxide. In one aspect, the extended release formulation is a formulation of Table E. In yet another aspect, the extended release formulation is a formulation of Table 8.

In embodiments of any of the extended release formulations, the extended release formulation is capable of delivering to an individual in need thereof a therapeutically effective amount of one or more compounds in the sialic acid pathway or derivatives thereof over a period of greater than about any of 1, 2, 3, 4, 5, 6, 7, 8, 9, 10, 11, 12, 13, 14, 15, 16, 17, 18, 19, 20, 21, 22, 23, or 24 hours. In some embodiments, the extended release formulation is capable of delivering to an individual in need thereof a therapeutically effective amount of one or more compounds in the sialic acid pathway or derivatives thereof over a period of greater than about 12 hours or greater than about 24 hours. In embodiments of any of the extended release formulations, the extended release formulation is capable of delivering to an individual in need thereof a therapeutically effective amount of one or more compounds in the sialic acid pathway or derivatives thereof over a period of between about any of 1-24 hours, 4-24 hours, 6-24 hours, 8-24 hours, or 12-24 hours. In embodiments of any of the extended release formulations, the extended release formulation is capable of delivering to an individual in need thereof a therapeutically effective amount of one or more compounds in the sialic acid pathway or derivatives thereof over a period of about any of 1, 2, 3, 4, 5, 6, 7, 8, 9, 10, 11, 12, 13, 14, 15, 16, 17, 18, 19, 20, 21, 22, 23, or 24 hours. In some embodiments, the extended release formulation is capable of delivering to an individual in need thereof a therapeutically effective amount of one or more compounds in the sialic acid pathway or derivatives thereof over a period of about 12 hours or about 24 hours. In some embodiments, the therapeutically effective amount is delivered to the bloodstream of the individual. In some embodiments, the therapeutically effective amount is delivered to muscle tissue of the individual. In some embodiments, the one or more compounds in the sialic acid pathway or derivatives thereof include ManNAc or a derivative thereof and/or sialic acid or a derivative thereof. For example, in some embodiments, the extended release formulation is capable of delivering to an individual in need thereof a therapeutically effective amount of ManNAc and/ or sialic acid to muscle tissue of the individual over a period of between about any of 1-24 hours, 4-24 hours, 6-24 hours, 8-24 hours, or 12-24 hours. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation is capable of delivering to an individual in need thereof a substantially constant (i.e., without large burst of drug availability and deficiencies in drug availability to the blood and/or tissues of interest (e.g., muscle tissue)) therapeutically effective amount of one or more compounds in the sialic acid pathway or derivatives thereof over a period of greater than about any of 1, 2, 3, 4, 5, 6, 7, 8, 9, 10, 11, 12, 13, 14, 15, 16, 17, 18, 19, 20, 21, 22, 23, or 24 hours. In embodiments of any of the extended release formulations, the extended release formulation is capable of delivering to an individual in need thereof a substantially constant therapeutically effective amount of one or more compounds in the sialic acid pathway or derivatives thereof over a period of between about any of 1-24 hours, 4-24 hours, 6-24 hours, 8-24 hours, or 12-24 hours. In embodiments of any of the extended release formulations, the extended release formulation is capable of delivering to an individual in need thereof a substantially constant therapeutically effective amount of one or more compounds in the sialic acid pathway or derivatives thereof over a period of about any of 1, 2, 3, 4, 5, 6, 7, 8, 9, 10, 11, 12, 13, 14, 15, 16, 17, 18, 19, 20, 21, 22, 23, or 24 hours. In some embodiments, the one or more compounds in the sialic acid pathway or derivatives thereof include ManNAc or a derivative thereof and/or sialic acid or a derivative thereof. For example, in some embodiments, the extended release formulation is capable of delivering to an individual in need thereof a substantially constant therapeutically effective amount of ManNAc and/or sialic acid to muscle tissue of the individual over a period of between about any of 1-24 hours, 4-24 hours, 6-24 hours, 8-24 hours, or 12-24 hours. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation is capable of delivering to an individual in need thereof a therapeutically effective amount of one or more compounds in the sialic acid pathway or derivatives thereof with a $T_{max}$ of between about any of 2-4 hours, 3-4 hours, 6-8 hours, 6-12 hours, 6-15 hours, 12-18 hours, or 18-24 hours. In some embodiments, the extended release formulation is capable of delivering to an individual in need thereof a therapeutically effective amount of one or more compounds in the sialic acid pathway or derivatives thereof with a $T_{max}$ of about 2-4 hours. In some embodiments, the extended release formulation is capable of delivering to an individual in need thereof a therapeutically effective amount of one or more compounds in the sialic acid pathway or derivatives thereof with a $T_{max}$ of about 4-6 hours. In some embodiments, the extended release formulation is capable of delivering to an individual in need thereof a therapeutically effective amount of one or more compounds in the sialic acid pathway or derivatives thereof with a $T_{max}$ of between about 2 and about 8 hours. In some embodiments, the one or more compounds in the sialic acid pathway or derivatives thereof include ManNAc or a derivative thereof and/or sialic acid or a derivative thereof. In some embodiments, the one or more compounds in the sialic acid pathway or derivatives thereof include ManNAc and/or sialic acid. In some embodiments, the one or more compounds in the sialic acid pathway is sialic acid. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation is capable of delivering to an individual in need thereof a therapeutically effective amount of one or more compounds in the sialic acid pathway or derivatives thereof with a $C_{max}$ of about 0.5-100 µg/mL. In some embodiments, the extended release formulation is capable of delivering to an individual in need thereof a therapeutically effective amount of one or more compounds in the sialic acid pathway or derivatives thereof with a $C_{max}$ of about any one 0.5-80 µg/mL, 0.5-60 µg/mL, 0.5-40 µg/mL or 0.5-20 µg/mL. In some embodiments, the extended release formulation is capable of delivering to an individual in need thereof a therapeutically effective amount of one or more compounds in the sialic acid pathway or derivatives thereof with a $C_{max}$ of about 0.5-40 µg/mL. In some embodiments, the extended release formulation is capable of delivering to an individual in need thereof a therapeutically effective amount of one or more compounds in the sialic acid pathway or derivatives thereof with a $C_{max}$ of about any one of 0.5-35 µg/mL, 0.5-30 µg/mL, 0.5-25 µg/mL, 1-40 µg/mL, 2.5-40 µg/mL, 5-40 µg/mL, 0.5-35 µg/mL, 1-35 µg/mL, 2.5-35 µg/mL, 5-35 µg/mL, 0.5-30 µg/mL, 1-30 µg/mL, 2.5-30 µg/mL, 5-30 µg/mL, 0.5-25 µg/mL, 1-25 µg/mL, 2.5-25 µg/mL, or 5-25 µg/mL. In some embodiments, the extended release formulation is capable of delivering to an individual in need thereof a therapeutically effective amount of one or more compounds in the sialic acid pathway or derivatives thereof with a $C_{max}$ of about 0.5-20 µg/mL. In some embodiments, the extended release formulation is capable of delivering to an individual in need thereof a therapeutically effective amount of one or more compounds in the sialic acid pathway or derivatives thereof with a $C_{max}$ of about any one of 0.5-15 µg/mL, 0.5-10 µg/mL, 1-20 µg/mL, 2.5-20 µg/mL, 5-20 µg/mL, 0.5-15 µg/mL, 1-15 µg/mL, 2.5-15 µg/mL, 5-15 µg/mL, 0.5-10 µg/mL, 1-10 µg/mL, 2.5-10 µg/mL, or 5-10 µg/mL. In some embodiments, the one or more compounds in the sialic acid pathway or derivatives thereof include ManNAc and/or sialic acid. In some embodiments, the one or more compounds in the sialic acid pathway or derivatives thereof include sialic acid. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation is capable of delivering to an individual in need thereof a therapeutically effective amount of one or more compounds in the sialic acid pathway or derivatives thereof with a trough level of about 0.1-20 µg/mL. In embodiments of any of the extended release formulations, the extended release formulation is capable of delivering to an individual in need thereof a therapeutically effective amount of one or more compounds in the sialic acid pathway or derivatives thereof with a trough level of about any one of 0.1-15 µg/mL, 0.1-10 µg/mL, 0.1-5 µg/mL, 0.5-20, µg/mL, 0.5-15 µg/mL, 0.5-10 µg/mL, 0.5-5 µg/mL, 1-20 µg/mL, 1-15 µg/mL, 1-10 µg/mL, or 1-5 µg/mL or about any one of 0.1, 0.5, 1 1.5, 2, 2.5, 3, 3.5, 4, 4.5, 5, 5.5, 6, 7, 8, 9, 10, 11, 12, 13, 14 or 15 µg/mL. In some embodiments, the one or more compounds in the sialic acid pathway or derivatives thereof include ManNAc and/or sialic acid. In some embodiments, the one or more compounds in the sialic acid pathway or derivatives thereof include sialic acid. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation is capable of delivering to an individual in need thereof a therapeutically effective amount of one or more compounds in the sialic acid pathway or derivatives thereof with less than about any of 10%, 20%, 30%, 40%, 50%, 60%, or 70% excreted after one hour. In embodiments of any of the extended release formulations, the extended release formulation is capable of delivering to an individual in need thereof a therapeutically effective amount of one or more compounds in the sialic acid pathway or derivatives thereof with less than about any of 10%, 20%, 30%, 40%, 50%, 60%, 70%, 80%, or 90% excreted after four hours. In embodiments of any of the extended release formulations, the extended release formulation is capable of delivering to an individual in need thereof a therapeutically effective amount of one or more compounds in the sialic acid pathway or derivatives thereof with less than about any one of 2, 3, 4, or 5% excreted after 12 hours. In some embodiments, the one or more compounds in the sialic acid pathway or derivatives thereof include ManNAc or a derivative thereof and/or sialic acid or a derivative thereof. In some embodiments, the one or more compounds in the sialic acid pathway or derivatives thereof include ManNAc and/or sialic acid. In some embodiments, the one or more compounds in the sialic acid pathway or derivatives thereof include sialic acid. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation is capable of delivering to an individual in need thereof between about any of 0.1-50 g/day, 0.5-25 g/day, 1-15 g/day, 1-10 g/day, or 2-5 g/day of one or more compounds in the sialic acid pathway or derivatives thereof. In some embodiments, the extended release formulation is capable of delivering to an individual in need thereof between about 2 g/day and 5 g/day of one or more compounds in the sialic acid pathway or derivatives thereof. In embodiments of any of the extended release formulations, the extended release formulation is capable of delivering to an individual in need thereof between about any of 0.01-750 mg/kg, 0.5-500 mg/kg, 1-250 mg/kg, 2.5-100 mg/kg, or 5-50 mg/kg of one or more compounds in the sialic acid pathway or derivatives thereof. In some embodiments, the extended release formulation is capable of delivering to an individual in need thereof between about 5 mg/kg and 50 mg/kg of one or more compounds in the sialic acid pathway or derivatives thereof. In some embodiments, the one or more compounds in the sialic acid pathway or derivatives thereof include ManNAc or a derivative thereof and/or sialic acid or a derivative thereof. For example, in some embodiments, the extended release formulation is capable of delivering to an individual in need thereof between about 5 mg/kg and 50 mg/kg of ManNAc and/or sialic acid. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation is capable of delivering to an individual in need thereof between about any of 0.01-750 mg/kg/day, 0.5-500 mg/kg/day, 1-250 mg/kg/day, 2.5-100 mg/kg/day, or 5-50 mg/kg/day of one or more compounds in the sialic acid pathway or derivatives thereof. In some embodiments, the extended release formulation is capable of delivering to an individual in need thereof between about 5 mg/kg/day and 50 mg/kg/day of one or more compounds in the sialic acid pathway or derivatives thereof. In some embodiments, the one or more compounds in the sialic acid pathway or derivatives thereof include ManNAc or a derivative thereof and/or sialic acid or a derivative thereof. For example, in some embodiments, the extended release formulation is capable of delivering to an individual in need thereof between about 5 mg/kg/day and 50 mg/kg/day of ManNAc and/or sialic acid. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation has an absolute bioavailability of about 1-50%. In some embodiments, the extended release formulation has an absolute bioavailability of about any one of 1-45%, 1-40%, 1-35%, 1-30%, 1-20%, 1-10%. In some embodiments the extended release formulation has an absolute bioavailability of about 1-25%. In some embodiments, the extended release formulation has an absolute bioavailability of about any one of 5, 10, 15, 20, 25 or 50%. In some embodiments, the one or more compounds in the sialic acid pathway or derivatives thereof include ManNAc or a derivative thereof and/or sialic acid or a derivative thereof. In some embodiments, the one or more compounds in the sialic acid pathway or derivatives thereof include sialic acid or a derivative thereof. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation has a bioavailability based on sialic acid levels in the urine of about 0.5-100%. In some embodiments, the extended release formulation has a bioavailability based on sialic acid levels in the urine of about any one of 0.5-2.5%, 1-2.5%, 2-8%, 2-12%, 2.5-20%, 2.5-40%, 2.5-80%, 2.5-100%. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation has a mean residence time (MRT) of at least about 3.5 hours. In some embodiments, the extended release formulation has a MRT of at least about any one of 3, 4, 4.5, 5, 5.5 or 6 hours. In some embodiments, the one or more compounds in the sialic acid pathway or derivatives thereof include ManNAc or a derivative thereof and/or sialic acid or a derivative thereof. In some embodiments, the one or more compounds in the sialic acid pathway or derivatives thereof include sialic acid or a derivative thereof. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

The extended release pharmaceutical formulation may be formulated for parenteral administration (e.g., by injection, for example, bolus injection or continuous infusion) and may be presented in unit dose form in ampoules, pre-filled syringes, small volume infusion containers or in multi-dose containers. The extended release pharmaceutical formulation may be may form suspensions, solutions, or emulsions in oily or aqueous vehicles. Alternatively, the one or more compounds in the sialic acid biosynthetic pathway or derivative thereof and other ingredients may be in powder form, obtained by aseptic isolation of sterile solid or by lyophilization from solution, for constitution with a suitable vehicle, e.g., sterile, pyrogen-free water, before use.

For topical administration, the extended release pharmaceutical formulation may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. The extended release pharmaceutical formulation may be delivered via patches or bandages for dermal administration. Ointments and creams may, for example, be formulated with an aqueous or oily base with the addition of suitable thickening and/or gelling agents. Drops, such as eye drops or nose drops, may be formulated with the one or more compounds in the sialic acid biosynthetic pathway or derivative thereof in an aqueous or non-aqueous base. Liquid sprays are conveniently delivered from pressurized packs. Drops can be delivered via a simple eye dropper-capped bottle, or via a plastic bottle adapted to deliver liquid contents dropwise, via a specially shaped closure.

Further, in some embodiments, the extended release pharmaceutical formulation comprising one or more compounds in the sialic acid biosynthetic pathway or derivative thereof may also be used in combination with other therapeutic agents.

Methods of Making Extended Release Formulations

Methods of making extended release formulations detailed herein are also provided. In one aspect, the formulation components (which may optionally be delumped and sieved to a desired range of particle size) are combined and mixed to provide a uniform formulation blend, which may further be used to prepare particular dosage forms, such as tablets or capsules, e.g., for oral administration. Particular dosage forms, once prepared, may be further modified to provide the final drug product, such as, e.g., by administering a coating to a tablet formed from an extended release formulation blend. Preparation of the extended release formulations may be accomplished through known techniques, such as direct compression, dry granulation and wet granulation.

Direct compression may be accomplished by delumping the formulation components and sieving to a desired range of particle size, which may be the same or different size for individual formulation components. The components are then blended, which may be accomplished by one or a series of blending steps until all formulation components are blended. The blended formulation may, if desired, be direct compressed to provide the desired product, which may be in the form of a dosage suitable for oral administration, such as a tablet. The blended formulation may also be filled into capsules or other forms for solid-dosage administration, e.g., for oral administration.

Dry granulation may also be utilized to prepare the extended release formulations detailed herein, and may be used to improve the flow or other characteristic of a blend of formulation components to be formed into a final drug product. One example of dry granulation includes delumping and/or sieving the formulation components, blending the formulation components and feeding the blend through, e.g., a roller compactor that produces a ribbon of compressed product, then milling the resulting ribbon. The milled product may then be compressed as detailed above or further blended with additional formulation components and compressed.

Wet granulation may also be utilized to prepare the extended release formulations. For example, the formulation components may be delumped and sieved to the desired size, and blended. The resulting blend may be added to an appropriate fluid bed processor equipped with a spray gun for fluidizing the blended formulation components using standard practices. The resulting granulation is dried (e.g., in the fluid bed) and milled to a desired range of particle sized and may be used for preparation of a final formulation. Wet granulation may also utilize high shear wet granulation (blended components are mixed, and frequently chopped while the solvent, typically water or other aqueous-based solvent, is sprayed over the mass during granulation).

Extended release formulations that are in tablet form preferably are compressed to a sufficient hardness to prevent premature ingress of a medium (e.g., aqueous medium) and to prevent surface pitting and breakage during coating, when applicable.

It is understood that extended release formulation blends are provided, such as a final formulation blend comprising a therapeutic agent and all formulation components in a final product (e.g., a blend comprising a therapeutic agent, a polymer, an excipient and a lubricant) as well as intermediate formulation blends that contain a portion of all formulation components in a final product (e.g., a blend comprising a therapeutic agent and a polymer but not an excipient or a lubricant, where the final product contains an excipient and a lubricant).

Methods of Treating and Preventing Sialic Acid Deficiencies

Provided herein are also methods of treating and/or preventing sialic acid deficiencies in an individual in need thereof by administering an effective amount of one or more compounds in the sialic acid pathway or derivatives thereof in any extended release formulation described herein. The methods may comprise administration of an effective amount of any of the formulations detailed herein, including any of the formulations under the heading "Extended Release Formulations," including but not limited to any of the formulations of Tables A-E. Thus, although certain formulations are detailed below, it is understood that any extended release formulations described herein may be employed in any of the methods provided herein. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium strearate and microcrystalline colludose and colloiddal silicon dioxide. In one aspect, the extended release formulation is a formulation of Table E. In yet another aspect, the extended release formulation is a formulation of Table 8. In some embodiments, the one or more compounds in the sialic acid pathway or derivatives thereof include ManNAc or a derivative thereof and/or sialic acid or a derivative thereof. For example, provided herein are methods of treating and/or preventing sialic acid deficiencies in an individual in need thereof by administering an effective amount of ManNAc and sialic acid in any extended release formulation described herein. In some embodiments, the methods of treating and/or preventing sialic acid deficiencies increase sialic acid production. In some embodiments, the methods of treating and/or preventing sialic acid deficiencies increase sialylation of effected tissue. In some embodiments, the method of treating and/or preventing sialic acid deficiencies comprises administering an extended release formulation comprising a drug load of about 30-60% (e.g., sialic acid and/or ManNAc), about 20-30% w/w hypromellose (e.g. hypromellose Type 2208 or Methocel K100M), about 20-25% w/w sodium alginate (e.g. Protanal), about 1-5% w/w lamda carrageenan (e.g. Viscarin GP-209), about 1-10% w/w of microcrystalline cellulose and colloidal silicon dioxide (e.g., Prosolv® SMCC HD90), about 0.1-1% w/w/magnesium stearate (e.g. HyQual®), and about 1-5% of an enteric coating (e.g. Opadry® II White). In some embodiments, the method of treating or preventing sialic acid deficiencies comprises administering an extended release formulation comprising a drug load of about 30-60% (e.g., sialic acid and/or ManNAc), about 20-30% w/w polyethylene oxide (e.g. Polyox WSR), about 20-25% w/w sodium alginate (e.g. Protanal), about 1-5% w/w lamda carrageenan (e.g. Viscarin GP-209), about 1-10% w/w of microcrystalline cellulose and colloidal silicon dioxide (e.g., Prosolv® SMCC HD90), about 0.1-1% w/w/magnesium stearate (e.g. HyQual®), and about 1-5% of an enteric coating (e.g. Opadry® II White).

Provided herein are also methods of increasing production of sialic acid (e.g., increasing production of sialic acid in muscle tissue) and the proximate substrate for glycosylation, CMP-sialic acid in an individual in need thereof by administering an effective amount of one or more compounds in the sialic acid pathway or derivatives thereof in any extended release formulation described herein. In some embodiments, the one or more compounds in the sialic acid pathway or derivatives thereof include ManNAc or a derivative thereof and/or sialic acid or a derivative thereof. For example, provided herein are methods of increasing production of sialic acid (e.g., increasing production of sialic acid in muscle tissue) in an individual in need thereof by administering an effective amount of ManNAc and sialic acid in any extended release formulation described herein.

Provided herein are also methods of increasing sialylation of muscle tissue in an individual in need thereof by administering an effective amount of one or more compounds in the sialic acid pathway or derivatives thereof in any extended release formulation described herein. In some embodiments, the one or more compounds in the sialic acid pathway or derivatives thereof include ManNAc or a derivative thereof and/or sialic acid or a derivative thereof. For example, provided herein are methods of increasing sialylation of muscle tissue in an individual in need thereof by administering an effective amount of ManNAc and sialic acid in any extended release formulation described herein.

Provided herein are also methods of improving muscle function in an individual in need thereof by administering an effective amount of one or more compounds in the sialic acid pathway or derivatives thereof in any extended release formulation described herein. In some embodiments, the one or more compounds in the sialic acid pathway or derivatives thereof include ManNAc or a derivative thereof and/or sialic acid or a derivative thereof. For example, provided herein are methods of improving muscle function in an individual in need thereof by administering an effective amount of ManNAc and sialic acid in any extended release formulation described herein.

Sialic acids are important for proper development and functioning of many organs and tissues, and a deficiency of sialic acid can give rise to many different types of diseases and conditions. Other types of muscle diseases have also shown that glycosylation is important for muscle function. Nishino and Ozawa, Curr. Opin. Neurol. 15:539-544 (2002). In some embodiments, the sialic acid deficiency is a myopathy, muscular atrophy and/or muscular dystrophy. Myopathies that can be treated with the present compositions and methods also include distal myopathy with rimmed vacuoles (Nonaka myopathy) and the muscular dystrophy hereditary inclusion body myopathy (HIBM). In some embodiments, the methods of treating and/or preventing increase sialylation of muscle tissue. In some embodiments, the methods of treating and/or preventing improve muscle function and reduce muscle injury from physical activity, as measures by creatine kinase plasma levels after exercise. In some embodiments, the methods of treating or preventing muscle dysfunction will improve independent ambulation, stair climbing, foot drop, getting up from a chair and walking, hand grip and manipulation and pulmonary function. In some embodiments, the method further comprises identifying an individual in need thereof by determining genotype or expression levels of the gene GNE.

In some embodiments, the sialic acid deficiency is a kidney condition and diseases (e.g., those involving proteinuria and hematuria). Proteinuria involves leakage of protein from the blood into the urine. If the amount of protein in the urine is very high, this condition is often called nephrotic syndrome. Several types of diseases exhibit the symptoms of proteinuria, including high blood pressure, infections, reflux nephropathy, diabetes, and various types of glomerulonephritis, including minimal change nephrosis. Hematuria simply means blood in the urine (e.g., gross hematuria or microscopic hematuria). In some embodiments, the methods of treating and/or preventing increase sialylation of kidney tissue.

In embodiments of any of the methods, a therapeutically effective amount of one or more compounds in the sialic acid pathway or derivatives thereof is provided over a period of greater than about any of 1, 2, 3, 4, 5, 6, 7, 8, 9, 10, 11, 12, 13, 14, 15, 16, 17, 18, 19, 20, 21, 22, 23, or 24 hours. In some embodiments, a therapeutically effective amount of one or more compounds in the sialic acid pathway or derivatives thereof is provided over a period of greater than about 12 hours or greater than about 24 hours. In embodiments of any of the methods, a therapeutically effective amount of one or more compounds in the sialic acid pathway or derivatives thereof is provided over a period of between about any of 1-24 hours, 4-24 hours, 6-24 hours, 8-24 hours, or 12-24 hours. In embodiments of any of the methods, a therapeutically effective amount of one or more compounds in the sialic acid pathway or derivatives thereof is provided over a period of about any of 1, 2, 3, 4, 5, 6, 7, 8, 9, 10, 11, 12, 13, 14, 15, 16, 17, 18, 19, 20, 21, 22, 23, or 24 hours. In some embodiments, a therapeutically effective amount of one or more compounds in the sialic acid pathway or derivatives thereof is provided over a period of about 12 hours or about 24 hours. In some embodiments, the therapeutically effective amount is provided to the bloodstream of the individual. In some embodiments, the therapeutically effective amount is provided to muscle tissue of the individual. In some embodiments, the one or more compounds in the sialic acid pathway or derivatives thereof include ManNAc or a derivative thereof and/or sialic acid or a derivative thereof. For example, in some embodiments, a therapeutically effective amount of ManNAc and/or sialic acid is provided to muscle tissue of the individual over a period of between about any of 1-24 hours, 4-24 hours, 6-24 hours, 8-24 hours, or 12-24 hours.

In embodiments of any of the methods, the individual in need thereof is provided a substantially constant (i.e., without large burst of drug availability and deficiencies in drug availability to the blood and/or tissues of interest (e.g., muscle tissue)) therapeutically effective amount of one or more compounds in the sialic acid pathway or derivatives thereof over a period of greater than about any of 1, 2, 3, 4, 5, 6, 7, 8, 9, 10, 11, 12, 13, 14, 15, 16, 17, 18, 19, 20, 21, 22, 23, or 24 hours. In embodiments of any of the methods, the individual in need thereof is provided a substantially constant therapeutically effective amount of one or more compounds in the sialic acid pathway or derivatives thereof over a period of between about any of 1-24 hours, 4-24 hours, 6-24 hours, 8-24 hours, or 12-24 hours. In embodiments of any of the methods, the individual in need thereof is provided a substantially constant therapeutically effective amount of one or more compounds in the sialic acid pathway or derivatives thereof over a period of about any of 1, 2, 3, 4, 5, 6, 7, 8, 9, 10, 11, 12, 13, 14, 15, 16, 17, 18, 19, 20, 21, 22, 23, or 24 hours. In some embodiments, the one or more compounds in the sialic acid pathway or derivatives thereof include ManNAc or a derivative thereof and/or sialic acid or a derivative thereof. For example, in some embodiments, the individual in need thereof is provided a substantially constant therapeutically effective amount of ManNAc and/or sialic acid to muscle tissue of the individual over a period of between about any of 1-24 hours, 4-24 hours, 6-24 hours, 8-24 hours, or 12-24 hours.

In embodiments of any of the methods, the individual in need thereof is provided a therapeutically effective amount of one or more compounds in the sialic acid pathway or derivatives thereof with a $T_{max}$ of between about any of 2-4 hours, 3-4 hours, 6-8 hours, 6-12 hours, 6-15 hours, 12-18 hours, or 18-24 hours. In some embodiments, the one or more compounds in the sialic acid pathway or derivatives thereof include ManNAc or a derivative thereof and/or sialic acid or a derivative thereof. In some embodiments, the one or more compounds in the sialic acid pathway or derivatives thereof include ManNAc and/or sialic acid.

In embodiments of any of the methods, less than about any of 10%, 20%, 30%, 40%, 50%, 60%, or 70% of one or more compounds in the sialic acid pathway or derivatives thereof is excreted from the individual after one hour. In embodiments of any of the methods, less than about any of 10%, 20%, 30%, 40%, 50%, 60%, 70%, 80%, or 90% of one or more compounds in the sialic acid pathway or derivatives thereof is excreted from the individual after four hours. In some embodiments, the one or more compounds in the sialic acid pathway or derivatives thereof include ManNAc or a derivative thereof and/or sialic acid or a derivative thereof. In some embodiments, the one or more compounds in the sialic acid pathway or derivatives thereof include ManNAc and/or sialic acid.

In embodiments of any of the methods, the one or more compounds in the sialic acid pathway or derivatives thereof are administered to an individual in need thereof between about any of 0.1-50 g/day, 0.5-25 g/day, 1-15 g/day, 1-10 g/day, 2-5 g/day, 0.2-25 g/day, 0.3-12 g/day, 0.4-10 g/day, 0.5-8 g/day, and 0.7-6 g/day. In some embodiments, the one or more compounds in the sialic acid pathway or derivatives thereof are administered between about 2 g/day and 5 g/day. In embodiments of any of the methods, the one or more compounds in the sialic acid pathway or derivatives thereof are administered to an individual in need thereof between about any of 0.01-750 mg/kg, 0.5-500 mg/kg, 1-250 mg/kg, 2.5-100 mg/kg, or 5-50 mg/kg. In some embodiments, the one or more compounds in the sialic acid pathway or derivatives thereof are administered to an individual in need thereof between about 5 mg/kg and 50 mg/kg. In some embodiments, the one or more compounds in the sialic acid pathway or derivatives thereof include ManNAc or a derivative thereof and/or sialic acid or a derivative thereof. For example, in some embodiments, ManNAc and/or sialic acid are administered to an individual in need thereof between about 5 mg/kg and 50 mg/kg.

In embodiments of any of the methods, the one or more compounds in the sialic acid pathway or derivatives thereof are administered to an individual in need thereof between about any of 0.01-750 mg/kg/day, 0.5-500 mg/kg/day, 1-250 mg/kg/day, 2.5-100 mg/kg/day, or 5-50 mg/kg/day. In some embodiments, the one or more compounds in the sialic acid pathway or derivatives thereof are administered to an individual in need thereof between about 5 mg/kg/day and 50 mg/kg/day. In some embodiments, the one or more compounds in the sialic acid pathway or derivatives thereof include ManNAc or a derivative thereof and/or sialic acid or a derivative thereof. For example, in some embodiments, ManNAc and/or sialic acid are administered to an individual in need thereof between about 5 mg/kg/day and 50 mg/kg/day.

In some embodiments, the effective amount of one or more compounds in the sialic acid pathway or derivatives thereof in any extended release formulation is administered once a day, twice a day, three times a day, or four times a day.

The amount of the extended release formulation according to an embodiment of the invention to be administered to a human body may be appropriately selected in accordance with the absorption rate in the body, rate of inactivation, rate of excretion, the age, gender and condition of the patient, severity of the disease, or the like. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of one or more compounds in the sialic acid pathway or derivatives thereof may be essentially continuous over a pre-selected period of time or may be in a series of spaced doses. Both local and systemic administration is contemplated.

Unit Dosages and Articles of Manufacture

Also provided herein are articles of manufacture and unit dosages which include the extended release formulations comprising one or more compounds in the sialic acid pathway or derivatives thereof described herein.

Provided herein are articles of manufacture or kits comprising: (a) a container comprising the extended release pharmaceutical formulation comprising one or more compounds in the sialic acid biosynthetic pathway or derivative thereof described herein; and (b) a package insert with instructions for treating and/or preventing a sialic acid deficiency in a patient. In some embodiments, the one or more compounds in the sialic acid pathway or derivatives thereof include ManNAc or a derivative thereof and/or sialic acid or a derivative thereof.

The article of manufacture comprises a container and a label or package insert on or associated with the container. Suitable containers include, for example, bottles, vials, syringes, etc. The containers may be formed from a variety of materials such as glass or plastic. The container holds or contains a formulation and may have a sterile access port (for example the container may be an intravenous solution bag or a vial having a stopper pierceable by a hypodermic injection needle). At least one active agent in the composition is the polypeptide. The label or package insert indicates that the composition's use in a subject with specific guidance regarding dosing amounts and intervals of polypeptide and any other drug being provided. The article of manufacture may further include other materials desirable from a commercial and user standpoint, including other buffers, diluents, filters, needles, and syringes. In some embodiments, the container is a syringe. In some embodiments, the syringe is further contained within an injection device. In some embodiments, the injection device is an autoinjector.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products.

Provided herein are also unit dosages which include the extended release formulations comprising one or more compounds in the sialic acid pathway or derivatives thereof. In some embodiments, the one or more compounds in the sialic acid pathway or derivatives thereof include ManNAc or a derivative thereof and/or sialic acid or a derivative thereof.

Unit dosage forms comprising any of the extended release formulations described herein, including but not limited to those formulations detailed under the heading "Extended Release Formulations," such as any of the formulations of Tables A-E, are described. These unit dosage forms can be stored in a suitable packaging in single or multiple unit dosages and may also be further sterilized and sealed. For convenience and ease of patient compliance, the extended release formulations may be delivered in the form of unit dosage forms, which may be administered to an individual. In one variation, the extended release formulation is a solid substance and unit dosage forms thereof may be prepared in the form of tablets, capsules, sachets and chewable tablets. In one aspect, the dosage form is in the form of a capsule or tablet, preferably in the form of a tablet.

The preparation of the unit forms generally involves a step of preparing a blend filling, either by volume or weight. For example, in production of tablets and capsules, the extended release formulation blend is volume filled into a die or capsule, respectively. In one aspect, a batch of unit dosage forms has the same potency (amount of drug per unit dosage form) within an allowable margin, which in one variation is a relative standard deviation (RSD) of less than 6% and in another variation is less than 8.0 or 7.8%.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1

Human myoblasts are obtained from an HIBM patient and grown and differentiated into myotubes. After an appropriate washout, the cells are placed in protein free or sialic acid free medium and then treated with differing concentrations of sialic acid, ManNAc, or both for different periods of time. At time points 0 (before supplementation), 2 hours, 8 hours, 16 hours, and 24 hours after the start (and different times after removal of replacement substrates from each culture), internal sialic acid, CMP-sialic, and glycosylation of newly synthesized proteins are measured. Glycosylation replacement after 24 hours is evaluated and a time course is also determined for glycosylation with replacement, runs out of substrate, and stops glycosylating.

Example 2

Human HIBM myoblasts are obtained and differentiated into myotubes as described in Example 1 and this time, a matrix of sialic acid and N-acetylmannosamine is given for either short bursts of 1-2 hours or longer periods of 4 and 8 hours. The onset of normalization of sialylation and the peak efficiency is evaluated, as well as the time to decline of normal sialylation. Efficacy of single and combination formulations in replacement treatment and effective time are determined.

Example 3

A large variety of human fibroblasts from HIBM patients are obtained with different mutations and clinical phenotypes. Each line is titrated to its 50% maximal correction with sialic acid and ManNAc independently. Replacement efficacy is evaluated for different lines from different patients.

Example 4

A mouse model of HIBM is treated with either standard sialic acid or ManNAc or given both compounds together. An additional group is given these items in an extended release formulation. The mice are evaluated using the procedure described in Malicdan et al., *Nat. Medicine* 15(6): 690-695 (2009) for muscle strength and clinical outcome. In addition, mice are analyzed at different time points after a dose and during treatment to assess glycosylation and intermediates in the muscle tissues. Clinical effect and the best steady state restoration of intermediates are evaluated.

Example 5

To assess the minimal concentration of sialic acid metabolite required to maintain sialylation optimally, myoblasts, myotubes or human fibroblasts are cultured in sialic acid free medium until they reach an abnormal level of sialylation at steady state. A series of concentrations to these cultures are added and evaluated for the restoration of glycosylation. Concentration in the medium required at steady state to replace the missing sialylation is determined.

This concentration provides a target for a minimum plasma concentration within patients treated with an extended release formulation.

Example 6

Preparation of Sialic Acid 250 mg Strength Tablets Using Dry Blend Method of Manufacture Experimental/Materials Sialic Acid (Food & Bio Research center, Inc. Kyoto Japan) was stored in aluminum foil bags at −20 C. However, handling and processing of prototypes were all under ambient room temperature. In-process materials and bulk tablets were stored in double polyethylene bags with desiccant. The sialic acid was evaluated for physical properties consisting of morphology, particle size by sieve analysis, bulk and tap density.

50 gram lab-scale batches were prepared using bag-blending, manual filling and hand turning of the tablet press to compress tablets to evaluate dissolution as the first level of screening. Tablets were manufactured using the ProCR platform. Their formulas are listed below in Table 1 and 2.

TABLE 1

Quantitative Formula for Sialic Acid, ProCR Hypromellose 250 mg Tablets:

| Ingredient | Vendor | mg/Tablet | % w/w | g/batch |
|---|---|---|---|---|
| Sialic Acid (N-Acetylneuraminic acid) | Food and BioResearch Center, Inc | 249.75 | 33.3 | 16.65 |
| Hypromellose, Type 2208 (Methocel ® K100M Premium CR) | Colorcon | 225.0 | 30.0 | 15.0 |
| Sodium Alginate (Protanal ® LF 120M) | FMC Biopolymer | 187.5 | 25.0 | 12.5 |
| Carrageenan (Viscarin GP-209) | FMC Biopolymer | 37.5 | 5.0 | 2.5 |
| Microcrystallline Cellulose and Colloidal Silicon Dioxide (ProSolv ® SMCC HD 90) | JRS Pharma | 46.5 | 6.2 | 3.1 |
| Magnesium Stearate (HyQual ®), Vegatable Source Product Code 2257 | Mallinckrodt | 3.75 | 0.5 | 0.25 |
| Total | | 750 | 100% | 50 |

TABLE 2

Quantitative Formula for Sialic Acid ProCR Polyox, 250 mg Tablets:

| Ingredient | Vendor | mg/Tablet | % w/w | g/batch |
|---|---|---|---|---|
| Sialic Acid (N-Acetylneuraminic acid) | Food and BioResearch Center, Inc | 249.75 | 33.3 | 16.65 |
| Polyethylene Oxide WSR (Polyox) | Dow Chemical Company | 225.0 | 30.0 | 15.0 |
| Sodium Alginate (Protanal ® LF 120M) | FMC Biopolymer | 187.5 | 25.0 | 12.5 |
| Carrageenan (Viscarin GP-209) | FMC Biopolymer | 37.5 | 5.0 | 2.5 |
| Microcrystallline Cellulose and Colloidal Silicon Dioxide (ProSolv ® SMCC HD 90) | JRS Pharma | 46.5 | 6.2 | 3.1 |

TABLE 2-continued

Quantitative Formula for Sialic Acid
ProCR Polyox, 250 mg Tablets:

| Ingredient | Vendor | mg/Tablet | % w/w | g/batch |
|---|---|---|---|---|
| Magnesium Stearate (HyQual ®), Vegatable Source Product Code 2257 | Mallinckrodt | 3.75 | 0.5 | 0.25 |
| Total | | 750 | 100 | 50 |

Sialic Acid, hypromellose Type 2208, sodium alginate, carrageenan and microcrystalline cellulose with colloidal silicon dioxide were delumped using a #20 USA standard sieve and weighed per the quantitative formula. The ingredients were combined in a small ziplock bag and blended for 15 minutes. Magnesium stearate was delumped using a #40 USA standard screen, weighed per quantitative formula, and added to the blended ingredients in the bag. The ingredients were blended for an additional three minutes. The final blends, as well as the un-sieved sialic acid were characterized using bulk density, tap density, particle size sieve analysis, Carr's Compressibility Index, and minimum critical orifice. The final blend of each prototype was compressed on the Korsch PH100 tablet press. The resulting tablets were submitted to the analytical lab for dissolution testing.

Sialic Acid Characterization

Figure 2:
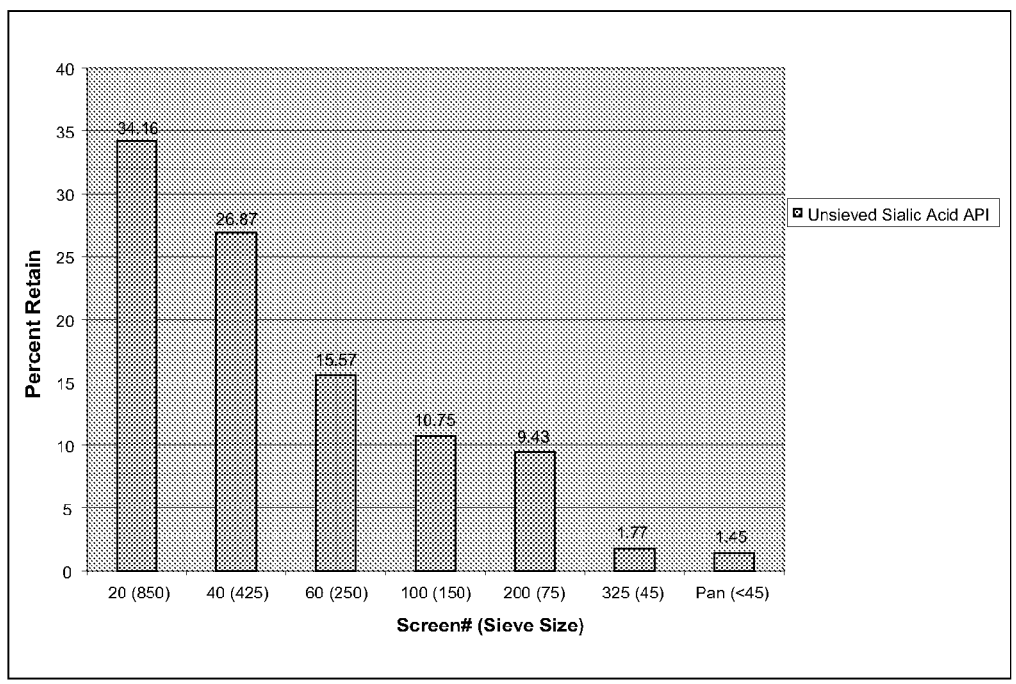
FIG. 2 shows the particle size distribution for sialic acid.

Sialic Acid was visually characterized as a white fluffy powdery substance. Its bulk density was 0.293 g/mL, and its tap density was 0.419 g/ml. The Carr's Compressibility Index was 30%, and the minimum critical orifice diameter was 18 mm. The particle size sieve analysis of Sialic Acid (Table 3) revealed a distribution of coarse and midsize particles as shown in FIG. 2. The sialic acid was sized prior to blending to facilitate blend homogeneity.

TABLE 3

Particle Size Distribution for Sialic Acid

| Sieve # (Mesh size (um)) | Unsieved Sialic Acid (N-Acetylneuraminic acid) |
|---|---|
| 20 (850) | 34.16 |
| 40 (425) | 26.87 |
| 60 (250) | 15.57 |
| 100 (150) | 10.75 |
| 200 (75) | 9.3 |
| 325 (45) | 1.77 |
| Pan (<45) | 1.45 |

ProCR Sialic Acid, 250 mg CR Tablets

Figure 3:
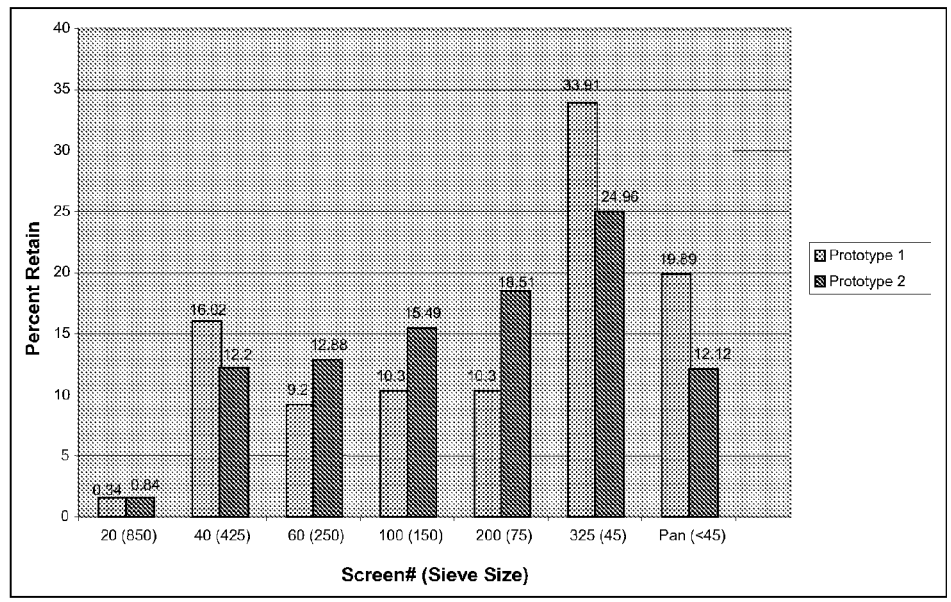
FIG. 3 shows the particle size distribution plot for ProCR sialic acid 250 mg final blends.

Both prototype blends, ProCR hypromellose and ProCR Polyox, were compressed into tablets using 0.3300×0.7100 inch modified oval tooling targeting a tablet weight of 750 mg and a hardness range of 17 to 20 Kp. During tableting, powder bridging in the die cavity was observed for ProCR hypromellose. This was an indication that the blend needed to be densified to improve flowability on the tablet press. ProCR Polyox appeared denser and seemed to flow better on the tablet press. However, its Carr's Compressibility Index and minimum critical orifice diameter results, as shown in Table 4, indicated that it also needed further processing such as, granulation. The particle size distribution of the Polyox prototype seemed to be more dispersed over various screen sizes than the hypromellose prototype shown in Table 5 and FIG. 3.

TABLE 4

Physical Characterization Results of Sialic Acid 250 mg

| Powder | Bulk Density (g/mL) | Tap Density (g/mL) | Carr's Compressibility Index (%) | Flodex Critical Orifice (mm) |
|---|---|---|---|---|
| Sialic Acid (N-Acetylneuraminic acid) | 0.293 | 0.419 | 30 (poor flow) | 18 |
| Prototype 1 (Hypromellose) | 0.359 | 0.543 | 33.8 (very poor flow) | 20 |
| Prototype 2 (Polyox) | 0.439 | 0.716 | 38.7 (very very poor flow) | 18 |

TABLE 5

Particle Size Distribution for ProCR Sialic Acid, 250 mg Tablets.

| Sieve # (Mesh size (um)) | Prototype 1 with Hypromellose % Retain | Prototype 2 with Polyethylene oxide % Retain |
|---|---|---|
| 20 (850) | 0.34 | 0.84 |
| 40 (425) | 16.02 | 15.20 |
| 60 (250) | 9.2 | 12.88 |
| 100 (150) | 10.3 | 15.49 |
| 200 (75) | 10.3 | 18.51 |
| 325 (45) | 33.91 | 24.96 |
| Pan (<45) | 19.89 | 12.12 |

Figure 4:
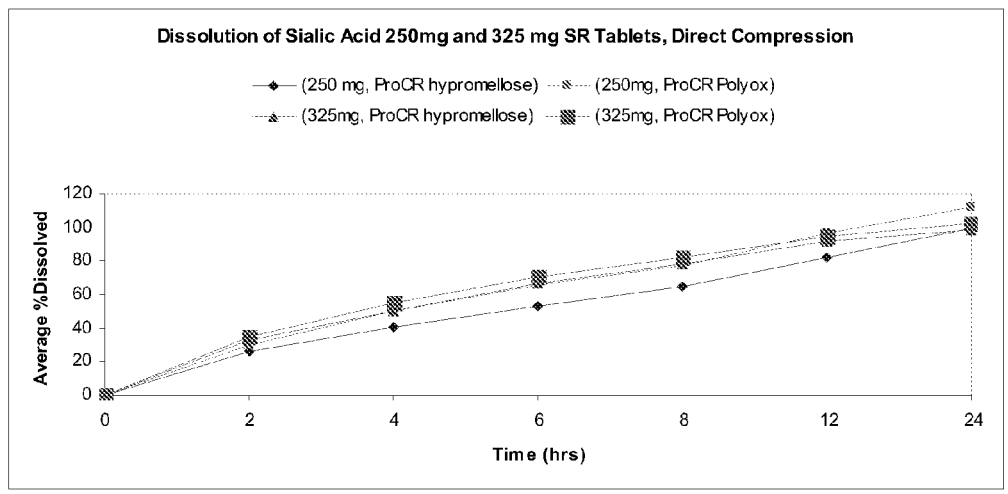
FIG. 4 shows the dissolution plot of sialic acid 250 and 325 mg sustained release (SR) tablets by direct compression

The compression of the tablets resulted in a weight range of 3-5% of the target of 750 mg. The variability was primarily due to the manual filling and poor flow. Regardless of the weight variability, the tablet appearance and hardness was good, ranging from 13 to 18 Kp, as listed in Table 6. The dissolution results showed a first order sustained release profile over a 12 hour period, as shown in Table 7 and FIG. 4.

TABLE 6

Physical Data of Sialic Acid 250 and 325 mg Tablets

| Test | Hypromellose 250 mg Tablets | Polyox 250 mg Tablets | Hypromellose 325 mg Tablets | Polyox 325 mg Tablets |
|---|---|---|---|---|
| Tablet Weight (mg) | 744-787 | 746-751 | 747-766 | 745-771 |
| Tablet Thickness (in) | 0.268-0.271 | 0.261-0.263 | 0.291-0.295 | 0.283-0.286 |
| Tablet Hardness (kp) | 17.5 | 18.3 | 13.2 | 13.0 |
| Tablet Friability (%) | ND | ND | ND | ND |

ND: Not determined

TABLE 7

Dissolution Results of Direct Compression Prototypes

| Test Dissolution (Average n = 3) % Release | Hypromellose 250 mg Tablets | Polyox 250 mg Tablets | Hypromellose 325 mg Tablets | Polyox 325 mg Tablets |
|---|---|---|---|---|
| 2 hr | 26 | 30 | 33 | 35 |
| 4 hr | 41 | 50 | 50 | 55 |
| 6 hr | 53 | 66 | 67 | 71 |
| 8 hr | 65 | 77 | 78 | 82 |
| 12 hr | 82 | 97 | 92 | 95 |
| 16 hr* | — | — | 99 | 103 |
| 24 hr | 100 | 112 | — | — |

*Represented as last time point in graph

Example 7

Preparation of Sialic Acid 325 and 500 mg Development Prototypes

Initially, two small 50 gram dry blend batches were manufactured with an increased drug load from 33% w/w to 43% w/w to verify that the drug release profile was acceptable. The two compositions are listed in Table 8 as hypromellose and Polyox. The tabletting was done as described before using a manual fill into the die cavity.

TABLE 8

Quantitative Formula for Sialic Acid 325 mg and 500 mg sustained release Tablets Prototypes:

| Ingredient | Vendor | mg/Tablet ProCR Hypromellose | mg/Tablet ProCR Polyox | % w/w | g/batch 50 g size | g/batch 1800 g size |
|---|---|---|---|---|---|---|
| Sialic Acid (N-Acetylneuraminic acid) | Food and BioResearch Center, Inc | 325.0 | 325.0 | 43.3 | 21.65 | 779.4 |
| Hypromellose, Type 2208 (Methocel ® K100 M Premium CR) | Colorcon | 191.3 | — | 25.5 | 12.75 | 459 |
| Polyethylene Oxide WSR (Polyox) | | — | 191.3 | 25.5 | 12.75 | 459 |
| Sodium Alginate (Protanal ® LF 120M) | FMC Biopolymer | 159.0 | 159.0 | 21.2 | 10.60 | 381.6 |
| Carrageenan (Viscarin GP-209) | FMC Biopolymer | 31.5 | 31.5 | 4.2 | 2.10 | 75.6 |
| Microcrystallline Cellulose and Colloidal Sillicon Dioxide (ProSolv ® SMCC HD 90) | JRS Pharma | 39.8 | 39.8 | 5.3 | 2.65 | 95.4 |
| Magnesium Stearate (HyQual ®), Vegatable Source Product Code 2257 | Mallinckrodt | 3.8 | 3.8 | 0.5 | 0.25 | 9.0 |
| Total for 325 mg Strength | | 750.4 | 750.4 | 100 | 50 | 1800 |
| Total for 500 mg Strength | | 1154.5 | 1154.8 | 100 | — | — |

Wet Granulation Method of Manufacture

In order to avoid bridging and poor flow during compression batch sizes were scaled up from 50 grams to 1800 grams, and a high shear granulation method of manufacture was used to produce 325 and 500 mg dose strengths while maintaining good tablet compression properties. The 325 and 500 mg dose strengths shared a common blend that was divided prior to compression. Two tablet sizes were produced: A 325 mg dose strength tablet with a length of 17.7 mm, a width of 9.1 mm and a thickness of 6.7 mm; and a 500 mg dose strength tablet with a length of 19.3 mm, a width of 9.7 mm and a thickness of 8.0 mm). The following equipment and process were used to make these tables.

Experimental/Materials

All raw materials were used as received from vendors as listed in Table 8. The batch size was 1800 grams. The following equipment was used:
Fielder PP1 High Shear Granulator
Niro-Aeromatic MP-1 Multi-processor
FitzMill JT Homoloid equipped with knives forward, 0.079" round hole screen
4 Qt PK Blender
Korsch PF1100 tablet Press equipped with 0.350"×0.6875" modified oval tooling for the 750 mg tablet and 0.374"×0.7480" modified oval tooling for the 1154 mg tablet
Accela-cota model 24MK III (24" coating pan)

All the raw materials with exception of magnesium stearate were charged to the PP-1 granulator and premixed for 3 minutes at 300 rpm impeller speed, no chopper. A baseline loss on drying determination was performed and the ungranulated hypromellose formula was determined to be 3.4% water while the Polyox formulation was 2.9%. Water was sprayed at approximately 200 grams/minute while mixing at 300 rpm with a slow chopper speed. The hypromellose formulation used 43% water (778 g water sprayed) of the 1.8 kg batch size while the Polyox formulation sprayed 52% water (905 g water sprayed) with a 2 minute post spray mix. The granulation was transferred into the MP-1 fluid bed and dried with an inlet temperature of 75° C. until the loss on drying (LOD) was ≤3%; equal to or slightly lower than the baseline moisture of the un-granulated formulations. The dried granulation was passed through a #4 mesh hand screen. The large granules retained on the #4 mesh were segregated and discarded. The remaining granules were sized through the FitzMill at low speed, knives forward. The blend was then lubricated with the magnesium stearate for 3 minutes. The final blend was compressed into tablets using a Korsch rotary press. After dissolution results were obtained, the core tablets were coated with a non-functional, Opadry II, white to a weight gain of approximately 4.5% w/w.

Outline of Dissolution Conditions were as follows:
900 mL dissolution medium: 50 mM Phosphate, pH 6.8
100 RPM Baskets
37° C.
Time points: 2, 4, 6, 8, 12, 16 or 24 hours The blending and granulation of the hypromellose based formulation proceeded smoothly. The hypromellose formulation processed well, producing a final blend with excellent flow that compressed well on the tablet press. The yield was excellent (96%) for a small scale batch size.

The Poly Ethylene Oxide (Polyox) based formulation did not granulate as easily. The Polyox formulation was over-granulated. The over-granulation can be alleviated in the future by spraying less granulation water at a slower rate. An appreciable amount of the granulation was lost when the partially dried granulation was screened through a 4 mesh sieved to remove large over-granulated agglomerates that resisted drying in the fluid bed. As a result, the batch yield was poor at 83%. The portion of the batch that was retained produced an excellent final blend, however. It flowed and compressed well on the tablet process and produced good quality tablets. Polyox is known for being difficult to granulate so this is not entirely unexpected. However, with the proper granulation parameters an excellent granulation can be attained.

Physical data for sialic acid 325 mg final blends, sialic acid 325 mg tablets, and sialic acid 500 mg tablets are shown in Tables 9, 10 and 11, respectively. Analytical results for sialic acid 325 and 500 mg tablets (uncoated) are shown in Table 12.

TABLE 9

Physical data for Sialic Acid, 325 mg Final Blends:

|  | (ProCR Hypomellose) | (ProCR Polyox) |
|---|---|---|
| Sieve # (% Retain) Mesh size (um) |  |  |
| 14 (1400) | 0.10 | 1.32 |
| 30 (600) | 42.89 | 45.4 |
| 40 (425) | 12.28 | 14.39 |
| 140 (106) | 33.98 | 29.89 |
| 200 (75) | 5.42 | 3.24 |
| 325 (45) | 4.61 | 4.86 |
| Pan (<45) | 0.72 | 0.91 |
| Blend Bulk Density (g/mL) | 0.54.9 | 0.54.5 |
| Tap Density (g/mL) | 0.646 | 0.619 |
| % Compressibility | 15 | 12 |
| Flowdex | 10 | 6 |

TABLE 10

Physical Data of Sialic Acid 325 mg Tablets at Various Hardnesses

| Test | Formulation A | Formulation B Hypromellose | Formulation C | Formulation D | Formulation E Polyox | Formulation F |
|---|---|---|---|---|---|---|
| Tablet Hardness Level | Low | Medium | High/ max | Low | Medium | High/ max |
| Ave. Weight (mg) | 759.5 | 754 | 754 | 739 | 745 | 750 |
| Ave. Thickness (in) | 0.279 | 0.270 | 0.259 | 0.260 | 0.247 | 0.253 |
| Ave. Hardness (kp) | 6.5 | 10.0 | 14.4 | 9.5 | 17.9 | 15.7 |
| Ave. Friability (%) | Failed | 0.2 | 0.1 | 0.1 | 0.0 | 0.2 |

Note:
Average of 10 tablets

TABLE 11

Physical Data of Sialic Acid 500 mg Final Blends and Tablets

| Test | Formulation G | Formulation H Hypromellose | Formulation I | Formulation J | Formulation K Polyox | Formulation L |
|---|---|---|---|---|---|---|
| Bulk Density (g/mL) |  | 0.55 |  |  | 0.54 |  |
| Tablet Hardness Level | Low | Medium* | High/ max | Low | Medium | High/ max |
| Ave. Weight (mg) | 1170 | ND | 1152 | 1158 | 1154 | 1160 |
| Ave. Thickness (in) | 0.324 | ND | 0.315 | 0.310 | 0.307 | 0.297 |
| Ave. Hardness (kp) | 11.3 | ND | 13.2 | 12.9 | 14.0 | 20.2 |
| Ave. Friability (%) | 0.2 | ND | 0.0 | 0.1 | 0.0 | 0.0 |

Note: Average of 10 tablets
*ND: not determined

TABLE 12

Analytical Results or Sialic Acid 325 mg and 500 mg SR Tablets (Uncoated)

| Test | Formulation C Hypromellose | Formulation F Polyox | Formulation I Hypromellose | Formulation K Polyox |
|---|---|---|---|---|
| Tablet Strength (mg) | 325 | 325 | 500 | 500 |
| Assay (% LC) | 96.3 | 97.8 | | |
| Impurities (%) | Total: 0.2 | Total: 0.2 | | |
| Dissolution (Average n = 3) % Release | | | | |
| 2 hr | 34 | 34 | 29 | 29 |
| 4 hr | 53 | 55 | 46 | 47 |
| 6 hr | 67 | 72 | 59 | 62 |
| 8 hr | 78 | 85 | 69 | 74 |
| 12 hr | 91 | 96 | 84 | 89 |
| 24 hr | 100 | 99 | 101 | 100 |

The dissolution results (FIG. 5) showed a first order sustained release profile over a 12 hour period for both dose strengths and for both ProCR hypromellose and ProCR Polyox. Additionally, these results indicate that the dose proportional approach was successful in providing dose flexibility using a common blend at 750 and 1154 tablet final weights.

Example 8

Coating for Sialic Acid 325 and 500 mg SR Tablets ProCR Hypromellose and ProCR Polyox Method of Manufacture Eight kilograms of core tablets (approximately 1.5 kg of active tablets combined with 6.5 kg of "sham" placebos to provided volume) were charged into an Accela-Cota coating equipment equipped with a 24" coating pan and two spray guns. The non-functional film coat was Opadry-II White (Colorcon Corporation formula Y-22-7719) at a 20% solids concentration. The purpose of the film coat was to improve aesthetics and in the future facilitate patient compliance for swallowing of the tablet. The target end-point was 3-5% weight gain.

The coating process parameters were as follows:
Pan speed: Target 12-16 rpm
Inlet temperature: 70-85° C.
Outlet temperature: 39-42° C.
Bed temperature: 33-45° C.
Atomization pressure: 40 psi
Spray Rate: 50-60 g/min
Airflow: approximately 200 cfm
Gun to bed distance: 5"

The tablets coated well with no difficulties. Approximately 4% weight gain of coating was sufficient to provide good coverage of the tablet cores.

Prototype Stability

Figure 6:
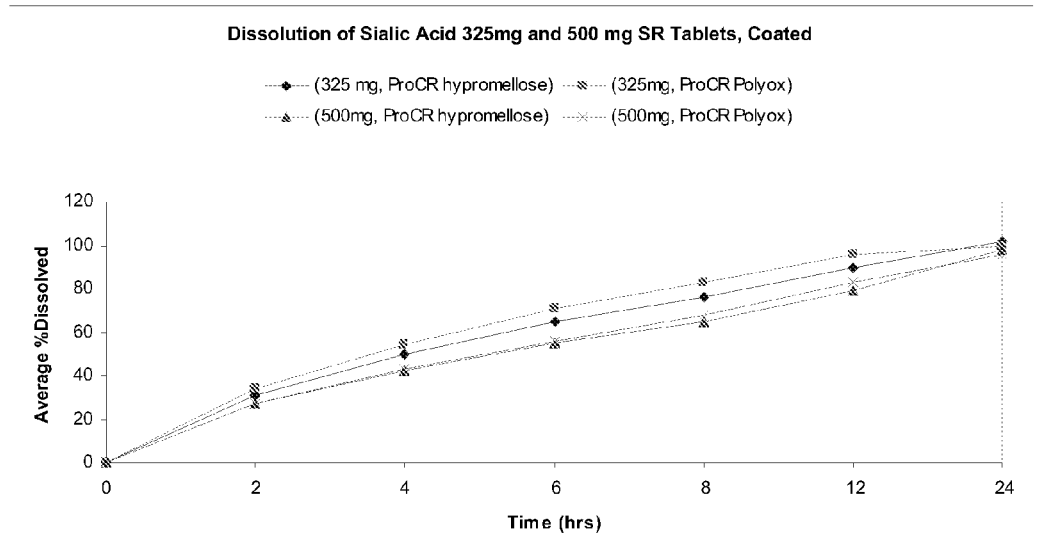
FIG. 6 shows the dissolution profile of sialic acid 325 and 500 mg sustained release (SR) coated tablets.

The white film coated tablets of Sialic Acid prepared using ProCR hypromellose and ProCR Polyox at 325 mg and 500 mg dose strengths were packaged in thirty (30) units per bottle, one MiniPax desiccant, no coil and induction sealed using a Lepak Jr™ induction cap sealing system. Table 13 lists the packaging components used. All the acceptable tablets were packaged and placed on a 12 month prototype stability program under ICH conditions testing the stability at both 25° C. and 60% relative humidity (RH) and 40° C. and 75% RH at 0, 1, 3, 6, and 12 months. The tablets have been tested and monitored with respect to appearance, dissolution, moisture, assay and related substances, and initial stability results are shown in Table 14. The dissolution profile for the coated 325 mg and 500 mg tablets is shown in FIG. 6.

TABLE 13

List of Packaging Components

| Component | Material Description | AAI RM # |
|---|---|---|
| Bottle | 100 cc Round White HDPE (38/400) | PC-3714 |
| Closure | 38 mm CRC w Foil Seal MI Liner | PC-3982 |
| Desiccant | MiniPax w 1.00 g Silica Gel-Packet | PC-2637 |

TABLE 14

Analytical Results of Sialic Acid 325 mg and 500 mg SR Tablets (Coated), Initial Stability

| Test | Formulation C Hypromellose | Formulation F Polyox | Formulation I Hypromellose | Formulation K Polyox |
|---|---|---|---|---|
| Tablet Strength (mg) | 325 | 325 | 500 | 500 |
| % Moisture by Karl Fischer | 1.0 | 3.3 | 2.0 | 3.7 |
| Content Uniformity (Ave, n = 10) | 100.0 | 95.6 | 99.8 | 98.6 |
| % RSD | 1.5 | 2.5 | 1.5 | 2.6 |
| AV | 3.5 | 9.2 | 3.6 | 6.3 |

TABLE 14-continued

Analytical Results of Sialic Acid 325 mg and 500 mg SR Tablets (Coated), Initial Stability

| Test | Formulation C Hypromellose | Formulation F Polyox | Formulation I Hypromellose | Formulation K Polyox |
|---|---|---|---|---|
| Assay (% LC) | 100.6 | 97.8 | 98.8 | 96.9 |
| Impurities (%) | Total: <0.10 | Total: <0.10 | Total: <0.10 | Total: <0.10 |
| Dissolution (Ave. % Release, n = 6)) | | | | |
| 2 hr | 31 | 34 | 27 | 27 |
| 4 hr | 50 | 54 | 42 | 43 |
| 6 hr | 65 | 70 | 55 | 56 |
| 8 hr | 75 | 83 | 65 | 68 |
| 12 hr | 90 | 96 | 79 | 83 |
| 24 hr | 102 | 100 | 98 | 96 |

The formulation development activities successfully identified two distinct sustained release prototypes for Sialic Acid in 325 and 500 mg dose strengths. The in-vitro dissolution release profile exhibited a first order release over 12 hours in aqueous medium and pH of 6.8. The sustained release ProCR platform was employed. This unique combination of inert polymers provides a robust formulation that is pH independent and lends itself to granulation processes without affecting the dissolution release profile. This was the case for Sialic Acid 325 and 500 mg dose strength SR tablets where a wet granulation process was found necessary to achieve densification and good tablet compressibility.

With regard to chemical stability Sialic Acid 325 and 500 mg ProCR hypromellose and ProCR Polyox SR tablets showed acceptable assay, dissolution and content uniformity and easily passed USP testing criteria. These prototypes are monitored through a 12 month ICH stability study.

Figure 5:
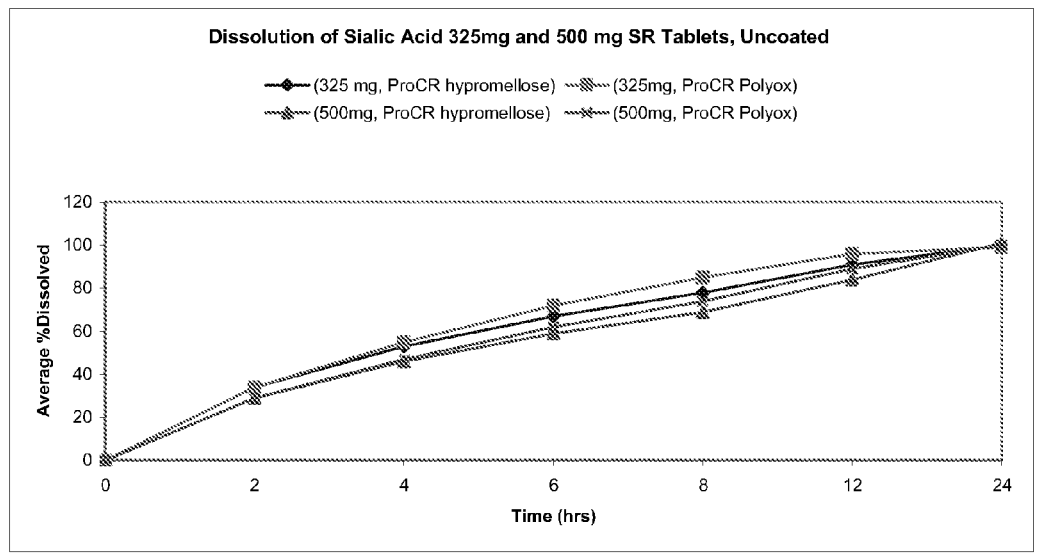
FIG. 5 shows the dissolution profile of sialic acid 325 and 500 mg sustained release (SR) uncoated tablets.

As shown in FIGS. 5 and 6, the dissolution profiles of Sialic Acid ProCR hypromellose and ProCR Polyox uncoated and coated tablets are consistent. There is no significant change in the sustained release profile over the 12 hour release with the application of Opdary® II White film coat. The analytical results for assay and related substances are acceptable which indicates that the wet granulation, drying and coating processes have no impact on the chemical integrity of the drug.

Example 9

Preparation of ManNAc 325 mg Development Prototypes

Figure 7:
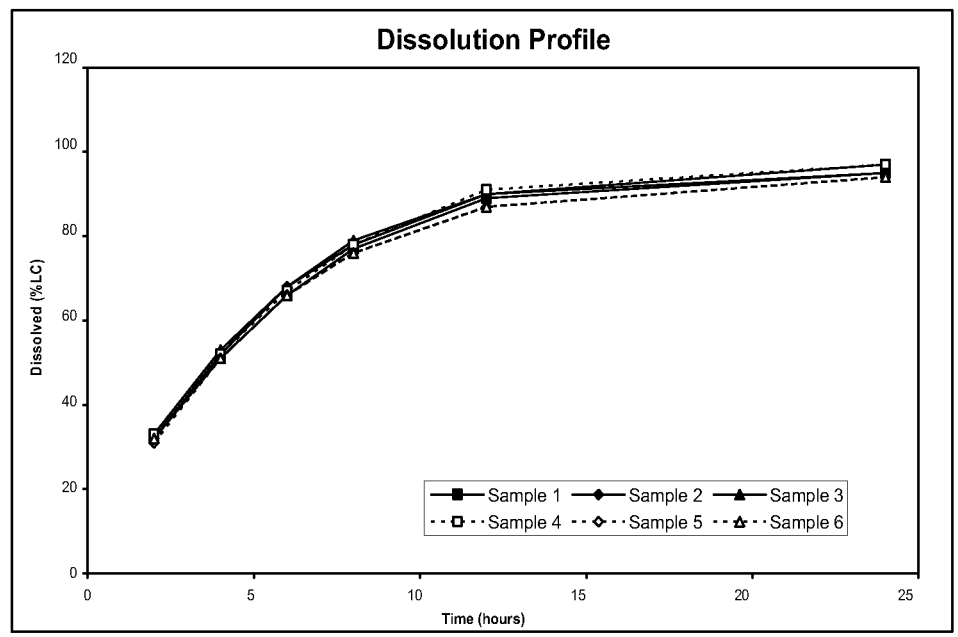
FIG. 7 shows the dissolution profile of ManNAc 325 mg tablets.
Figure 8A:
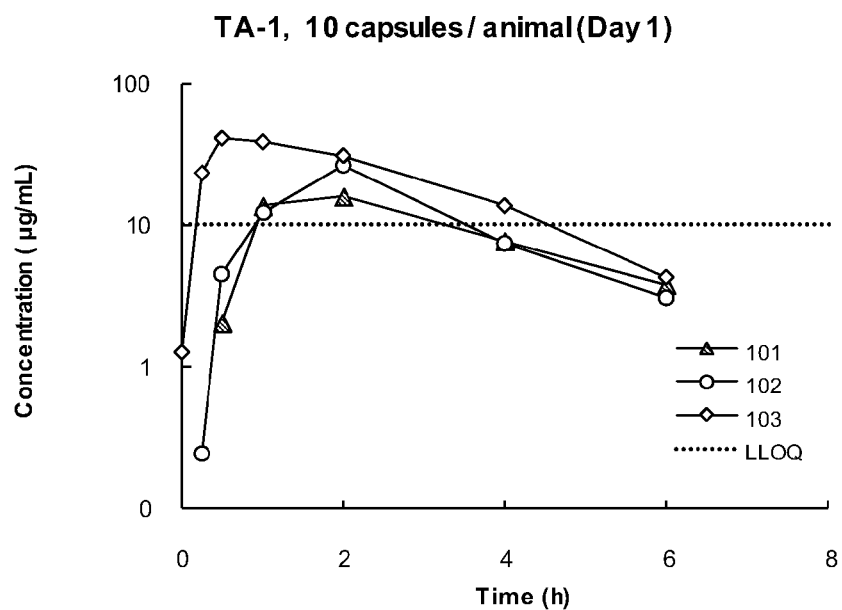
FIG. 8 shows the individual concentrations of sialic acid versus time in beagle dog serum following IV or oral administration. (A and B) concentration after administration of TA-1 capsules; (C) concentration after administration of TA-2 tablets; (D) concentration after administration of TA-3 tablet; (E) concentration after administration of TA-4 tablets; (F) concentration after administration of TA-5 tablets; (G and H) concentration after intravenous administration of TA-6.
Figure 8B:
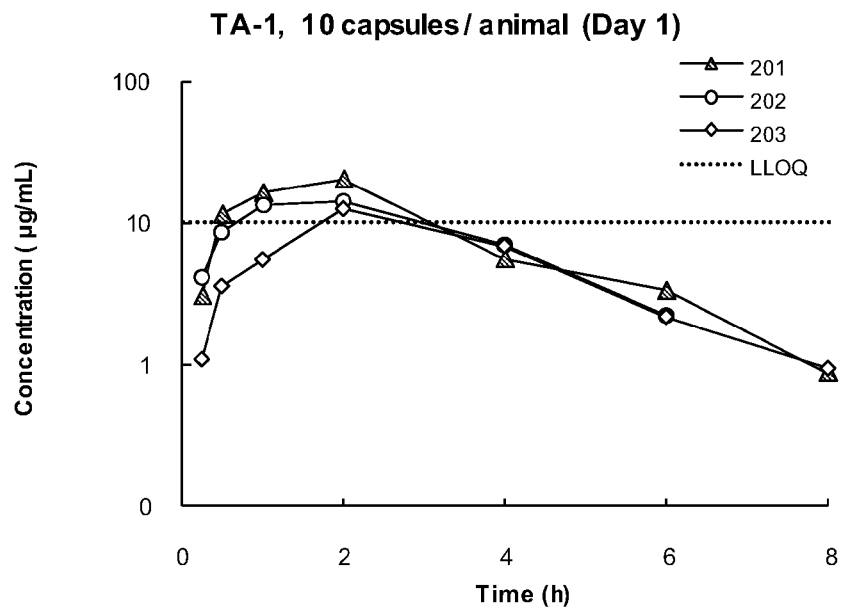
Figure 8C:
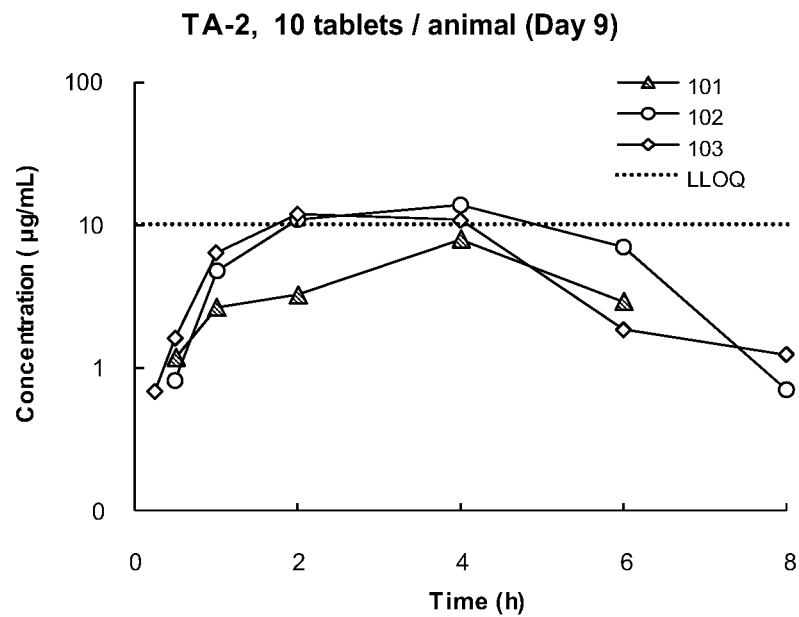
Figure 8D:
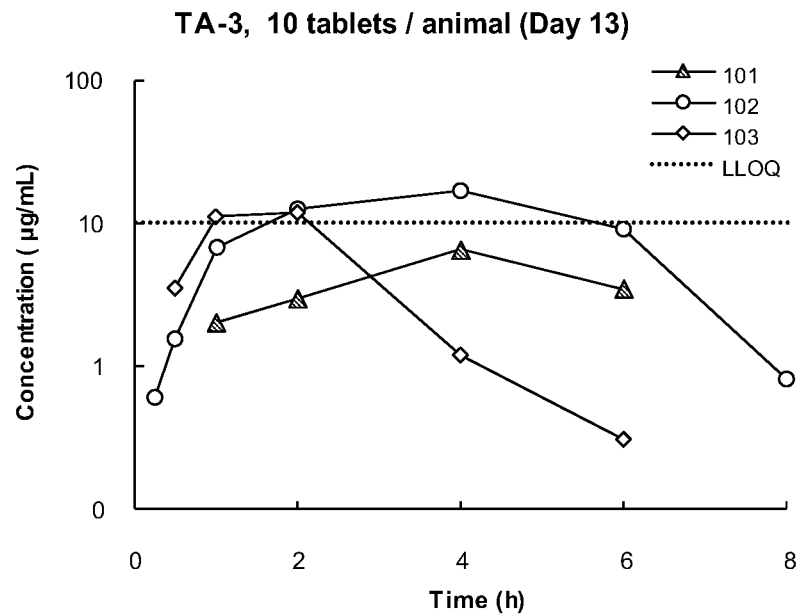
Figure 8E:
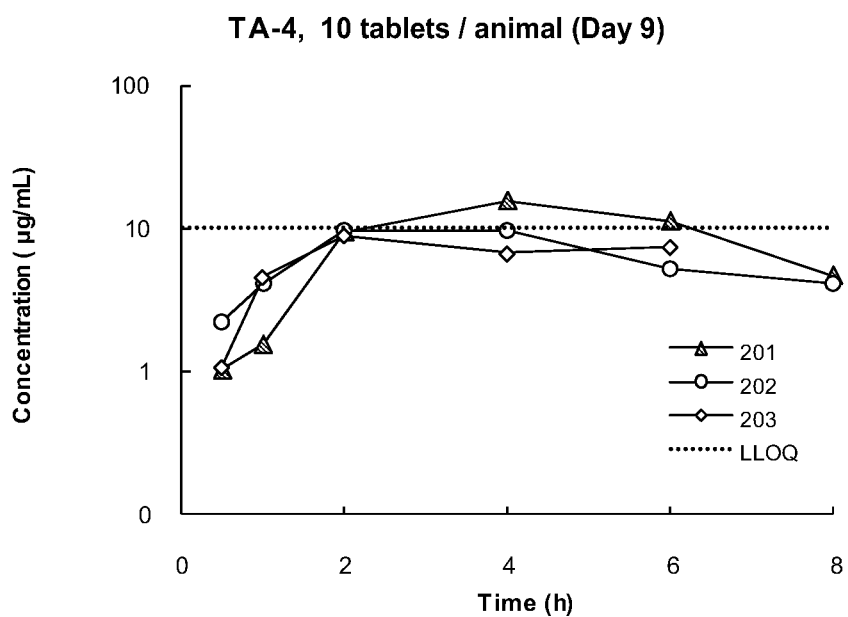
Figure 8F:
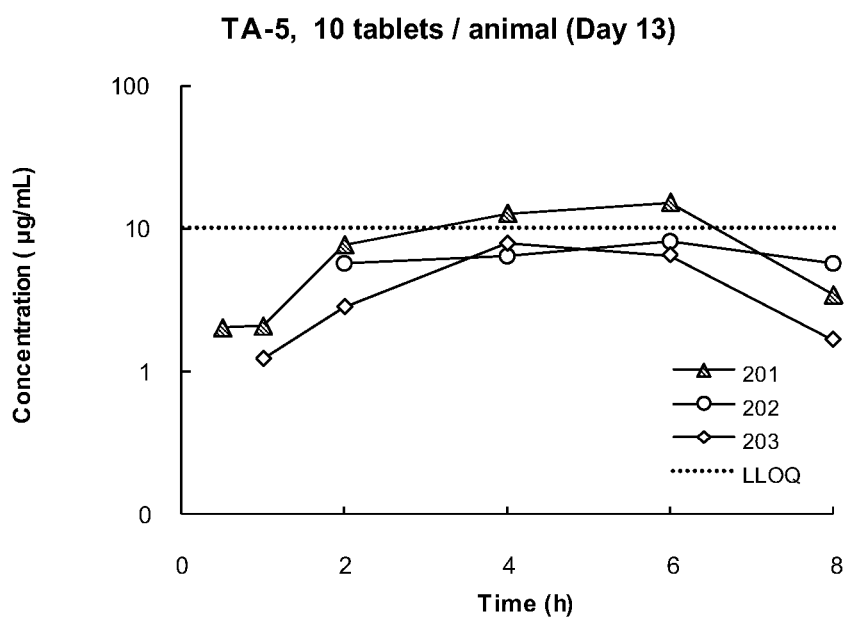
Figure 8G:
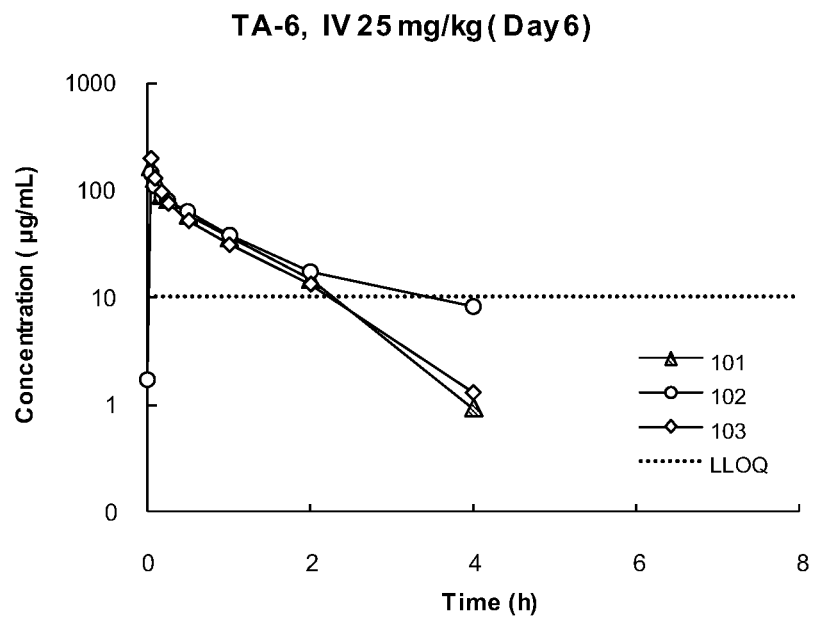
Figure 8H:
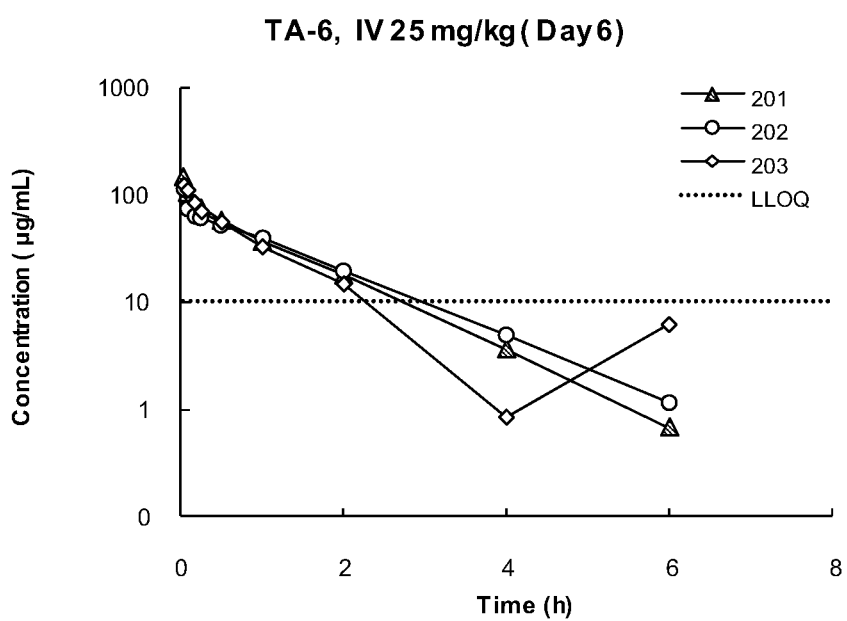

The ManNAc title formulation was prepared according to the method detailed above for Sialic Acid. The dissolution profile of ManNAc 325 mg Tablets is shown in FIG. 7.
Core Tablet Results

| Assay | |
|---|---|
| % LC = | 93.5% |

| Impurity | % RS |
|---|---|
| Sialic Acid | <0.10% |
| Sodium Pyruvate | <0.10% |
| N-Acetyl-D-Glucosamine | 0.4% |

-continued

| Impurity | % RS |
|---|---|
| Acetic Acid | <0.10% |
| Total | 0.4% |

| KF | |
|---|---|
| Prep | % water |
| 1 | 3.5 |
| 2 | 3.3 |
| Mean (2) | 3.4 |

| Content Uniformity | |
|---|---|
| Unit | % LC |
| 1 | 93.7 |
| 2 | 94.6 |
| 3 | 92.8 |
| 4 | 92.8 |
| 5 | 94.6 |
| 6 | 92.9 |
| 7 | 96.0 |
| 8 | 95.4 |
| 9 | 92.5 |
| 10 | 91.5 |
| Mean (10) | 93.7 |
| % RSD | 1.5 |
| SD | 1.42735186 |
| AV | 8.2 |

Example 10

Pharmacokinetics of Sialic Acid Formulations Following a Single Oral or Intravenous Dose in Male Dogs The objective of this study was to evaluate the pharmacokinetics of sialic acid following single oral or intravenous dose in male dogs.

A total of six male beagle dogs (*Canis familiaris*), originally from Beijing Marshall Biotechnology Co., Ltd., were obtained from the PCS-SHG colony and subjected to a general physical examination to ensure normal health status before study initiation. All animals were considered suitable for use and each animal was uniquely identified by a permanent skin tattoo number and/or letter on the ventral aspect of one pinna. An acclimation period of five days was allowed between animal transfer and the start of treatment in order to accustom the animals to the laboratory environment.

Before dosing initiation, all animals were weighed and assigned to treatment groups. At the start of treatment, animals were 7-16 months of age and ranged in weight as 6.4 to 9.4 kg. Animals were housed individually in stainless steel cages equipped with a mesh-type floor and an automatic watering valve. A standard certified pelleted commercial dog food (approximately 400 g of Certified Canine Diet 5C07, PMI Nutrition International, Inc.) was provided to each animal once daily, except during designated procedures. Maximum allowable concentrations of contaminants in the diet (e.g., heavy metals, aflatoxin, organophosphates, chlorinated hydrocarbons, PCBs) were controlled and routinely analyzed by the manufacturers. It was considered that there were no known contaminants in the food that could have interfered with the objectives of the study. Municipal tap water, which was softened, purified by reverse osmosis and exposed to ultraviolet light, was freely available except during designated procedures. It was considered that there were no known contaminants in the water that could have interfered with the objectives of the study. Each Animal was provided with a floor toy, except during designated activities.

The study design was as shown in Table 15:

TABLE 15

Experimental Design

| Group No. | Study Day | Test Article | Treatment[a] | Dose Level[#] (mg/kg) | Number of Tablets per animal | Dose Volume (mL/kg) | Dose Concentration (mg/mL) | Animal Number |
|---|---|---|---|---|---|---|---|---|
| 1 | 1 | TA-1 (capsule) | PO | — | 10 | — | — | 3 |
|  | 6 | TA-6 | IV | 25 | — | 0.5 | 50 |  |
|  | 9 | TA-2 (tablet) | PO | — | 10 | — | — |  |
|  | 13 | TA-3 (tablet) | PO | — | 10 | — | — |  |
| 2 | 1 | TA-1 (capsule) | PO | — | 10 | — | — | 3 |
|  | 6 | TA-6 | IV | 25 | — | 0.5 | 50 |  |
|  | 9 | TA-4 (tablet) | PO | — | 10 | — | — |  |
|  | 13 | TA-5 (tablet) | PO | — | 10 | — | — |  |

— = not applicable.
[#]Dose level was expressed as free form.
[a]Animals were fasted overnight for approximately 16 hours prior to each dose and were fed immediately after the 6 hr timepoint.

The first day of dosing was designated as Day 1. The subsequent dosing days were Days 6, 9 and 13. On Days 1, 9 and 13, all animals were orally administered prepared capsules or tablets. On Day 6, all animals received a single intravenous dose of TA-6 at 0.5 mL/kg. Each actual volume of TA-6 administered was based on the most recent practical body weight of each animal. The test articles 1 through 6 are specified in Table 16.

TABLE 16

Specification of Test Articles

| Test Article | Identification | Compositon/ Concentration | Dose Level | Animal Number |
|---|---|---|---|---|
| TA-1 | API in Capsule Form | 325 mg SA per capsule | 3250 mg SA per animal | 101-103, 201-203 |
| TA-2 | Sialic Acid Delayed Release Tablet Formulation I | 325 mg SA/425 mg excipient (hypromellose) per tablet | 3250 mg SA per animal | 101-103 |

TABLE 16-continued

Specification of Test Articles

| Test Article | Identification | Compositon/Concentration | Dose Level | Animal Number |
|---|---|---|---|---|
| TA-3 | Sialic Acid Delayed Release Tablet Formulation II | 325 mg SA/425 mg excipient (polyethylene oxide) per tablet | 3250 mg SA per animal | 101-103 |
| TA-4 | Sialic Acid Delayed Release Tablet Formulation III | 500 mg SA/650 mg excipient (hypromellose) per tablet | 5000 mg SA per animal | 201-203 |
| TA-5 | Sialic Acid Delayed Release Tablet Formulation IV | 500 mg SA/650 mg excipient (polyethylene oxide) per tablet | 5000 mg SA per animal | 201-203 |
| TA-6 | Sialic Acid IV Formulation | 50 mg/mL | 25 mg/kg SA | 101-103, 201-203 |

Individual body weights were measured once during the predose period and prior to each dose on dosing days. There were no treatment-related clinical signs observed during the study period and no treatment related changes in body weight or body weight gains noted for any animal during the study period.

Blood samples were collected into serum separate tubes from all animals on Days 1, 6, 9, 13 for processing to serum at the following time points: predose, 2 minutes (i.v. only), 5 minutes (i.v. only), 10 minutes (i.v. only), 15 minutes, 30 minutes, 1, 2, 4, 6, 8 and 24 hours postdose. Urine samples were collected into jars on wet ice or ice packs from all animals on Days 1, 6, 9, 13 at the following time intervals: predose (overnight for approximate 15 hours), 0 to 4, 4 to 8, 8 to 12 hours postdose. Samples were collected according to Table 17 and Table 18:

Drug concentrations in serum and urine were determined by LC MS/MS using a validated analytical procedure (Validation of a Method for the Determination of Free Soluble Sialic Acid in Dog Serum and Urine by Liquid Chromatography-Tandem Mass Spectrometry (LC-MS/MS)-PN 102653; Long-term Matrix Stability Assessment of Free Soluble Sialic Acid in Dog Serum and Urine by Liquid Chromatography-Tandem Mass Spectrometry (LC-MS/MS)-PN 102654. The method had a linear range from 10~1000 μg/mL and the lower limit of quantitation was 10 μg/mL.

Data collection was performed using Analyst® from AB Sciex. Statistical analyses including regression analysis and descriptive statistics including arithmetic means and standard deviations, accuracy and precision were performed

TABLE 17

PK Sample Collection Schedule

| Group No. | Sample Collection Time Points (Time Post Dose) on Days 1, 6, 9 and 13 | | | | | | | | | | | |
|---|---|---|---|---|---|---|---|---|---|---|---|---|
| | 0 min[a] | 2 min | 5 min | 10 min | 15 min | 30 min | 1 hr | 2 hr | 4 hr | 6 hr | 8 hr | 24 hr |
| 1 | X | X (IV only) | X (IV only) | X (IV only) | X | X | X | X | X | X | X | X |
| 2 | X | X (IV only) | X (IV only) | X (IV only) | X | X | X | X | X | X | X | X |

X = sample collected
[a]Samples were collected before dosing.

TABLE 18

Urine Sample Collection Schedule

| Group No. | Sample Collection Time Points (Time Post Dose) on Days 1, 6, 9 and 13 | | | |
|---|---|---|---|---|
| | Overnight[a] | 0-4 hr | 4-8 hr | 8-12 hr |
| 1 | X | X | X | X |
| 2 | X | X | X | X |

X = sample collected
[a]Blank urine were collected overnight (approximate 15 hours) before each dose.

Blood samples were placed at room temperature for at least 30 minutes but no more than 1 hour to clot prior to refrigerated centrifugation (approximately 4° C.) at approximately 2700 rpm for 10 minutes. The serum separated from each sample was transferred into polypropylene tubes and placed on dry ice until transferred to a freezer (set to maintain −80° C.). Urine samples were stored in a freezer (set to maintain −80° C.) until analyzed.

using Watson™ Laboratory Information Management System (LIMS) and Microsoft Excel.

Pharmacokinetic parameters were estimated using WinNonlin® pharmacokinetic software (Version 5.2.1, Pharsight Corp., Mountain View, Calif., USA). A non-compartmental approach consistent with the intravenous or oral route of administration was used for parameter estimation. All parameters were generated from individual sialic acid concentrations in serum. Parameters were estimated using nominal sampling times relative to the start of each dose administration. Mean concentrations were derived from 3 animals/group/time point for intravenous dosing occasion only. The actual timepoints were within the range of protocol specified. Serum concentration values obtained at the predose time point were used as the concentration at time zero for oral doses. The actual dose levels of test articles 1 through 5 were calculated using the total amount of SA given to each animal based on their most practical body weight.

The area under the sialic acid individual serum concentration versus time curve (AUC) was calculated using the linear trapezoidal method with linear interpolation. The terminal elimination phase of each individual concentration versus time curve was identified using at least the final three observed concentration values. The slope of the terminal elimination phase was determined using log linear regression on the unweighted concentration data. The terminal elimination phase related parameters were not reported if the coefficient of determination was less than 0.800, or the extrapolation of the AUC to infinity represented more than 20% of the total area, or the terminal elimination phase could not be identified. The parameters described in Table 19 were observed or calculated.

All data from serum including concentrations below LLOQ (except for those below zero) were applied to pharmacokinetic analysis.

TABLE 19

Estimated Parameters from Serum Concentrations of Sialic Acid

| Parameters | Description of parameter |
| --- | --- |
| Cmax | The maximum observed arithmetic individual concentration of sialic acid after dosing. |
| Tmax | The time after dosing when the maximum observed arithmetic individual concentration of sialic acid was observed. |
| AUC (0-t) | The area under the sialic acid arithmetic individual concentration versus time curve from time zero to the time after dosing when the last quantifiable concentration of the drug was observed. |
| MRT (0-t) | The mean residence time of sialic acid estimated from time zero to the time after dosing at which the last quantifiable concentration of the drug was observed estimated or imputed by the linear or linear/log trapezoidal method. |
| T½ | The apparent terminal elimination half life. |
| AUC (0-inf) | The area under the arithmetic individual concentration versus time curve from time zero to infinity. |
| MRT (0-inf) | The mean residence time estimated from time zero to infinity. |
| CL (IV only) | Clearance: the apparent volume of serum cleared of sialic acid per unit time following intravenous dosing. Clearance was calculated for intravenous dose only. |
| Vd (IV only) | The apparent volume of distribution of sialic acid, determined from the terminal elimination phase following intravenous dosing. Volume of distribution was calculated for intravenous dose only. |
| Fs | Absolute bioavailability based on sialic acid levels in the serum following IV and oral administration. |

Urinary concentrations of sialic acid were subjected to calculation using Microsoft® Excel, 2007. All data from urine including concentrations below LLOQ (except for those below zero) were applied.

The data of predose urine samples were applied to calculate the total increase in urinary excretion of sialic acid at 12 hours postdose. The urinary excretion of sialic acid, as a percent of dose administered was estimated for each dosing occasion. Based on the assumption that the amount of drug excreted in urine after oral administration was a reflection of the dose absorbed, the bioavailability of sialic acid was determined based on the percent excretion value following IV and oral administration.

The parameters described in Table 20 were observed or calculated.

TABLE 20

Estimated Parameters from Urine Concentrations of Sialic Acid

| Parameters | Description of parameter |
| --- | --- |
| Dose | The amount of SA dosed per animal contained in each test article. |
| Mass Excreted (0-12 hr) | The total mass of urinary excretion of sialic acid at 12 hours postdose. |
| Mass Excreted (0-12 hr)-Corrected | The corrected value calculated by subtracting out the background masses based on predose data, representing the increase in urinary excretion of sialic acid at 12 hours postdose. If corrected value was less than zero, the value was set to zero. |
| Percent Excretion (0-12 hr) | The corrected mass excreted of sialic acid as a percent of dose administered. |
| Fu | Bioavailability based on the sialic acid levels in the urine following IV and oral administration. |

There were no treatment-related clinical signs noted following either oral or intravenous administration of sialic acid over the study period. Skin red was noted for Animal Nos. 201 and 203 during the study, which was considered as incidental.

There were no treatment related changes in body weight or body weight gains noted for any animal during the study period. Any differences in body weight or body weight gain were likely related to expected biological variation.

Individual concentrations of sialic acid versus time in Beagle dog serum following IV or oral administration are shown in FIGS. 8A-8H.

TA-1

The background sialic acid levels were below zero for predose samples of five of the six animals, except for Animal No. 103, of which was slightly above zero but below 20% of the LLOQ.

Following oral administration of TA-1 in prepared capsules at 3250 mg of SA per animal, peak concentrations were observed ranging from 12.6 to 40.8 µg/mL. $T_{max}$ was observed at 2 hours postdose with the exception of Animal No. 103 (0.5 hours). The concentrations of sialic acid decreased to levels below zero at 24 hours postdose for all six animals. The concentration of Animal No. 201 at 24 hour postdose (22.0989 µg/mL) was considered as aberrant and excluded from analysis, as it was a >LLOQ value but following three <LLOQ samples which followed three quantifiable concentrations in the sampling sequence.

Towards the end of the sampling period, a decrease in sialic acid concentrations was apparent, but the terminal elimination half-life could only be calculated for Animal Nos. 103, 201 and 203, ranging from 1.39 to 1.49 hours.

The bioavailability of TA-1 was estimated to be ranging from 2.73% to 6.76%, based on the individual AUC(0-t) value following IV and oral administration.

All the predose urine samples had a measurable concentration of sialic acid while the data varied for each individual, ranging from 8.16 to 25.1 µg/mL. The maximum excretion of sialic acid was observed for samples collected 4-8 hours postdose, except for Animal No. 202 (0-4 hours postdose). The total mass of sialic acid excreted in the urine was equivalent to 0.43-3.56% of the doses of SA contained in TA-1.

The bioavailability of TA-1 was estimated to be ranging from 1.29% to 39.1% based on the individual urinary percent excretion value following IV and oral administration.

TA-2

The background sialic acid levels were below zero for predose samples of Animal Nos. 102 and 103 except for Animal No. 101, of which was slightly above zero but below 20% of the LLOQ.

Following oral administration of TA-2 in prepared tablets at 3250 mg of SA per animal, Tmax was observed from 2.00 to 4.00 hours postdose with the peak concentrations ranging from 7.98 to 13.7 µg/mL. The concentrations of sialic acid generally decreased after $T_{max}$ to levels below zero at 24 hours postdose, for all dosed animals. The elimination half life of sialic acid was estimated to be 1.28 hour in Animal No. 103. For Animal Nos. 101 and 102, the half-life could not be estimated as the measurable data were not enough to identify the termination elimination phase.

The oral bioavailability of TA-2 was estimated to be ranging from 1.64% to 3.25%, based on the individual AUC(0-t) value following IV and oral administration.

All the predose urine samples had a measurable concentration of sialic acid ranging from 13.5 to 34.8 µg/mL. The maximum excretion of sialic acid was observed for samples collected 4-8 hours postdose for all animals. The total increase of sialic acid excreted in the urine postdose was equivalent to 1.08-3.20% of the doses of SA contained in TA-2.

The bioavailability of TA-2 was estimated to be 2.53% and 3.73% for Animal Nos. 102 and 103, respectively, based on the individual urinary percent excretion value following IV and oral administration. The bioavailability is 97.4% for Animal No. 101, which was markedly higher than the other two animals due to its low percent excretion value of IV doses.

TA-3

The background sialic acid levels were below zero for predose samples of all three animals.

Following oral administration of TA-3 in prepared tablets at 3250 mg of SA per animal, Tmax was observed from 2.00 to 4.00 hours postdose with the peak concentrations ranging from 6.52 to 17.0 µg/mL. The concentrations of sialic acid generally decreased after Tmax to levels below zero at 24 hours postdose for all three animals. However, the half-life could not be estimated for the three animals as the measurable data were not enough to identify the termination elimination phase or the extrapolation of the AUC to infinity represented more than 20% of the total area.

The oral bioavailability of TA-3 was estimated to be ranging from 1.46% to 4.14%, based on the individual AUC(0-t) value following IV and oral administration.

Concentrations of sialic acid of all the predose urine samples were noted to be slightly above LLOQ, ranging from 10.1 to 11.2 µg/mL. The maximum excretion of sialic acid was observed for samples collected 4-8 hours postdose for Animal Nos. 102 and 103, and 8-12 hours postdose for Animal No. 101, respectively. The total increase of sialic acid excreted in the urine postdose was equivalent to 0.94-2.99% of the doses of SA contained in TA-3.

The bioavailability of TA-3 was estimated to be 3.49% and 1.51% for Animal Nos. 102 and 103, respectively, based on the individual urinary percent excretion value following IV and oral administration. The bioavailability is 85.0% for Animal No. 101, which was markedly higher than the other two animals due to its low percent excretion value of IV doses.

TA-4

In animals treated with TA-4, no sialic acid was measurable beyond 30 minutes postdose.

Following oral administration of TA-4 in prepared tablets at 5000 mg of SA per animal, most of the concentrations of sialic acid were below LLOQ with the exception of one dog (Animal No. 201), where the concentrations were slightly above LLOQ at 4 and 6 hours postdose. Tmax was observed from 2.00 to 4.00 hours postdose with the peak concentrations ranging from 8.97 to 15.7 µg/mL. The concentrations of sialic acid generally decreased after Tmax to levels below zero at 24 hours postdose for all dosed animals. The half-life could not be estimated as the measurable data were not enough to identify the termination elimination phase.

The oral bioavailability of TA-4 was estimated to be ranging from 1.57% to 2.09%, based on the individual AUC(0-t) value following IV and oral administration.

All the predose urine samples had a measurable concentration of sialic acid ranging from 6.4 to 42.6 µg/mL. The maximum excretion of sialic acid was observed for samples collected 8-12 hours postdose for Animal Nos. 201 and 203, and 0-4 hours for Animal No. 202, respectively. The total increase of sialic acid excreted in the urine postdose was equivalent to 0.54-1.93% of the doses of SA contained in TA-4.

The bioavailability of TA-4 was estimated to be 1.42% and 2.55% for Animal Nos. 202 and 203 based on the individual urinary percent excretion value following IV and oral administration. The bioavailability of Animal No. 101 could not be estimated as the mass excreted of sialic acid postdose was set to be zero when corrected by predose data.

TA-5

The background sialic acid levels of all animals were below zero for both predose samples and 15 minutes postdose.

Following oral administration of TA-5 in prepared tablets at 5000 mg of SA per animal, most of the concentrations of sialic acid were below LLOQ with the exception of Animal No. 201, of which were slightly above LLOQ at 4 and 6 hours postdose. Tmax was observed from 4.00 to 6.00 hours postdose with the peak concentrations ranging from 7.79 to 15.3 µg/mL. The concentrations the sialic acid generally decreased to levels below zero at 24 hours postdose for all three animals. However, the half-life could not be estimated for the three animals as the measurable data were not enough to identify the termination elimination phase.

The oral bioavailability of TA-5 was estimated to be ranging from 1.47% to 1.96%, based on the individual AUC(0-t) value following IV and oral administration.

Concentrations of sialic acid of all the predose urine samples ranged from 2.27 to 23.6 µg/mL. The maximum excretion of sialic acid was observed for samples collected 4-8 hours postdose for Animal Nos. 202 and 203, and 0-4 hours postdose for Animal No. 201, respectively. The total increase of sialic acid excreted in the urine postdose was equivalent to 0.02-1.70% of the doses of SA contained in TA-5.

The oral bioavailability of TA-5 was estimated to be 0.52% and 2.24%, for Animal Nos. 202 and 203, respectively, based on individual urinary percent excretion value following IV and oral administration. The bioavailability of Animal No. 101 could not be estimated as the mass excreted of sialic acid postdose was set to be zero when corrected by predose data.

TA-6

The serum levels of sialic acid were below zero for predose samples of most animals except for one dog, Animal No. 102, of which was slightly above zero but below 20% of the LLOQ.

Following an intravenous dose of 25 mg/kg of TA-6, the concentrations of sialic acid decreased quickly to levels below LLOQ at the timepoint of 4 hours postdose, and then to levels below zero at the timepoint of 8 hours postdose, for all six animals. The concentrations generally declined in animals, except that Animal No. 203 exhibited much higher concentrations at 6 hours postdose when compared to the previous time point. Sialic acid was eliminated in dogs with the half lives ranging from 0.56 to 1.40 hours.

The concentrations of sialic acid in the urine varied between each animal. It was noted that the sialic acid levels in urine collected postdose were lower than predose for Animal No. 201, with two of the three concentrations of postdose samples detected as below zero.

The IV dose resulted in 72.4-87.7% of the administered dose being excreted in the urine of five of the six animals. One dog (Animal No. 101) demonstrated excretion of only 1.1% of the applied dose.

The individual urinary percent excretion of TA-6 was used to adjust the data of oral doses to account for the fraction of sialic acid absorbed (Fu, %). From the data reported herein, Animal No. 101 were observed to have much lower urinary excretion postdose after IV dose, which resulted in a markedly higher value of bioavailability estimated for its oral doses when compared with other animals in the same group.

In summary, after oral administration of TA-1 through TA-5, low sialic acid levels were detected in serum, most of which fell below the limit of quantitation. Peak concentrations ranging from 6.52 to 40.8 μg/mL were observed from 0.5 to 6 hours postdose. Sialic acid was eliminated with a half-life of 0.56 to 1.40 hours, calculated based on the serum concentration data from intravenous dose of TA-6. The bioavailability was estimated based on the individual AUC (0-t) value following IV and oral administration. The pharmacokinetic parameters estimated for sialic acid in serum are presented in Table 21 to Table 23.

TABLE 21

Pharmacokinetic parameters estimated for sialic acid in serum

| Test Article | Dose Level (mg/kg) | Animal Number | Cmax (μg/mL) | Tmax (h) | AUC(0-t) (μg * h/mL) | Fs (%) |
|---|---|---|---|---|---|---|
| TA-1 | 353-445 | 101-103 | 15.8-40.8 | 0.5-2 | 54.1-128 | 3.43-6.76 |
|  | 346-508 | 201-203 | 12.6-20.5 | 2 | 43.5-66.7 | 2.73-3.20 |
| TA-2 | 361-451 | 101-103 | 7.98-13.7 | 2-4 | 26.5-62.4 | 1.64-3.25 |
| TA-3 | 353-439 | 101-103 | 6.52-17.0 | 2-4 | 23.1-77.6 | 1.46-4.14 |
| TA-4 | 538-746 | 201-203 | 8.97-15.7 | 2-4 | 38.3-74.4 | 1.57-2.09 |
| TA-5 | 543-781 | 201-203 | 7.79-15.3 | 4-6 | 35.7-73.6 | 1.47-1.96 |
| TA-6 | 25 | 101-103 | — | — | 106-123 | — |
|  | 25 | 201-203 | — | — | 108-120 | — |

— = not applicable.

TABLE 22

Pharmacokinetic Parameters of Sialic Acid in Beagle Dog Serum Following Oral Administration

| Test Article | Dose Level (mg/kg) | Animal Number | Cmax (μg/mL) | Tmax (h) | AUC(0-t) (μg * h/mL) | MRT(0-t) (h) | T½ (h) | AUC(0-inf) (μg * h/mL) | MRT(0-inf) (h) | Fs (%) |
|---|---|---|---|---|---|---|---|---|---|---|
| TA-1 | 353 | 101 | 15.8 | 2.00 | 54.1 | 2.63 | a | a | a | 3.43 |
|  | 406 | 102 | 26.3 | 2.00 | 68.4 | 2.45 | a | a | a | 3.44 |
|  | 445 | 103 | 40.8 | 0.50 | 128 | 2.07 | 1.41 | 137 | 2.45 | 6.76 |
| TA-1 | 508 | 201 | 20.5 | 2.00 | 66.7 | 2.51 | 1.49 | 68.6 | 2.72 | 2.73 |
|  | 346 | 202 | 14.2 | 2.00 | 51.9 | 2.39 | a | a | a | 3.20 |
|  | 357 | 203 | 12.6 | 2.00 | 43.5 | 3.00 | 1.39 | 45.4 | 3.29 | 2.81 |
| TA-2 | 361 | 101 | 7.98 | 4.00 | 26.5 | 3.51 | a | a | a | 1.64 |
|  | 392 | 102 | 13.7 | 4.00 | 62.4 | 3.76 | a | a | a | 3.25 |
|  | 451 | 103 | 11.9 | 2.00 | 50.0 | 3.19 | 1.28 | 52.3 | 3.48 | 2.60 |
| TA-3 | 353 | 101 | 6.52 | 4.00 | 23.1 | 3.65 | a | a | a | 1.46 |
|  | 382 | 102 | 17.0 | 4.00 | 77.6 | 3.80 | a | a | a | 4.14 |
|  | 439 | 103 | 11.9 | 2.00 | 30.6 | 1.84 | a | a | a | 1.64 |
| TA-4 | 746 | 201 | 15.7 | 4.00 | 74.4 | 4.41 | a | a | a | 2.07 |
|  | 538 | 202 | 9.69 | 2.00 | 52.6 | 3.91 | b | b | b | 2.09 |
|  | 562 | 203 | 8.97 | 2.00 | 38.3 | 3.37 | a | a | a | 1.57 |
| TA-5 | 781 | 201 | 15.3 | 6.00 | 73.6 | 4.59 | a | a | a | 1.96 |
|  | 543 | 202 | 8.20 | 6.00 | 46.4 | 4.70 | a | a | a | 1.83 |
|  | 562 | 203 | 7.79 | 4.00 | 35.7 | 4.58 | a | a | a | 1.47 | a: parameter was not reportable due to the measurable data were not enough to identify the termination elimination phase.

b: parameter was not reportable due to the extrapolation of the AUC to infinity represented more than 20% of the total area.

TABLE 23

Pharmacokinetic parameters of sialic acid in beagle dog serum following IV administration

| Test Article | Dose Level (mg/kg) | Animal Number | AUC(0-t) (μg * h/mL) | MRT(0-t) (h) | T½ (h) | AUC(0-inf) (μg * h/mL) | MRT(0-inf) (h) | CL (mL/min/kg) | Vd (L/kg) |
|---|---|---|---|---|---|---|---|---|---|
| TA-6 | 25 | 101 | 112 | 0.82 | 0.56 | 113 | 0.84 | 3.70 | 0.18 |
|  | 25 | 102 | 123 | 1.06 | 1.40 | 139 | 1.65 | 3.00 | 0.36 |
|  | 25 | 103 | 106 | 0.79 | 0.66 | 108 | 0.84 | 3.87 | 0.22 |
| TA-6 | 25 | 201 | 120 | 1.08 | 0.86 | 121 | 1.13 | 3.44 | 0.26 |
|  | 25 | 202 | 117 | 1.27 | 0.99 | 119 | 1.35 | 3.51 | 0.30 |
|  | 25 | 203 | 108 | 1.18 | 0.58 | 113 | 1.43 | 3.67 | 0.18 |

All the predose urine samples had a measurable concentration of sialic acid and this was used to correct the total increase in urinary excretion of sialic acid at 12 hours postdose. In contrast to serum, most of the concentrations detected in urine samples exceeded the limit of quantitation. The urinary excretion of sialic acid, as a percent of dose administered was estimated for each dosing occasion. Based on the assumption that the amount of drug excreted in urine after oral administration was a reflection of the dose absorbed, the bioavailability of sialic acid was determined based on the percent excretion value following IV and oral administration. The urinary excretion parameters estimated for sialic acid are presented in Table 24 to Table 26

TABLE 24

Urinary excretion parameters estimated for sialic acid

| Test Article | Dose Level (mg/kg) | Animal Number | Percent Excretion (0-12 hr) (%) Range | Fu (%) Range |
|---|---|---|---|---|
| TA-1 | 353-445 | 101-103 | 0.43-3.56 | 2.47-39.1 |
|  | 346-508 | 201-203 | 0.93-2.57 | 1.29-2.17 |

TABLE 24-continued

Urinary excretion parameters estimated for sialic acid

| Test Article | Dose Level (mg/kg) | Animal Number | Percent Excretion (0-12 hr) (%) Range | Fu (%) Range |
|---|---|---|---|---|
| TA-2 | 361-451 | 101-103 | 1.08-3.20 | 2.53-97.4 |
| TA-3 | 353-439 | 101-103 | 0.94-2.99 | 1.51-85.0 |
| TA-4 | 538-746 | 201-203 | 0.54-1.93 | 1.42-2.55 |
| TA-5 | 543-781 | 201-203 | 0.02-1.70 | 0.52-2.24 |
| TA-6 | 25 | 101-103 | 1.11-87.7 | — |
|  | 25 | 201-203 | 0-75.7 | — |

— = not applicable.

TABLE 25

Urinary excretion of sialic acid in beagle dog following oral administration

| Test Article | Dose (mg/animal) | Dose Level (mg/kg) | Animal Number | Mass Excreted (μg) Predose | Mass Excreted (μg) 0-4 hr | Mass Excreted (μg) 4-8 hr | Mass Excreted (μg) 8-12 hr | Mass Excreted (0-12 hr) (μg) | Mass Excreted (0-12 hr) (μg) Corrected | Percent Excretion (0-12 hr) (%) | Fu (%) |
|---|---|---|---|---|---|---|---|---|---|---|---|
| TA-1 | 3250 | 353 | 101 | 4652.55 | 149.630 | 13342.9 | 4314.71 | 17807.2 | 14085.2 | 0.43 | 39.1 |
|  |  | 406 | 102 | 2448.73 | 549.029 | 65305.8 | 4816.71 | 70671.5 | 68712.5 | 2.11 | 2.47 |
|  |  | 445 | 103 | 4206.50 | 313.356 | 101372 | 17403.2 | 119089 | 115724 | 3.56 | 4.06 |
| TA-1 | 3250 | 508 | 201 | 2372.90 | 0 | 85288.8 | 0 | 85288.8 | 83390.5 | 2.57 | n/a |
|  |  | 346 | 202 | 1177.24 | 21908.6 | 319.025 | 8998.13 | 31225.8 | 30284.0 | 0.93 | 1.29 |
|  |  | 357 | 203 | 1966.81 | 17.3023 | 53674.5 | 1286.44 | 54978.2 | 53404.8 | 1.64 | 2.17 |
| TA-2 | 3250 | 361 | 101 | 4083.30 | 139.071 | 37257.4 | 942.062 | 38338.5 | 35071.9 | 1.08 | 97.4 |
|  |  | 392 | 102 | 4244.85 | 14977.6 | 76498.4 | 15826.0 | 107302 | 103906 | 3.20 | 3.73 |
|  |  | 451 | 103 | 4006.52 | 1003.46 | 73487.3 | 848.833 | 75339.6 | 72134.4 | 2.22 | 2.53 |
| TA-3 | 3250 | 353 | 101 | 5310.07 | 6980.87 | 482.029 | 27399.5 | 34862.4 | 30614.3 | 0.94 | 85.0 |
|  |  | 382 | 102 | 4269.49 | 33345.4 | 64010.5 | 3337.18 | 100693 | 97277.5 | 2.99 | 3.49 |
|  |  | 439 | 103 | 2936.63 | 1901.40 | 42627.6 | 788.657 | 45317.7 | 42968.3 | 1.32 | 1.51 |
| TA-4 | 5000 | 746 | 201 | 2767.70 | 526.991 | 368.095 | 28316.5 | 29211.6 | 26997.4 | 0.54 | n/a |
|  |  | 538 | 202 | 5621.96 | 29695.1 | 709.442 | 25589.5 | 55994.0 | 51496.5 | 1.03 | 1.42 |
|  |  | 562 | 203 | 4074.90 | 385.991 | 73.4542 | 99426.6 | 99886.0 | 96626.1 | 1.93 | 2.55 |
| TA-5 | 5000 | 781 | 201 | 1178.21 | 1269.32 | 372.873 | 63.4198 | 1705.61 | 763.046 | 0.02 | n/a |
|  |  | 543 | 202 | 966.212 | 303.204 | 19168.7 | 281.709 | 19753.6 | 18980.7 | 0.38 | 0.52 |
|  |  | 562 | 203 | 2479.44 | 443.881 | 63164.8 | 23357.0 | 86965.7 | 84982.2 | 1.70 | 2.24 | n/a = not applicable

TABLE 26

Urinary excretion of sialic acid in beagle dog following IV administration

| Test Article | Dose (mg/animal) | Dose Level (mg/kg) | Animal Number | Mass Excreted (µg) | | | | Mass Excreted (0-12 hr) (µg) | | Percent Excretion (0-12 hr) (%) |
|---|---|---|---|---|---|---|---|---|---|---|
| | | | | Predose | 0-4 hr | 4-8 hr | 8-12 hr | | Corrected | |
| TA-6 | 227.5 | 25 | 101 | 256.405 | 1941.56 | 509.021 | 274.902 | 2725.48 | 2520.36 | 1.11 |
| | 202.5 | 25 | 102 | 3508.71 | 161656 | 10622.6 | 4086.45 | 176365 | 173558 | 85.7 |
| | 182.5 | 25 | 103 | 6124.14 | 105.980 | 158924 | 5859.68 | 164890 | 159990 | 87.7 |
| TA-6 | 162.5 | 25 | 201 | 3085.53 | 267.937 | 0 | 0 | 267.937 | 0 | 0 |
| | 237.5 | 25 | 202 | 1977.36 | 165111 | 400.537 | 8095.96 | 173607 | 172026 | 72.4 |
| | 227.5 | 25 | 203 | 1487.66 | 119734 | 50377.7 | 3394.26 | 173506 | 172316 | 75.7 |

In conclusion, the pharmacokinetics of sialic acid in different formulations following a single oral or intravenous dose in the beagle dog were estimated, based on the serum and urine concentration data in this study.

Example 11

Relative Therapeutic Effect of Continuous vs. Once Daily Oral Exposure to Sialic Acid Replacement for 28 Days in HIBM Mice The study is designed to assess the benefit of continuous exposure and substrate replacement with sialic acid versus episodic exposure to sialic acid. The use of sialic acid to produce glycoproteins and glycolipids is a continuous biologic process and stores of sialic acid intermediates are believed to be small. In addition, oral boluses of sialic acid are likely to result in rapid urinary clearance. By comparing oral boluses with continuous exposure we can assess the relative benefit of providing continuous delivery of sialic acid, that might be achievable in humans with an extended release ER formulation. ALZET pumps will allow us to provide a continuous level of drug exposure to compare with oral bolus treatment. The effect of the therapy on biochemical normalization of sialylation and effects on muscle pathology and function are assessed to determine the impact of continuous versus bolus therapy.

Experimental Design

The experimental design will compare one group of mice treated with once per day bolus of sialic acid at 200 mg/kg, with two dose levels of sialic acid provided by continuous IP administration using Alzet minipumps. Female HIBM mice are used for this study with five mice per study group. The dose levels chosen for the minipump animals are 5 mg/kg which would be about equivalent to 200 mg/kg orally with a 2.5% rate of absorption, and 20 mg/kg, which would be about 10% rate of absorption. Due the limited number of animals, there are no control animals. A previous experiment in similarly aged mice would provide potential comparative control animals for this experiment. The design will capture baselines for easily accessible samples, including free sialic acid, creatine kinase in blood, polysialylated NCAM (PSA-NCAM) from blood, and total sialylated proteins in blood if possible. The animals are treated for 1 month, and sampled as intervals as shown. At the end of the month, the animals are taken down with blood for the same assays above, as well muscle tissues for NCAM westerns, frozen sections for surfaces sialylation, and samples for biochemical analysis of bound and free sialic acid. By comparing the degree of sialylation in the blood and in the tissues, it is determined if bolus or continuous exposure are superior. The total dose is checked by measuring free sialic acid in the blood and by measuring sialic acid in the urine.

Test Article 1: Bolus: Group 1
Oral formulation of sialic acid 4 mg/ml is administered at a dose of 200 mg/kg/day. The volume of injection is adjusted by individual body weight and dose concentration. Approximate dose volume per day is 250 uL.

Test Article 2: Pumps: Group 2
IP formulation of sialic acid 37.5 mg/ml is administered at a dose of 5 mg/kg/day. The volume of injection is 100 uL total per pump.

Test Article 3: Pumps: Group 3
IP formulation of sialic acid 150 mg/ml is administered at a dose of 20 mg/kg/day. The volume of injection is 100 uL total per pump.

Animal Care and Housing

Post Alzet pump placement each mouse is housed individually for accurate clinical observations and safety of the animal. Oral bolus group may be housed together in one cage. Each cage will receive water ad libitum. Animals are examined during the working day for morbidity and mortality. Body weights are recorded prior to the first dose administration and once weekly thereafter. Animals are fasted prior to pump placement and prior to blood collection and necropsy days. Animals are fed 4 hrs post dose but fasted for no longer than 24 hours.

Alzet Pumps: Preparation and Implantation

Alzet pump model 1004 with a flow rate of 0.11 uL/hr for 28 days is used and the manufacturer's recommendations regarding handling, priming and filling the Alzet pumps (WorldWideWeb: alzet.com/products/guide_to_use/filling.html) is followed Animals are anesthetized using isoflurane inhalation prior to Alzet pump placement. For intraperitoneal implantation, the following steps are performed:
1. Once the animal is anesthetized, the skin over the implantation site is shaved and washed.
2. A midline skin incision, 1 cm long, in the lower abdomen under the rib cage is made.
3. The musculoperitoneal layer is carefully tented up to avoid damage to the bowel. The peritoneal wall directly beneath the cutaneous incision is incised.
4. A filled pump, delivery portal first, is inserted into the peritoneal cavity.
5. The musculoperitoneal layer is closed with 4.0 absorbable suture in an interrupted or continuous pattern, taking care to avoid perforation of the underlying bowel.
6. The skin incision is closed with 2 or 3 wound clips or interrupted sutures.

Blood Sample Collection and Processing
Dosing and sampling are performed as follows:
Group 1: Oral Bolus: N=5 mice
Fast prior to PK sampling
Days 1, 14, 21, 28: Record BWs
PK Sampling: As per table below
Days 1, 14, 21, 28: collect predose CK, total sialylation and NCAM samples
Days 1-28: Single Oral Dose
Day 29: final blood collection (CK, total sialylation and NCAM samples) and necropsy; assay a set of muscles for surface sialylation
Groups 2 and 3: IP Alzet Pump: N=5 mice for each group
Fast prior to PK sampling
Day −1: implant pumps
Days 1, 14, 21, 28: Record BWs
PK Sampling: As per table below.
Days 1, 14, 21 collect predose CK, total sialylation and NCAM samples
Day 29: final blood collection (CK, total sialylation and NCAM samples) and necropsy.
PK Sample Collection Schedule

| GROUP 1: Oral Bolus Group Sample Collection Time Points (Time Post Dose) on Day 1, 14 and 28 | | |
| --- | --- | --- |
| Group No. | Pre | 1 hr |
| 1 | x | x |

| GROUPS 2 AND 3: Pump Group Sample Collection Time Points (Time Post Dose) on Days 1, 14, 28 | |
| --- | --- |
| Group No. | Pre |
| 2 | x |

Blood samples are collected at the prescribed time points/days as described above.

PK samples: Approx. 25 uL whole blood/time point. Blood samples are collected in serum tubes or in a 96 well plate. The blood is allowed to clot in the tubes at RT for 1 hr prior to centrifugation. Serum samples are stored at −80° C. for the duration of the study.

CK samples: At least 200 uL whole blood/time point is collected for CK clinical chemistry.

NCAM samples: Approx. 125 uL whole blood/time point. Blood samples are collected in serum separator tubes. The blood is allowed to clot in the tubes at RT for 1 hr prior to centrifugation. Serum samples are stored at −80° C. for the duration of the study.

Tissue Collection and Processing

After the last blood sample collection, mice are euthanized and tissue samples are collected. Muscle is analyzed for sialylation via lectin staining and Western Blot. Tissues are analyzed with H & E Staining/trichrome and Congo Red.

The following tissues are collected on Day 29:
Quadracep muscle
Hamstring muscle
Bicep muscle
Tricep muscle
Tibialis anterior For the tissue samples, three pieces for each muscle are needed:
1. 1 piece fixed in 10% Neutral Buffered Formalin, for paraffin embedding & sectioning and staining with H&E, Congo Red and Masson's Trichrome.
2. 1 piece frozen in a microfuge tube at −80 degrees for frozen sections for lectin staining.
3. 1 piece weighed and frozen at −80 degrees in a microfuge tube for extract preparation for NCAM and other westerns as well as biochemistry of sialylation (total bound sialic, GM3 levels.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

We claim:

1. An extended release pharmaceutical formulation in solid oral unit dosage form comprising
about 40% to about 45% w/w of N-acetylneuraminic acid (NeuAc), or a pharmaceutically acceptable salt thereof;
about 20% to about 30% w/w of one or more hydrophilic polymers, wherein the one or more hydrophilic polymers comprise one or more water-swellable, pH independent polymers or hydrogel, and the water-swellable, pH independent polymer is selected from the group consisting of hypromellose, hydroxypropyl ethyl cellulose, hydroxypropyl cellulose, hydroxyethyl cellulose, and methyl cellulose; and the hydrogel is selected from the group consisting of polyhydroxyethyl methylacrylate (PHEMA), polyvinyl alcohol (PVA), polyvinylpyrrolidone (PVP), polyethylene oxide (PEO), and polyacrylamide (PA);
about 20% to about 25% w/w of one or more anionic, pH-dependent, gel-forming polymers, wherein the one or more anionic, pH-dependent, gel-forming copolymers comprise one or more alginate or salts thereof, or carboxymethyl cellulose or salts thereof; and
about 1% to about 5% w/w of one or more hydrocolloid polymers or one or more cationic polymers, wherein the one or more hydrocolloid polymers comprise one or more carrageenans; and the one or more cationic polymers comprise chitosan, trimethylchitosan, quarternized chitosan, glycated chitosan, or galacto-chitosan
wherein each unit dosage form contains about 325 mg or about 500 mg of NeuAc; and upon oral administration to a human patient three or four times per day, the formulation provides a therapeutically effective amount and a steady plasma concentration of NeuAc over a period of greater than 6 hours.

2. The extended release pharmaceutical formulation of claim 1, wherein the one or more water-swellable, pH independent polymers comprise hypromellose.

3. The extended release pharmaceutical formulation of claim 2, comprising about 22% to about 27% w/w of hypromellose.

4. The extended release pharmaceutical formulation of claim 1, wherein one or more anionic, pH-dependent, gel-forming polymers comprise an alginate salt.

5. The extended release pharmaceutical formulation of claim 4, wherein the alginate salt comprises sodium alginate.

6. The extended release pharmaceutical formulation of claim 1, comprising about 20% to about 23% w/w of one or more anionic, pH-dependent, gel-forming polymers.

7. The extended release pharmaceutical formulation of claim 1, wherein the one or more carrageenans comprise lamda carrageenan.

8. The extended release pharmaceutical formulation of claim 1, further comprising about 1% to about 10% of a mixture of microcrystalline cellulose and colloidal silicon dioxide.

9. The extended release pharmaceutical formulation of claim 1, further comprising about 0.1% to about 1% of one or more lubricants.

10. The extended release pharmaceutical formulation of claim 9, wherein the one or more lubricants comprise magnesium stearate.

11. The extended release pharmaceutical formulation of claim 1, which provides a therapeutically effective amount of sialic acid over a period of about 8 to about 10 hours.

12. The extended release pharmaceutical formulation of claim 1, which provides a sialic acid plasma concentration with a $C_{max}$ of about 0.5 to about 2.5 µg/mL.

13. The extended release pharmaceutical formulation of claim 12, which provides a sialic acid plasma concentration with a $C_{max}$ of about 0.5 to about 1 µg/mL.

14. The extended release pharmaceutical formulation of claim 1, which provides a sialic acid plasma concentration with a $C_{min}$ of about 0.1 to about 1 µg/mL.

15. The extended release pharmaceutical formulation of claim 14, which provides a sialic acid plasma concentration with a $C_{min}$ of about 0.1 to about 0.5 µg/mL.

16. The extended release pharmaceutical formulation of claim 1, which is a tablet or capsule.

\* \* \* \* \*